US010113180B2

(12) United States Patent
Lagudah et al.

(10) Patent No.: US 10,113,180 B2
(45) Date of Patent: Oct. 30, 2018

(54) WHEAT STEM RUST RESISTANCE GENE

(71) Applicant: COMMONWEALTH SCIENTIFIC AND INDUSTRIAL RESEARCH ORGANISATION, Campbell, Australian Capital Territory (AU)

(72) Inventors: Evans Lagudah, Ngunnawal (AU); Sambasivam Kuppusamy Periyannan, Turner (AU)

(73) Assignee: Commonwealth Scientific and Industrial Research Organisation, Acton (AU)

( * ) Notice: Subject to any disclaimer, the term of this patent is extended or adjusted under 35 U.S.C. 154(b) by 0 days.

(21) Appl. No.: 14/895,879

(22) PCT Filed: Jun. 6, 2014

(86) PCT No.: PCT/AU2014/000594
§ 371 (c)(1),
(2) Date: Dec. 3, 2015

(87) PCT Pub. No.: WO2014/194371
PCT Pub. Date: Dec. 11, 2014

(65) Prior Publication Data

US 2016/0138042 A1 May 19, 2016

(30) Foreign Application Priority Data

Jun. 6, 2013 (AU) ................................ 2013902049

(51) Int. Cl.

| | |
|---|---|
| ***C12N 15/82*** | (2006.01) |
| ***A01H 5/10*** | (2018.01) |
| ***A23L 7/10*** | (2016.01) |
| ***C07K 14/415*** | (2006.01) |
| ***C12Q 1/6895*** | (2018.01) |

(52) U.S. Cl.
CPC .......... *C12N 15/8282* (2013.01); *A01H 5/10* (2013.01); *A23L 7/10* (2016.08); *C07K 14/415* (2013.01); *C12Q 1/6895* (2013.01); *A23V 2002/00* (2013.01); *C12Q 2600/13* (2013.01); *C12Q 2600/156* (2013.01)

(58) Field of Classification Search
CPC .......................... C12N 15/8282; C07K 14/415
See application file for complete search history.

(56) References Cited

U.S. PATENT DOCUMENTS 3,974,298 A * 8/1976 Cauvain ................ A21D 6/003 426/463
7,812,221 B2 * 10/2010 Regina .................... A01H 5/10 426/578
2003/0192074 A1 * 10/2003 Schulze-Lefert .... C07K 14/415 800/279
2010/0260729 A1 * 10/2010 Cavato .................... A01H 5/10 424/93.7
2011/0223303 A1 * 9/2011 Lagudah ............. C07K 14/415 426/443

FOREIGN PATENT DOCUMENTS

WO 2001/040512 7/2001

OTHER PUBLICATIONS

Periyannan, Sambasivam, et al. "An overview of genetic rust resistance: From broad to specific mechanisms." PLoS pathogens 13.7 (2017): e1006380.*
Golovkin, Maxim, and Anireddy SN Reddy. "An SC35-like protein and a novel serine/arginine-rich protein interact with Arabidopsis U1-70K protein." Journal of Biological Chemistry 274.51 (1999): 36428-36438.*
Brueggeman et al. (2008) "The stem rust resistance gene RpgS encodes a protein with nucleotide-binding-site, leucine-rich, and protein kinase domains" PNAS, 105:14970-14975.
Klindworth et al. (2012) "Introgression and Characterisation of a Goatgrass Gene for a High Level of Resistance to Ug99 Stem Rust in Tetraploid Wheat" G3: Genes, Genomes, Genetics, 2:665-673.
Olson et al. (2013) "Simultaneous transfer, introgression, and genomic localization of genes for resistance to stem rust race TTKSK (Ug99) from Aegilops tauschii to wheat", Theoretical and Applied Genetics, 126:1179-1188.
Periyannan et al. (2013) "The Gene Sr33, an Ortholog of Barley MIa Genes, Encodes Resistance to Wheat Stem Rust Race Ug99" Science, 341:786-788.
Rouse et al. (2011) "Genetics of Resistance to Race TTKSK of *Puccinia graminis* f. sp. tritici in Triticum monococcum" Phytopathology, 101:1418-1423.
Singh et al. (2011) "The Emergence of Ug99 Races of the Stem Rust Fungus is a Threat to World Wheat Production" Annual Review of Phytopathology, 49:465-481.
Steffenson et al. (2009) "Resistance to Stem Rust Race TTKSK Maps to the rpg4/Rpg5 Complex of Chromosome 5H of Barley" Phytopathology, 99:1135-1141.
Olivera, Pablo, et al., (2012) "Resistance to Race TTKSK of f. sp. in Emmer Wheat", Crop Science, 52(5):2234.
Bulgarelli et al. (2010) "The CC-NB-LRR-Type Rdg2a Resistance Gene Confers Immunity to the Seed-Borne Barley Leaf Stripe Pathogen in the Absence of Hypersensitive Cell Death", PLoS ONE, 5(9):1-14.

(Continued)

*Primary Examiner* — Lee A Visone
*Assistant Examiner* — Weihua Fan
(74) *Attorney, Agent, or Firm* — Michael B. Rubin; Bozicevic, Field & Francis LLP

(57) ABSTRACT

The present invention relates to a transgenic plant which has integrated into its genome an exogenous polynucleotide encoding a polypeptide which confers resistance to *Puccinia graminis* f. sp. *tritici*, such as the Ug99 group of races *Puccinia graminis* f. sp. *tritici*. In an embodiment, the polynucleotide is the Sr33 gene from *Aegilops tauschii*.

24 Claims, 9 Drawing Sheets

Figure 1:
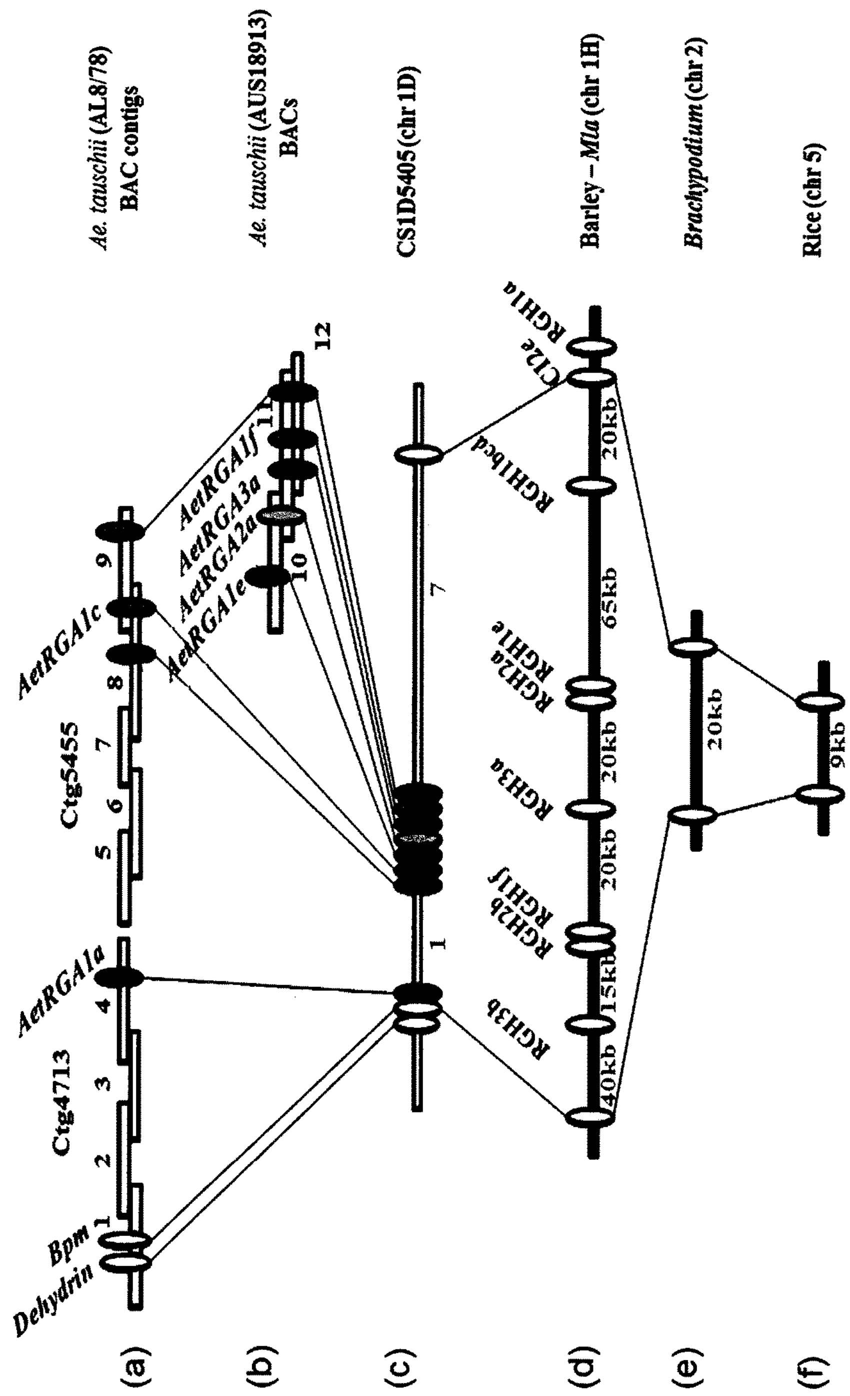

Specification includes a Sequence Listing.

(56) References Cited

OTHER PUBLICATIONS

Cooley et al. (2000) "Members of the Arabidopsis HRT/RPP8 Family of Resistance Genes Confer Resistance to Both Viral and Oomycete Pathogens", Plant Cell, 12:663-676.
Dilbirligi and Gill (2003) "Identification and analysis of expressed resistance gene sequences in wheat", Plant Molecular Biology, 53: 771-787.
Gennaro et al. (2009) "A candidate for Lr19, an exotic gene conditioning leaf rust resistance in wheat", Funct Integr Genomics, 9:325-334.
Jones et al. (1991) "Use of double-ditelosomic and normal chromosome 1D recombinant substitution lines to map Sr33 on chromosome arm IDS in wheat", Genome, 34:505-508.
Jordan et al. (2011) "The wheat MIa homologue TmMIa1 exhibits an evolutionarily conserved function against powdery mildew in both wheat and barley", Plant J, 65:610-621.
Krattinger et al. (2009) "A Putative ABC Transporter Confers Durable Resistance to Multiple Fungal Pathogens in Wheat", Science, 323:37-395.
Lagudah et al. (2006) "Molecular genetic characterization of the Lr34/Yr18 slow rusting resistance gene region in wheat", Theor. Appl. Genet., 114:21-30.
Lagudah et al. (2009) "Gene-speciWc markers for the wheat gene Lr34/Yr18/Pm38 which confers resistance to multiple fungal pathogens", Theor. Appl. Genet., 119:889-898.
Luo et al. (2003) "High-throughput fingerprinting of bacterial artificial chromosomes using the SNaPshot labeling kit and sizing of restriction fragments by capillary electrophoresis", Genomics 82:378-389.
Mago et al. (2002) "Identification and mapping of molecular markers linked to rust resistance genes located on chromosome 1RS of rye using wheat-rye translocation lines", Theor Appl Genet, 104:1317-1324.
Mago et al. (2005) "High-resolution mapping and mutation analysis separate the rust resistance genes Sr31, Lr26 and Yr9 on the short armof rye chromosome 1", Theor Appl Genet, 112:41-50.
McHale et al. (2006) "Plant NBS-LRR proteins: adaptable guards", Genome Biology 7:212.
Moullet et al. (1999) "Construction and characterisation of a large DNA insert library from the D genome of wheat", Theor Appl Genet, 99: 305-313.
Pan et al. (2000) "Divergent Evolution of Plant NBS-LRR Resistance Gene Homologues in Dicot and Cereal Genomes", J Mol Evol, 50:203-213.
Periyannan et al. (2013) "The Gene Sr33, an Ortholog of Barley MIa Genes, Encodes Resistance to Wheat Stem Rust Race Ug99", Sciencexpress Reports, pp. 1-5.
Saintenac et al. (2013) "Identification of Wheat Gene Sr35 That Confers Resistance to Ug99 Stem Rust Race Group", Sciencexpress Reports, pp. 1-6.
Seeholzer et al. (2010) "Diversity at the MIa Powdery Mildew Resistance Locus from Cultivated Barley Reveals Sites of Positive Selection", Mol Plant Microbe Interact, 23(4):497-509.
Singh et al. (2011) "The Emergence of Ug99 Races of the Stem Rust Fungus is a Threat to World Wheat Production", Annu. Rev. Phytopathol, 49:465-81.
Takken et al. (2006) "Resistance proteins: molecular switches of plant defence", Current Opinion in Plant Biology, 9:383-390.
Tameling et al. (2002) "The Tomato R Gene Products I-2 and Mi-1 Are Functional ATP Binding Proteins with ATPase Activity", Plant Cell, 14:2929-2939.
Traut (1994) "The functions and consensus motifs of nine types of peptide segments that form different types of nucleotide-binding sites", Eur. J. Biochem, 222:9-19.
Wei et al. (2002) "Genome Dynamics and Evolution of the MIa (Powdery Mildew) Resistance Locus in Barley", Plant Cell, 14:1903-1917.
Zhang et al. (2011) "Isolation and Characterization of NBS-LRR Class Resistance Homologous Gene from Wheat", Agricultural Sciences in China, 10(8): 1151-1158.
GenBank: AAO16000.1, (2003) "CC-NBS-LRR resistance protein MLA12 (*Hordeum vulgare*)", 2 pages.
GenBank: ACZ65487.1, (2010) "MLA9 (*Hordeum vulgare* subsp. Vulgare)", 2 pages.
GenBank: ACZ65501.1, (2010) "MLA34 (*Hordeum vulgare* subsp. Spontaneum)", 2 pages.
GenBank: ADX06722.1, (2011) "MIa1 (*Triticum monococcum*)", 2 pages.
GenBank: AUS18913, (2018) "phosphate acetyltransferase (*Klebsiella pneumoniae* subsp. Pneumoniae)", 2 pages.
GenBank: BE587232.1, (2000) "WHE0510_E08_I16ZR Secale cereal alimunim-stressed root tip cDNA Secale cereal cDNA clone WHE0510_E08_I16, mRNA sequence", 2 pages.
GenBank: CPI110799 (2013) "Aegilops tauschii cultivar CPI110799 RGA2a gene, complete cds", 3 pages.
GenBank: EMS45849.1 (2015) "Disease resistance protein RPP13 (*Triticum urartu*)", 2 pages.
GenBank: KF031284 (2013) "Aegilops tauschii cultivar AUS18913 RGA1e gene, complete cds", 2 pages.
GenBank: KF031297 (2013) "Aegilops tauschii cultivar P1603225 RGA1e gene, complete cds", 2 pages.
GenBank: KF031298 (2013) "Aegilops tauschii cultivar CPI110908 RGA1e gene, partial cds", 2 pages.
GenBank: KF031299 (2013) "Aegilops tauschii cultivar AUS18911 RGA1e gene, complete cds", 2 pages.
GenBank: PI603225 (2013) "Aegilops tauschii cultivar PI603225 RGA1e gene, complete cds", 2 pages.
European Patent Application No. 14807302.6, Response to Examination Report filed May 4, 2018, 9 pages.

* cited by examiner

```
HaplotypeI     MDIVTGAIAKLIPKLGELLVGEYKLHKGVKKNIEDLLKELKTMNAALIKIGEVPPDQLDS 60
HaplotypeII    MDIVTGAIAKLIPKLGELLVGEYKLHKGVKKNIEDLLKELKTMNAALIKIGEVPPDQLDS 60
HaplotypeIII   MDIVTGAIAKLIPKLGELLVGEYKLHKGVKKNIEDLLKELKTMNAALIKIGEVPPDQLDS 60
HaplotypeIV    MDIVTGAIAKLIPKLGELLVGEYKLHKGVKKNIEDLLKELKTMNAALIKIGEVPPDQLDS 60
HaplotypeV     MDIVTGAIAKLIPKLGELLVGEYKLHKGVKKNIEDLLKELKTMNAALIKIGEVPPDQLDS 60

HaplotypeI     QDKLWADEVRELSYVIEDAVDKFLVRVHGVEPDDNTNGFKGLMKRTTKLLKKVVDKHGIA 120
HaplotypeII    QDKLWADEVRELSYVIEDAVDKFLVRVHGVEPDDNTNGFKGLMKRTTKLLKKVVDKHGIA 120
HaplotypeIII   QDKLWADEVRELSYVIEDAVDKFLVRVHGVEPDDNTNGFKGLMKRTTKLLKKVVDKHGIA 120
HaplotypeIV    QDKLWADEVRELSYVIEDAVDKFLVRVHGVEPDDNTNGFKGLMKRTTKLLKKVVDKHGIA 120
HaplotypeV     QDKLWADEVRELSYVIEDAVDKFLVRVHGVEPDDNTNGFKGLMKRTTKLLKKVVDKHGIA 120

HaplotypeI     HAIKDIKKELQEVAARRDRNKFDGIASIPTEAIDPRLRALYIEAAELVGIYGKRDQELMS 180
HaplotypeII    HAIKDIKKELQEVAARRDRNKFDGIASIPTEAIDPRLRALYIEAAELVGIYGKRDQELMS 180
HaplotypeIII   HAIKDIKKELQEVAARRDRNKFDGIASIPTEAIDPRLRALYIEAAELVGIYGKRDQELMS 180
HaplotypeIV    HAIKDIKKELQEVAARRDRNKFDGIASIPTEAIDPRLRALYIEAAELVGIYGKRDQELMS 180
HaplotypeV     HAIKDIKKELQEVAARRDRNKFDGIASIPTEAIDPRLRALYIEAAELVGIYGKRDQELMS 180

HaplotypeI     LLSLEGDDASTKKLKKVSIVGFGGLGKTTLAKAVYEKIKGDFDCHAFVPVGQNPDKKKVF 240
HaplotypeII    LLSLEGDDASTKKLKKVSIVGFGGLGKTTLAKAVYEKIKGDFDCHAFVPVGQNPDKKKVF 240
HaplotypeIII   LLSLEGDDASTKKLKKVSIVGFGGLGKTTLAKAVYEKIKGDFDCHAFVPVGQNPDKKKVF 240
HaplotypeIV    LLSLEGDDASTKKLKKVSIVGFGGLGKTTLAKAVYEKIKGDFDCHAFVPVGQNPDKKKVF 240
HaplotypeV     LLSLEGDDASTKKLKKVSIVGFGGLGKTTLAKAVYEKIKGDFDCHAFVPVGQNPDKKKVF 240

HaplotypeI     RDILMDLSNSNSDLALLDERQLINKLHKFLENKRYLVIIDDVWDEGLWKDINLAFSNRNN 300
HaplotypeII    RDILMDLSNSNSDLALLDERQLINKLHKFLENKRYLVIIDDVWDEGLWKDINLAFSNRNN 300
HaplotypeIII   RDILMDLSNSNSDLALLDERQLINKLHKFLENKRYLVIIDDVWDEGLWKDINLAFSNRNN 300
HaplotypeIV    RDILMDLSNSNSDLALLDERQLINKLHKFLENKRYLVIIDDVWDEGLWKDINLAFSNRNN 300
HaplotypeV     RDILMDLSNSNSDLALLDERQLINKLHKFLENKRYLVIIDDVWDEGLWKDINLAFSNRNN 300
```

Figure 6

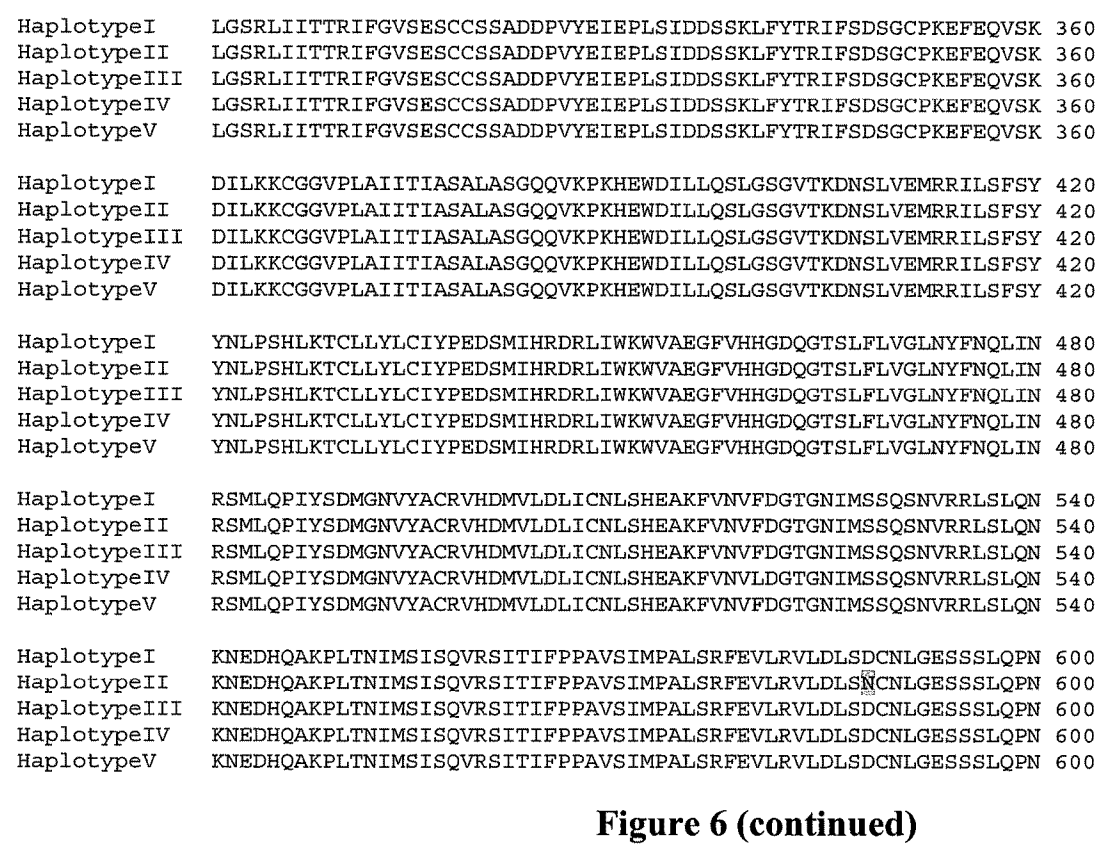

```
HaplotypeI     LGSRLIITTRIFGVSESCCSSADDPVYEIEPLSIDDSSKLFYTRIFSDSGCPKEFEQVSK 360
HaplotypeII    LGSRLIITTRIFGVSESCCSSADDPVYEIEPLSIDDSSKLFYTRIFSDSGCPKEFEQVSK 360
HaplotypeIII   LGSRLIITTRIFGVSESCCSSADDPVYEIEPLSIDDSSKLFYTRIFSDSGCPKEFEQVSK 360
HaplotypeIV    LGSRLIITTRIFGVSESCCSSADDPVYEIEPLSIDDSSKLFYTRIFSDSGCPKEFEQVSK 360
HaplotypeV     LGSRLIITTRIFGVSESCCSSADDPVYEIEPLSIDDSSKLFYTRIFSDSGCPKEFEQVSK 360

HaplotypeI     DILKKCGGVPLAIITIASALASGQQVKPKHEWDILLQSLGSGVTKDNSLVEMRRILSFSY 420
HaplotypeII    DILKKCGGVPLAIITIASALASGQQVKPKHEWDILLQSLGSGVTKDNSLVEMRRILSFSY 420
HaplotypeIII   DILKKCGGVPLAIITIASALASGQQVKPKHEWDILLQSLGSGVTKDNSLVEMRRILSFSY 420
HaplotypeIV    DILKKCGGVPLAIITIASALASGQQVKPKHEWDILLQSLGSGVTKDNSLVEMRRILSFSY 420
HaplotypeV     DILKKCGGVPLAIITIASALASGQQVKPKHEWDILLQSLGSGVTKDNSLVEMRRILSFSY 420

HaplotypeI     YNLPSHLKTCLLYLCIYPEDSMIHRDRLIWKWVAEGFVHHGDQGTSLFLVGLNYFNQLIN 480
HaplotypeII    YNLPSHLKTCLLYLCIYPEDSMIHRDRLIWKWVAEGFVHHGDQGTSLFLVGLNYFNQLIN 480
HaplotypeIII   YNLPSHLKTCLLYLCIYPEDSMIHRDRLIWKWVAEGFVHHGDQGTSLFLVGLNYFNQLIN 480
HaplotypeIV    YNLPSHLKTCLLYLCIYPEDSMIHRDRLIWKWVAEGFVHHGDQGTSLFLVGLNYFNQLIN 480
HaplotypeV     YNLPSHLKTCLLYLCIYPEDSMIHRDRLIWKWVAEGFVHHGDQGTSLFLVGLNYFNQLIN 480

HaplotypeI     RSMLQPIYSDMGNVYACRVHDMVLDLICNLSHEAKFVNVFDGTGNIMSSQSNVRRLSLQN 540
HaplotypeII    RSMLQPIYSDMGNVYACRVHDMVLDLICNLSHEAKFVNVFDGTGNIMSSQSNVRRLSLQN 540
HaplotypeIII   RSMLQPIYSDMGNVYACRVHDMVLDLICNLSHEAKFVNVFDGTGNIMSSQSNVRRLSLQN 540
HaplotypeIV    RSMLQPIYSDMGNVYACRVHDMVLDLICNLSHEAKFVNVLDGTGNIMSSQSNVRRLSLQN 540
HaplotypeV     RSMLQPIYSDMGNVYACRVHDMVLDLICNLSHEAKFVNVFDGTGNIMSSQSNVRRLSLQN 540

HaplotypeI     KNEDHQAKPLTNIMSISQVRSITIFPPAVSIMPALSRFEVLRVLDLSDCNLGESSSLQPN 600
HaplotypeII    KNEDHQAKPLTNIMSISQVRSITIFPPAVSIMPALSRFEVLRVLDLSNCNLGESSSLQPN 600
HaplotypeIII   KNEDHQAKPLTNIMSISQVRSITIFPPAVSIMPALSRFEVLRVLDLSDCNLGESSSLQPN 600
HaplotypeIV    KNEDHQAKPLTNIMSISQVRSITIFPPAVSIMPALSRFEVLRVLDLSDCNLGESSSLQPN 600
HaplotypeV     KNEDHQAKPLTNIMSISQVRSITIFPPAVSIMPALSRFEVLRVLDLSDCNLGESSSLQPN 600
```

Figure 6 (continued)

```
HaplotypeI     LKGVGHLIHLRYLGLSGTRISKLPAEIGTLQFLEVLDLGYNHELDELPSTLFKLRRLIYL 660
HaplotypeII    LKGVGHLIHLRYLGLSGTRISKLPAEIGTLQFLEVLDLGYNHELDELPSTLFKLRRLIYL 660
HaplotypeIII   LKGVGHLIHLRYLGLSGTRISKLPAEIGTLQFLEVLDLGYNHELDELPSTLFKLRRLIYL 660
HaplotypeIV    LKGVGHLIHLRYLGLSGTRISKLPAEIGTLQFLEVLDLGYNHELDELPSTLFKLRRLIYL 660
HaplotypeV     LKGVGHLIHLRYLGLSGTRISKLPAEIGTLQFLEVLDLGYNHELDELPSTLFKLRRLIYL 660

HaplotypeI     NVSPYKVVPTPGVLQNMTSIEVLRGIFVSLNIIAQELGKLARLRELQIYFKDGSLDLYEG 720
HaplotypeII    NVSPYKVVPTPGVLQNMTSIEVLRGIFVSLNIIAQELGKLARLRELQIYFKDGSLDLYEG 720
HaplotypeIII   NVSPYKVVPTPGVLQNMTSIEVLRGIFVSLNIIAQELGKLARLRELQIYFKDGSLDLYEG 720
HaplotypeIV    NVSPYKVVRTLGVLQNMTSIEVLRGIFVSLNIIAQELGKLARLRELQIRFKDGSLDLYEG 720
HaplotypeV     NVSPYEVVPTPGVLQNMTSIEVLRGIFVSEHYCT---------RAWQTGKAEGASDLLQG 711

HaplotypeI     FVKSLCNLHHIESLIVSCNSGETSFELMDLLGEQWVPPVHLREFVSEMPSQLSALRGWIK 780
HaplotypeII    FVKSLCNLHHIESLIVSCNSGETSFELMDLLGEQWVPPVHLREFVSEMPSQLSALRGWIK 780
HaplotypeIII   FVKSLCNLHHIESLIVSCNSGETSFELMDLLGEQWVPPVHLREFVSHMPSQLSALRGWIK 780
HaplotypeIV    FVKSLCNLHQIESLITDCNSEEASFELMDLLGERWVPPVHLREFVSYMPSQLSALRGWIK 780
HaplotypeV     W----------------------------------------------------------- 712

HaplotypeI     RDPSHLSNLSELILPTVKEVQQEDVEIIGGLLSLRRLLIESTHQTQRLLVIRADGFRCMV 840
HaplotypeII    RDPSHLSNLSELILPTVKEVQQEDVEIIGGLLSLRRLLIESTHQTQRLLVIRADGFRCMV 840
HaplotypeIII   RDPSHLSNLSELILPTVKEVQQEDVEIIGGLLSLRRLWIKTTHQTQRLLVIRADGFRCMV 840
HaplotypeIV    RDPSHLSNLSELILTSVKEVQQEDVEIIGGLLSLRRLRIWSTHQTQRLLVIRADGFRCMV 840
HaplotypeV     ------------------------------------------------------------

HaplotypeI     DFYLNCGSATQIMFESGALPRAEEVCFSLGVRVAKEDGNRGFDLGLQGNLLSLRRVVWVK 900
HaplotypeII    DFYLNCGSATQIMFESGALPRAEEVCFSLGVRVAKEDGNRGFDLGLQGNLLSLRRVVWVK 900
HaplotypeIII   DFHLNCGSATQIMFESGALPRAEEVCFSLGVRVAKEDGNRGFDLGLQGNLLSLRRVVWVK 900
HaplotypeIV    DFYLNCRSAAQIKFEPGALPRAEGVVFSLGVRVAKEDGNRGFDLGLQGNLLSLRRVVLVK 900
HaplotypeV     ------------------------------------------------------------

HaplotypeI     MYCGGARVGEAKEAKAAVRHALEDHPNHPPIQINMFPRIAEGAQDDDLMCYPVGGPISDAE 961
HaplotypeII    MYCGGARVGEAKEAKAAVRHALEDHPNHPPIQINMFPRIAEGAQDDDLMCYPVGGPISDAE 961
HaplotypeIII   MYCGGARVGEAKEAKAAVRHALEDHPNHPPIQINMFPRIAEGAQDDDLMCYPAGGPISDAE 961
HaplotypeIV    MYCGGARVGEAKEAEAAVRHALEDHPNHPPIEINMLPHIAK-------------------- 941
HaplotypeV     -------------------------------------------------------------
```

Figure 6 (continued)

SEQUENCE LISTING

```
<160> NUMBER OF SEQ ID NOS: 116

<210> SEQ ID NO 1
<211> LENGTH: 961
<212> TYPE: PRT
<213> ORGANISM: Aegilops tauschii

<400> SEQUENCE: 1

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45
```

```
Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95

Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
            260                 265                 270

Lys Arg Tyr Leu Val Ile Ile Asp Asp Val Trp Asp Glu Gly Leu Trp
        275                 280                 285

Lys Asp Ile Asn Leu Ala Phe Ser Asn Arg Asn Asn Leu Gly Ser Arg
    290                 295                 300

Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
                325                 330                 335

Ser Ser Lys Leu Phe Tyr Thr Arg Ile Phe Ser Asp Ser Gly Cys Pro
            340                 345                 350

Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
```

```
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Phe Asp Gly Thr Gly Asn Ile Met Ser
        515                 520                 525

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asp Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Lys Val Val Pro Thr Pro Gly
            660                 665                 670

Val Leu Gln Asn Met Thr Ser Ile Glu Val Leu Arg Gly Ile Phe Val
        675                 680                 685

Ser Leu Asn Ile Ile Ala Gln Glu Leu Gly Lys Leu Ala Arg Leu Arg
    690                 695                 700

Glu Leu Gln Ile Tyr Phe Lys Asp Gly Ser Leu Asp Leu Tyr Glu Gly
705                 710                 715                 720

Phe Val Lys Ser Leu Cys Asn Leu His His Ile Glu Ser Leu Ile Val
                725                 730                 735

Ser Cys Asn Ser Gly Glu Thr Ser Phe Glu Leu Met Asp Leu Leu Gly
            740                 745                 750

Glu Gln Trp Val Pro Pro Val His Leu Arg Glu Phe Val Ser Glu Met
        755                 760                 765

Pro Ser Gln Leu Ser Ala Leu Arg Gly Trp Ile Lys Arg Asp Pro Ser
    770                 775                 780

His Leu Ser Asn Leu Ser Glu Leu Ile Leu Pro Thr Val Lys Glu Val
785                 790                 795                 800

Gln Gln Glu Asp Val Glu Ile Ile Gly Gly Leu Leu Ser Leu Arg Arg
                805                 810                 815

Leu Leu Ile Glu Ser Thr His Gln Thr Gln Arg Leu Leu Val Ile Arg
            820                 825                 830

Ala Asp Gly Phe Arg Cys Met Val Asp Phe Tyr Leu Asn Cys Gly Ser
        835                 840                 845

Ala Thr Gln Ile Met Phe Glu Ser Gly Ala Leu Pro Arg Ala Glu Glu
    850                 855                 860

Val Cys Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
                885                 890                 895
```

```
Val Trp Val Lys Met Tyr Cys Gly Gly Ala Arg Val Gly Glu Ala Lys
            900                 905                 910

Glu Ala Lys Ala Ala Val Arg His Ala Leu Glu Asp His Pro Asn His
        915                 920                 925

Pro Pro Ile Gln Ile Asn Met Phe Pro Arg Ile Ala Glu Gly Ala Gln
    930                 935                 940

Asp Asp Asp Leu Met Cys Tyr Pro Val Gly Gly Pro Ile Ser Asp Ala
945                 950                 955                 960

Glu


<210> SEQ ID NO 2
<211> LENGTH: 961
<212> TYPE: PRT
<213> ORGANISM: Aegilops tauschii

<400> SEQUENCE: 2

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95

Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
            260                 265                 270

Lys Arg Tyr Leu Val Ile Ile Asp Asp Val Trp Asp Glu Gly Leu Trp
        275                 280                 285

Lys Asp Ile Asn Leu Ala Phe Ser Asn Arg Asn Asn Leu Gly Ser Arg
    290                 295                 300
```

```
Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
                325                 330                 335

Ser Ser Lys Leu Phe Tyr Thr Arg Ile Phe Ser Asp Ser Gly Cys Pro
            340                 345                 350

Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Phe Asp Gly Thr Gly Asn Ile Met Ser
        515                 520                 525

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asn Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Lys Val Val Pro Thr Pro Gly
            660                 665                 670

Val Leu Gln Asn Met Thr Ser Ile Glu Val Leu Arg Gly Ile Phe Val
        675                 680                 685

Ser Leu Asn Ile Ile Ala Gln Glu Leu Gly Lys Leu Ala Arg Leu Arg
    690                 695                 700

Glu Leu Gln Ile Tyr Phe Lys Asp Gly Ser Leu Asp Leu Tyr Glu Gly
705                 710                 715                 720
```

```
Phe Val Lys Ser Leu Cys Asn Leu His His Ile Glu Ser Leu Ile Val
            725                 730                 735

Ser Cys Asn Ser Gly Glu Thr Ser Phe Glu Leu Met Asp Leu Leu Gly
            740                 745                 750

Glu Gln Trp Val Pro Pro Val His Leu Arg Glu Phe Val Ser Glu Met
        755                 760                 765

Pro Ser Gln Leu Ser Ala Leu Arg Gly Trp Ile Lys Arg Asp Pro Ser
    770                 775                 780

His Leu Ser Asn Leu Ser Glu Leu Ile Leu Pro Thr Val Lys Glu Val
785                 790                 795                 800

Gln Gln Glu Asp Val Glu Ile Ile Gly Gly Leu Leu Ser Leu Arg Arg
            805                 810                 815

Leu Leu Ile Glu Ser Thr His Gln Thr Gln Arg Leu Leu Val Ile Arg
            820                 825                 830

Ala Asp Gly Phe Arg Cys Met Val Asp Phe Tyr Leu Asn Cys Gly Ser
        835                 840                 845

Ala Thr Gln Ile Met Phe Glu Ser Gly Ala Leu Pro Arg Ala Glu Glu
    850                 855                 860

Val Cys Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
            885                 890                 895

Val Trp Val Lys Met Tyr Cys Gly Gly Ala Arg Val Gly Glu Ala Lys
            900                 905                 910

Glu Ala Lys Ala Ala Val Arg His Ala Leu Glu Asp His Pro Asn His
        915                 920                 925

Pro Pro Ile Gln Ile Asn Met Phe Pro Arg Ile Ala Glu Gly Ala Gln
    930                 935                 940

Asp Asp Asp Leu Met Cys Tyr Pro Val Gly Gly Pro Ile Ser Asp Ala
945                 950                 955                 960

Glu
```

<210> SEQ ID NO 3
<211> LENGTH: 2886
<212> TYPE: DNA
<213> ORGANISM: Aegilops tauschii

<400> SEQUENCE: 3

```
atggatattg tcacgggtgc cattgccaag ctgatcccca agctgggaga actgcttgtg      60

ggggagtaca aactgcacaa gggcgtcaag aaaaatatcg aggacctcct gaaagagctc     120

aagaccatga acgctgcgct catcaagatt ggtgaggtgc cgccggacca gctcgacagc     180

caagacaagc tttgggccga tgaggtcaga gagctctcct acgtcattga ggatgcggtg     240

gacaagttcc tcgtacgggt ccatggcgtt gagcccgacg acaacaccaa cggattcaag     300

gggctcatga agaggaccac caagttgttg aagaaagtcg tggataagca tggaatagct     360

cacgcgatca aggacatcaa gaaggaactc caggaggtgg ctgctaggcg tgacaggaac     420

aagttcgatg gtattgcttc tattcctact gaagcaattg atcctcgtct ccgtgctcta     480

tacatagaag cggcagagct agttggcatc tatgggaaga gggatcagga gctcatgagt     540

ttgctctcct tggagggcga tgatgcctct accaagaaac tgaagaaggt ctccattgtt     600

ggatttggag ggttgggcaa gaccactctt gccaaagcag tatacgagaa gattaaaggt     660

gattttgatt gtcacgcatt tgttcctgtc gggcagaacc ctgacaagaa gaaggttttt     720
```

```
agggatatcc tcatggatct cagcaactct aactcagatc ttgcattatt ggatgaaagg    780
cagcttatca acaaacttca taaatttctc gagaacaaga ggtaccttgt cataattgat    840
gatgtatggg atgaaggttt gtggaaagac atcaaccttg ctttctccaa caggaacaat    900
ctaggcagtc ggctaatcat cacaacccgc atttttggtg tctccgagtc atgttgctca    960
tcggctgatg atccggttta tgaaattgaa cctctttcca tagatgactc cagcaagctc   1020
ttctatacaa gaatattctc ggatagtgga tgcccaaagg aatttgaaca agtgtctaaa   1080
gatatattga agaaatgtgg tggggtacca ctagccatca ttactattgc tagtgctttg   1140
gctagtggcc agcaagtgaa accaaagcat gagtgggata ttctactcca gtcccttggc   1200
tccggagtaa caaaagataa cagtttggtt gagatgcgga gaatactatc attcagctat   1260
tataatctac cgtctcatct gaaaacctgt ctactgtacc tatgtatata tccagaagat   1320
agcatgattc atagagatag actcatatgg aagtgggtgg ccgaaggatt tgtccaccat   1380
ggagatcaag ggaccagcct atttttggtc ggattaaact acttcaacca gctcattaat   1440
agaagtatgc tccagccaat atattcggat atgggcaacg tatatgcttg ccgtgtacat   1500
gatatggttc tggaccttat ctgcaacttg tcacatgaag caaagtttgt taatgtattc   1560
gatggcactg ggaatatcat gtcttcacaa agtaatgttc gccgcttgtc ccttcagaat   1620
aaaaatgaag atcatcaagc caaacctctc acaaatatca tgagtatctc acaagtgagg   1680
tcaattacta tctttccacc tgctgtcagt atcatgccag ccctgtcaag gtttgaagtt   1740
ctacgggtac ttgatttgtc ggactgtaac cttggggaaa gtagcagcct gcagcctaac   1800
ctcaagggtg ttggacactt aattcaccta aggtacctag gtctatcagg taccagaatt   1860
agtaaactcc cggctgagat aggaaccctg cagtttctgg aggtgttgga tcttggatac   1920
aatcatgagc tagatgaatt gccttccact ctttttaaat tgagaagatt aatctaccta   1980
aatgtttctc cctataaggt ggttccaact cctggtgtgt tgcagaatat gacatccata   2040
gaagtgttga gggggatctt tgtctctctg aacattattg cacaagagct tggcaaactg   2100
gcaaggctga gggagcttca gatttacttc aaggatggta gtttggattt gtatgaaggt   2160
ttcgtgaagt ctctgtgcaa cttacatcac atcgaaagcc taattgttag ttgcaattct   2220
ggagaaacat cttttgaact gatggatctc ttgggagaac aatgggtgcc tcctgtacat   2280
ctccgcgaat ttgtgtcaga aatgcccagc caactctctg cactgcgagg gtggataaag   2340
agagacccct cgcatctctc gaacctctcc gagttaatcc tcccgacagt gaaggaagtg   2400
cagcaggagg acgtggaaat cattgggggg ttgctgtccc ttcgccgtct gctcatagag   2460
agcacccacc aaacacaacg gctgctagtc atccgtgcag atgggttccg ctgtatggta   2520
gacttttact tgaattgtgg atccgcaacg cagataatgt ttgaatcagg agctttgccg   2580
agggcggaag aagtttgctt cagcctgggc gtgcgggtgg cgaaagagga tggtaaccgt   2640
ggtttcgact tgggcctgca ggggaacctg ctctcccttc ggcgggtggt ctgggttaag   2700
atgtattgtg gtggagcgag ggttggggag gccaaggaag cgaaggctgc ggtgaggcac   2760
gcactcgaag accatcccaa ccatcctccg attcaaatta acatgttccc gcgtatagca   2820
gaaggtgctc aagatgacga tttaatgtgt tacccggttg gaggaccgat ttctgacgca   2880
gagtga                                                              2886
```

<210> SEQ ID NO 4
<211> LENGTH: 2886
<212> TYPE: DNA
<213> ORGANISM: Aegilops tauschii

<400> SEQUENCE: 4

```
atggatattg tcacgggtgc cattgccaag ctgatcccca agctgggaga actgcttgtg     60
ggggagtaca aactgcacaa gggcgtcaag aaaaatatcg aggacctcct gaaagagctc    120
aagaccatga acgctgcgct catcaagatt ggtgaggtgc cgccggacca gctcgacagc    180
caagacaagc tttgggccga tgaggtcaga gagctctcct acgtcattga ggatgcggtg    240
gacaagttcc tcgtacgggt ccatggcgtt gagcccgacg acaacaccaa cggattcaag    300
gggctcatga agaggaccac caagttgttg aagaaagtcg tggataagca tggaatagct    360
cacgcgatca aggacatcaa gaaggaactc caggaggtgg ctgctaggcg tgacaggaac    420
aagttcgatg gtattgcttc tattcctact gaagcaattg atcctcgtct ccgtgctcta    480
tacatagaag cggcagagct agttggcatc tatgggaaga gggatcagga gctcatgagt    540
ttgctctcct tggagggcga tgatgcctct accaagaaac tgaagaaggt ctccattgtt    600
ggatttggag ggttgggcaa gaccactctt gccaaagcag tatacgagaa gattaaaggt    660
gattttgatt gtcacgcatt tgttcctgtc gggcagaacc ctgacaagaa gaaggttttt    720
agggatatcc tcatggatct cagcaactct aactcagatc ttgcattatt ggatgaaagg    780
cagcttatca acaaacttca taaatttctc gagaacaaga ggtaccttgt cataattgat    840
gatgtatggg atgaaggttt gtggaaagac atcaaccttg ctttctccaa caggaacaat    900
ctaggcagtc ggctaatcat cacaacccgc atttttggtg tctccgagtc atgttgctca    960
tcggctgatg atccggttta tgaaattgaa cctctttcca tagatgactc cagcaagctc   1020
ttctatacaa gaatattctc ggatagtgga tgcccaaagg aatttgaaca agtgtctaaa   1080
gatatattga agaaatgtgg tggggtacca ctagccatca ttactattgc tagtgctttg   1140
gctagtggcc agcaagtgaa accaaagcat gagtgggata ttctactcca gtcccttggc   1200
tccggagtaa caaaagataa cagtttggtt gagatgcgga gaatactatc attcagctat   1260
tataatctac cgtctcatct gaaaacctgt ctactgtacc tatgtatata tccagaagat   1320
agcatgattc atagagatag actcatatgg aagtgggtgg ccgaaggatt tgtccaccat   1380
ggagatcaag ggaccagcct atttttggtc ggattaaact acttcaacca gctcattaat   1440
agaagtatgc tccagccaat atattcggat atgggcaacg tatatgcttg ccgtgtacat   1500
gatatggttc tggaccttat ctgcaacttg tcacatgaag caaagtttgt taatgtattc   1560
gatggcactg ggaatatcat gtcttcacaa agtaatgttc gccgcttgtc ccttcagaat   1620
aaaaatgaag atcatcaagc caaacctctc acaaatatca tgagtatctc acaagtgagg   1680
tcaattacta tctttccacc tgctgtcagt atcatgccag ccctgtcaag gtttgaagtt   1740
ctacgggtac ttgatttgtc gaactgtaac cttggggaaa gtagcagcct gcagcctaac   1800
ctcaagggtg ttggacactt aattcaccta aggtacctag gtctatcagg taccagaatt   1860
agtaaactcc cggctgagat aggaaccctg cagtttctgg aggtgttgga tcttggatac   1920
aatcatgagc tagatgaatt gccttccact ctttttaaat tgagaagatt aatctaccta   1980
aatgtttctc cctataaggt ggttccaact cctggtgtgt tgcagaatat gacatccata   2040
gaagtgttga gggggatctt tgtctctctg aacattattg cacaagagct tggcaaactg   2100
gcaaggctga gggagcttca gatttacttc aaggatggta gtttggattt gtatgaaggt   2160
ttcgtgaagt ctctgtgcaa cttacatcac atcgaaagcc taattgttag ttgcaattct   2220
ggagaaacat cttttgaact gatggatctc ttgggagaac aatgggtgcc tcctgtacat   2280
```

```
ctccgcgaat ttgtgtcaga aatgcccagc caactctctg cactgcgagg gtggataaag   2340

agagacccct cgcatctctc gaacctctcc gagttaatcc tcccgacagt gaaggaagtg   2400

cagcaggagg acgtggaaat cattgggggg ttgctgtccc ttcgccgtct gctcatagag   2460

agcacccacc aaacacaacg gctgctagtc atccgtgcag atgggttccg ctgtatggta   2520

gacttttact tgaattgtgg atccgcaacg cagataatgt ttgaatcagg agctttgccg   2580

agggcggaag aagtttgctt cagcctgggc gtgcgggtgg cgaaagagga tggtaaccgt   2640

ggtttcgact tgggcctgca ggggaacctg ctctcccttc ggcgggtggt ctgggttaag   2700

atgtattgtg gtggagcgag ggttggggag gccaaggaag cgaaggctgc ggtgaggcac   2760

gcactcgaag accatcccaa ccatcctccg attcaaatta acatgttccc gcgtatagca   2820

gaaggtgctc aagatgacga tttaatgtgt tacccggttg gaggaccgat ttctgacgca   2880

gagtga                                                              2886
```

<210> SEQ ID NO 5
<211> LENGTH: 7783
<212> TYPE: DNA
<213> ORGANISM: Aegilops tauschii

<400> SEQUENCE: 5

```
gcagagggta tccctccctg taatacgtac tagtattcga ggagcgtgct aaagtagtat     60

cctctcttga tgctcctcgt ctccctccac tgagtactcc cttcctctcc tcattctcat    120

ctcagtcctc tcctcctccc tcgaataaga tagatccgcc cttgttgctg atctcatctc    180

gcctcctatt ggcctcgccc ctgccaactg actgctctat tggtgaccgt ggactttttg    240

ggtatatata tttcctgtcg atttgtttcc acttaaagta gcaatgcttg gatctaaaac    300

ttattacttc tcctgcttca gattctgatc catttgtgtt gattgaactc agggtgggat    360

cgtggggctc tgtatctatc taggatggat attccaagca atttactctc ttgagtgctg    420

ttggtcttcc tctgctcctc gtctccgctt cctctcagtc tcctccattg cgctgcctgg    480

aacagatcga tccgccttgt tgctgatctc atccatcctc cgtggagatt tcgggtggca    540

gtttccagtg actattcaga gcaccatact agtggcctgg taaaaatttc cctcccatct    600

ttcttgctat tctcttctta ttaatctgct gatttgcttg atggtaagtt cttacttatt    660

cttccagatc gagtgaagcg acatccgccg ccgtcttgtc ccctacgacg ccgctgtgtt    720

ctgctctgtc ctcctctgcc ggtgaagcat caacggtgac ggccatccgg tgttgacgcc    780

gcggctgtgt tctcctctgc cgtgaagtat caaaggtggg tttggatgga tatcacagtt    840

tggattggca actctgttct atagctcgtt gaaattaaag cttcacacag ttttgattgg    900

attacagctc cccatattca tctattttgc accatgcatc gaatccactg acctccacac    960

gctcacggat ctggcctctg gtgcccacac gctcacggat ccgacagagt gctcccttcc   1020

tatcatctca gtcctcatct cctggtcgat ccggcttctt gtttggtgag ctcgtccaac   1080

ctccgagctc gcccctgaca cctgtggagt ggaggtatat ttctttccag ctgaagtacg   1140

cttggatcta aaaacttacg tctcctgctt cactgcttgc ttgggagtct gatcgatttg   1200

tgttggttga atcatttggg gtggcagtgg agcagctagc aagaatcatg gagtttccaa   1260

tcattattca gagcaccacg catggaatcc actgacctgg taactttgtc tcatctttct   1320

tgctactgaa atcttccaca tccccacctt ccttgttcat ctgctgattt cccagattat   1380

acttccagat tgagtgaagc gccgtcttgt cccctcacgg atctggcctc tggtgcccag   1440

ccgccgcttt cgcttcgttg tccgacgagg ccaccgccgc tgtgttctgc tctgccgtga   1500
```

```
agcacaaaaa ggtggggtct tcctctgctc tttctccact gacggcgatc cgaccttgac   1560
acccgtggcc gtggcagtgg ggtcttcctc tgctctgttt ttttaccagt tattggatct   1620
aaaaagggat ctaaaagtta ttacttctcc tgcttgagat tctgaccgat ttgtgttgat   1680
tgaatccagg gtggggtcgt ggggctctgt atctatctag tacggagtac cactgtattc   1740
caagcaattt actctcttga ctgctgttgg acttcctctg tccccgcttc cattgtgctg   1800
ccttgaacag atccatccac cttgttgcta atctcatcca acctccgggt atgtttcttg   1860
tcgatttgtt tccagtaaag tagcaatgct tgggtctaaa aagtcattgc ttctcctgct   1920
tgacgagtct cattgatttg cccagtcatt attcagagca ccatgcatcc aaggcgctga   1980
cccggctata agtttttatt acagggccgc cgtgttgtcc ccatcgagca aagcgtttaa   2040
tccactgacc cgcttcgttg tccgcacagc gtgaccatcc gacgaagacg ccgccgttgt   2100
gttctgctct cctctgaagc atcaaaaggt gggcttggtc cagatcccca cattcatcga   2160
tttggcttgc caactcagtt ccaccagagc ttggattgtg ttacagatcc ctaaattcat   2220
cgatttgcag gtttcagctg attgatcaag agagctctca tggatattgt cacgggtgcc   2280
attgccaagc tgatccccaa gctgggagaa ctgcttgtgg gggagtacaa actgcacaag   2340
ggcgtcaaga aaaatatcga ggacctcctg aaagagctca agaccatgaa cgctgcgctc   2400
atcaagattg gtgaggtgcc gccggaccag ctcgacagcc aagacaagct ttgggccgat   2460
gaggtcagag agctctccta cgtcattgag gatgcggtgg acaagttcct cgtacgggtc   2520
catggcgttg agcccgacga caacaccaac ggattcaagg ggctcatgaa gaggaccacc   2580
aagttgttga agaaagtcgt ggataagcat ggaatagctc acgcgatcaa ggacatcaag   2640
aaggaactcc aggaggtggc tgctaggcgt gacaggaaca agttcgatgg tattgcttct   2700
attcctactg aagcaattga tcctcgtctc cgtgctctat acatagaagc ggcagagcta   2760
gttggcatct atgggaagag ggatcaggag ctcatgagtt tgctctcctt ggagggcgat   2820
gatgcctcta ccaagaaact gaagaaggtc tccattgttg gatttggagg gttgggcaag   2880
accactcttg ccaaagcagt atacgagaag attaaaggtg attttgattg tcacgcattt   2940
gttcctgtcg ggcagaaccc tgacaagaag aaggttttta gggatatcct catggatctc   3000
agcaactcta actcagatct tgcattattg gatgaaaggc agcttatcaa caaacttcat   3060
aaatttctcg agaacaagag gtatgcatca cttacaatga aaatgccact tatcatatgt   3120
ttttcctatg tatcaatatc ttgtaacctt agtacctcgc gtcaaacggt ctggaatcat   3180
ttttttcatt aaggtcacct ttgctaacat acgtagtttt gcactaaact attaatattt   3240
gtaggtgcta aattttaaga ctatataagc aagtctctga acctcctctc ctttatgtaa   3300
atagattatt gtaactactt cttgttgcaa tcgttacagt ggctgaaatt tattgccata   3360
tttttaagaa atccacctca acatatcgta caatacatgc accaaagaca caaaatgata   3420
agcataatgt caattgtagc aaataataca ccaatacatg caccaaataa aactttacaa   3480
tattttactt caaatttctt tctttctctt aacccatcgc gttctaaaat aaagacttta   3540
aagtgcttat cttgcaccaa aggctagcca gtaattttcc tgaaatattg tatttaattt   3600
gattaatggc caaacaaaaa tttaatttgc tcttcactgt cacattctac ttttccttta   3660
tgcctctttg gaaacttact acctgcataa tgtgcacgga atgataatgc aatgcaataa   3720
gagtctccag gaggtttatt agcggccatt tagtaaattg gtgggccgat ctgtacccgg   3780
gtctttccag tagatgcacc taaccattgt aatatttgaa atgtcttcca aattggtact   3840
```

-continued

```
cgtctttcaa atagatctac ctaatcgtta tagctaatta attcttcttc tatgtatggc   3900
catcgatcta ccaattttct atttgtattt taccctttga atcttaaatt tgtattcatt   3960
ttgttcatta tctaattggc agttcataac gcatgcttct taaaagatca tattgcccag   4020
attcatacgt gtgctactta ttagtttgtt tgtgaacatg cacaatctag atgcatagtt   4080
ccacatatat attcacatgt cccatagctt tgccatatca acacacctta cactaatact   4140
ctcaactgac gtaggtacct tgtcataatt gatgatgtat gggatgaagg tttgtggaaa   4200
gacatcaacc ttgctttctc caacaggaac aatctaggca gtcggctaat catcacaacc   4260
cgcatttttg gtgtctccga gtcatgttgc tcatcggctg atgatccggt ttatgaaatt   4320
gaacctcttt ccatagatga ctccagcaag ctcttctata caagaatatt ctcggatagt   4380
ggatgcccaa aggaatttga acaagtgtct aaagatatat tgaagaaatg tggtggggta   4440
ccactagcca tcattactat tgctagtgct ttggctagtg gccagcaagt gaaaccaaag   4500
catgagtggg atattctact ccagtccctt ggctccggag taacaaaaga taacagtttg   4560
gttgagatgc ggagaatact atcattcagc tattataatc taccgtctca tctgaaaacc   4620
tgtctactgt acctatgtat atatccagaa gatagcatga ttcatagaga tagactcata   4680
tggaagtggg tggccgaagg atttgtccac catggagatc aagggaccag cctatttttg   4740
gtcggattaa actacttcaa ccagctcatt aatagaagta tgctccagcc aatatattcg   4800
gatatgggca acgtatatgc ttgccgtgta catgatatgg ttctggacct tatctgcaac   4860
ttgtcacatg aagcaaagtt tgttaatgta ttcgatggca ctgggaatat catgtcttca   4920
caaagtaatg ttcgccgctt gtcccttcag aataaaaatg aagatcatca agccaaacct   4980
ctcacaaata tcatgagtat ctcacaagtg aggtcaatta ctatctttcc acctgctgtc   5040
agtatcatgc cagccctgtc aaggtttgaa gttctacggg tacttgattt gtcggactgt   5100
aaccttgggg aaagtagcag cctgcagcct aacctcaagg gtgttggaca cttaattcac   5160
ctaaggtacc taggtctatc aggtaccaga attagtaaac tcccggctga gataggaacc   5220
ctgcagtttc tggaggtgtt ggatcttgga tacaatcatg agctagatga attgccttcc   5280
actcttttta aattgagaag attaatctac ctaaatgttt ctccctataa ggtggttcca   5340
actcctggtg tgttgcagaa tatgacatcc atagaagtgt tgagggggat ctttgtctct   5400
ctgaacatta ttgcacaaga gcttggcaaa ctggcaaggc tgagggagct tcagatttac   5460
ttcaaggatg gtagtttgga tttgtatgaa ggtttcgtga agtctctgtg caacttacat   5520
cacatcgaaa gcctaattgt tagttgcaat tctggagaaa catcttttga actgatggat   5580
ctcttgggag aacaatgggt gcctcctgta catctccgcg aatttgtgtc agaaatgccc   5640
agccaactct ctgcactgcg agggtggata aagagagacc cctcgcatct ctcgaacctc   5700
tccgagttaa tcctcccgac agtgaaggaa gtgcagcagg aggacgtgga aatcattggg   5760
gggttgctgt cccttcgccg tctgctcata gagagcaccc accaaacaca acggctgcta   5820
gtcatccgtg cagatgggtt ccgctgtatg gtagactttt acttgaattg tggatccgca   5880
acgcagataa tgtttgaatc aggagctttg ccgagggcgg aagaagtttg cttcagcctg   5940
ggcgtgcggg tggcgaaaga ggatggtaac cgtggtttcg acttgggcct gcaggggaac   6000
ctgctctccc ttcggcgggt ggtctgggtt aagatgtatt gtggtggagc gagggttggg   6060
gaggccaagg aagcgaaggc tgcggtgagg cacgcactcg aagaccatcc caaccatcct   6120
ccgattcaaa ttaacatgtt cccgcgtata gcagaaggta ctgacgctac acgcaactaa   6180
ttcctcgtgc acctacgaat gtgttctctc attagcgcct gaccttatta ctttctgcat   6240
```

```
tgatttgatc tctaaatctc ccaaggtgct caagatgacg atttaatgtg ttacccggtt   6300

ggaggaccga tttctgacgc agagtgactg acgttgcttc aggtgtgctc tcaatctata   6360

catatttact catcatatta ttctccacct ttttttccat ctctagagct cagcttgtca   6420

ttgcattgtt caattgtgct tctctagcag ctacggaaat tctgaacagg caaaggtaat   6480

tttacagaag tttctttggc ataagtatct gagaaaaatg cacttggcac aatttacctt   6540

ttcgcagtag aaaagagtca gtggatcata ccttcttaat tgttcgattg ctcgtaatac   6600

ttgggggcac tctatgattg ctgtgtgctt ttagttttga tatagttcct gttagcatgg   6660

acagactgtg tgattggttc atgaatttca gggtggttct aatgaggaaa tgatgcttgc   6720

ttcagaaata gtttccattt gtacctaagc tgtgtagttg gtaaagttgc attttggatg   6780

ttctgttggt atagcttaca gaagaaagac ttgcgttgtg caggtaccag gggcgcaggt   6840

tactgctagt ggcgtctgag atgtttcata aacgttgggt gggcaccggt catgcaaaaa   6900

attgaaggat aaaaaggttc cgagaggttg tgtgatgtgc tccttttaaa tggcagtcgc   6960

ttgcataaag agatgttgct tggtttttta gtaaagcgtt gtagtaagtt gctctgtttc   7020

ggctgagagc catcgttgtt gctgtctgtt acatcgaatg gctggctcat gtcatgttga   7080

tgtttttttt atctgaaccg gacaaacctg agggtgtagt atcatgtttg taatgactga   7140

aattctgggc tcacccgagc tccttaattc gtaaacaact gcgactcatt gttggattcc   7200

ttacttcaga aaatatttac ttgctctggc tcatacagct ctgcatgttt tgtagtggtt   7260

tgtcgctgtt taggtgctgc ttcagactcc tggtaccttt ggccgctgct gctactgcat   7320

gagctttgta tggcattgtt agtatagttt ggtgtcattg ggttttcgcc ccatggtgag   7380

tgtccattgc gcgcactcgc agcggtttcc tggcgataag ttgaacttga tctttctctt   7440

tcccacctcc taaacgtcta ttcagacttg tgtatatttg cattacgggg attacccgag   7500

ttcaaaaata aatattattt actagttctg ccaatgtgtt tccgttacat acaaataaaa   7560

gggtgcttcc agctacaagt atatttttga gaagggccat tgcaaaacga aatgaagccc   7620

aaattctacc aacatgtttc tgtcacatat acattaaaaa aacggtgtag atgtcccgtc   7680

aaaaaagggt gtatgtagga aaaggagttc gacgccgcca gctccctcct aatgaggtga   7740

gatgacaaag gagaaggtca ccgctcgagt tcctaatgag tag                     7783
```

```
<210> SEQ ID NO 6
<211> LENGTH: 961
<212> TYPE: PRT
<213> ORGANISM: Aegilops tauschii

<400> SEQUENCE: 6

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95
```

```
Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205

Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
            260                 265                 270

Lys Arg Tyr Leu Val Ile Ile Asp Asp Val Trp Asp Glu Gly Leu Trp
        275                 280                 285

Lys Asp Ile Asn Leu Ala Phe Ser Asn Arg Asn Asn Leu Gly Ser Arg
    290                 295                 300

Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
                325                 330                 335

Ser Ser Lys Leu Phe Tyr Thr Arg Ile Phe Ser Asp Ser Gly Cys Pro
            340                 345                 350

Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Phe Asp Gly Thr Gly Asn Ile Met Ser
```

```
        515                 520                 525

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asp Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Lys Val Val Pro Thr Pro Gly
            660                 665                 670

Val Leu Gln Asn Met Thr Ser Ile Glu Val Leu Arg Gly Ile Phe Val
        675                 680                 685

Ser Leu Asn Ile Ile Ala Gln Glu Leu Gly Lys Leu Ala Arg Leu Arg
    690                 695                 700

Glu Leu Gln Ile Tyr Phe Lys Asp Gly Ser Leu Asp Leu Tyr Glu Gly
705                 710                 715                 720

Phe Val Lys Ser Leu Cys Asn Leu His His Ile Glu Ser Leu Ile Val
                725                 730                 735

Ser Cys Asn Ser Gly Glu Thr Ser Phe Glu Leu Met Asp Leu Leu Gly
            740                 745                 750

Glu Gln Trp Val Pro Pro Val His Leu Arg Glu Phe Val Ser His Met
        755                 760                 765

Pro Ser Gln Leu Ser Ala Leu Arg Gly Trp Ile Lys Arg Asp Pro Ser
    770                 775                 780

His Leu Ser Asn Leu Ser Glu Leu Ile Leu Pro Thr Val Lys Glu Val
785                 790                 795                 800

Gln Gln Glu Asp Val Glu Ile Ile Gly Gly Leu Leu Ser Leu Arg Arg
                805                 810                 815

Leu Trp Ile Lys Thr Thr His Gln Thr Gln Arg Leu Leu Val Ile Arg
            820                 825                 830

Ala Asp Gly Phe Arg Cys Met Val Asp Phe His Leu Asn Cys Gly Ser
        835                 840                 845

Ala Thr Gln Ile Met Phe Glu Ser Gly Ala Leu Pro Arg Ala Glu Glu
    850                 855                 860

Val Cys Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
                885                 890                 895

Val Trp Val Lys Met Tyr Cys Gly Gly Ala Arg Val Gly Glu Ala Lys
            900                 905                 910

Glu Ala Lys Ala Ala Val Arg His Ala Leu Glu Asp His Pro Asn His
        915                 920                 925

Pro Pro Ile Gln Ile Asn Met Phe Pro Arg Ile Ala Glu Gly Ala Gln
    930                 935                 940
```

Asp Asp Asp Leu Met Cys Tyr Pro Ala Gly Gly Pro Ile Ser Asp Ala
945 950 955 960

Glu

<210> SEQ ID NO 7
<211> LENGTH: 941
<212> TYPE: PRT
<213> ORGANISM: Aegilops tauschii

<400> SEQUENCE: 7

Met Asp Ile Val Thr Gly Ala Ile Ala Lys Leu Ile Pro Lys Leu Gly
1 5 10 15

Glu Leu Leu Val Gly Glu Tyr Lys Leu His Lys Gly Val Lys Lys Asn
20 25 30

Ile Glu Asp Leu Leu Lys Glu Leu Lys Thr Met Asn Ala Ala Leu Ile
35 40 45

Lys Ile Gly Glu Val Pro Pro Asp Gln Leu Asp Ser Gln Asp Lys Leu
50 55 60

Trp Ala Asp Glu Val Arg Glu Leu Ser Tyr Val Ile Glu Asp Ala Val
65 70 75 80

Asp Lys Phe Leu Val Arg Val His Gly Val Glu Pro Asp Asp Asn Thr
85 90 95

Asn Gly Phe Lys Gly Leu Met Lys Arg Thr Thr Lys Leu Leu Lys Lys
100 105 110

Val Val Asp Lys His Gly Ile Ala His Ala Ile Lys Asp Ile Lys Lys
115 120 125

Glu Leu Gln Glu Val Ala Ala Arg Arg Asp Arg Asn Lys Phe Asp Gly
130 135 140

Ile Ala Ser Ile Pro Thr Glu Ala Ile Asp Pro Arg Leu Arg Ala Leu
145 150 155 160

Tyr Ile Glu Ala Ala Glu Leu Val Gly Ile Tyr Gly Lys Arg Asp Gln
165 170 175

Glu Leu Met Ser Leu Leu Ser Leu Glu Gly Asp Asp Ala Ser Thr Lys
180 185 190

Lys Leu Lys Lys Val Ser Ile Val Gly Phe Gly Gly Leu Gly Lys Thr
195 200 205

Thr Leu Ala Lys Ala Val Tyr Glu Lys Ile Lys Gly Asp Phe Asp Cys
210 215 220

His Ala Phe Val Pro Val Gly Gln Asn Pro Asp Lys Lys Lys Val Phe
225 230 235 240

Arg Asp Ile Leu Met Asp Leu Ser Asn Ser Asn Ser Asp Leu Ala Leu
245 250 255

Leu Asp Glu Arg Gln Leu Ile Asn Lys Leu His Lys Phe Leu Glu Asn
260 265 270

Lys Arg Tyr Leu Val Ile Ile Asp Asp Val Trp Asp Glu Gly Leu Trp
275 280 285

Lys Asp Ile Asn Leu Ala Phe Ser Asn Arg Asn Asn Leu Gly Ser Arg
290 295 300

Leu Ile Ile Thr Thr Arg Ile Phe Gly Val Ser Glu Ser Cys Cys Ser
305 310 315 320

Ser Ala Asp Asp Pro Val Tyr Glu Ile Glu Pro Leu Ser Ile Asp Asp
325 330 335

Ser Ser Lys Leu Phe Tyr Thr Arg Ile Phe Ser Asp Ser Gly Cys Pro
340 345 350

```
Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Leu Asp Gly Thr Gly Asn Ile Met Ser
        515                 520                 525

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asp Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620

Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Lys Val Val Arg Thr Leu Gly
            660                 665                 670

Val Leu Gln Asn Met Thr Ser Ile Glu Val Leu Arg Gly Ile Phe Val
        675                 680                 685

Ser Leu Asn Ile Ile Ala Gln Glu Leu Gly Lys Leu Ala Arg Leu Arg
    690                 695                 700

Glu Leu Gln Ile Arg Phe Lys Asp Gly Ser Leu Asp Leu Tyr Glu Gly
705                 710                 715                 720

Phe Val Lys Ser Leu Cys Asn Leu His Gln Ile Glu Ser Leu Ile Ile
                725                 730                 735

Asp Cys Asn Ser Glu Glu Ala Ser Phe Glu Leu Met Asp Leu Leu Gly
            740                 745                 750

Glu Arg Trp Val Pro Pro Val His Leu Arg Glu Phe Val Ser Tyr Met
        755                 760                 765
```

```
Pro Ser Gln Leu Ser Ala Leu Arg Gly Trp Ile Lys Arg Asp Pro Ser
    770                 775                 780

His Leu Ser Asn Leu Ser Glu Leu Ile Leu Thr Ser Val Lys Glu Val
785                 790                 795                 800

Gln Gln Glu Asp Val Glu Ile Ile Gly Gly Leu Leu Ser Leu Arg Arg
                805                 810                 815

Leu Arg Ile Trp Ser Thr His Gln Thr Gln Arg Leu Leu Val Ile Arg
            820                 825                 830

Ala Asp Gly Phe Arg Cys Met Val Asp Phe Tyr Leu Asn Cys Arg Ser
        835                 840                 845

Ala Ala Gln Ile Lys Phe Glu Pro Gly Ala Leu Pro Arg Ala Glu Gly
    850                 855                 860

Val Val Phe Ser Leu Gly Val Arg Val Ala Lys Glu Asp Gly Asn Arg
865                 870                 875                 880

Gly Phe Asp Leu Gly Leu Gln Gly Asn Leu Leu Ser Leu Arg Arg Val
                885                 890                 895

Val Leu Val Lys Met Tyr Cys Gly Gly Ala Arg Val Gly Glu Ala Lys
            900                 905                 910

Glu Ala Glu Ala Ala Val Arg His Ala Leu Glu Asp His Pro Asn His
        915                 920                 925

Pro Pro Ile Glu Ile Asn Met Leu Pro His Ile Ala Lys
    930                 935                 940


<210> SEQ ID NO 8
<211> LENGTH: 712
<212> TYPE: PRT
<213> ORGANISM: Aegilops tauschii

<400> SEQUENCE: 8

Met Asp Ile Val Thr Gly Ala Ile Ala Lys Leu Ile Pro Lys Leu Gly
1               5                   10                  15

Glu Leu Leu Val Gly Glu Tyr Lys Leu His Lys Gly Val Lys Lys Asn
            20                  25                  30

Ile Glu Asp Leu Leu Lys Glu Leu Lys Thr Met Asn Ala Ala Leu Ile
        35                  40                  45

Lys Ile Gly Glu Val Pro Pro Asp Gln Leu Asp Ser Gln Asp Lys Leu
    50                  55                  60

Trp Ala Asp Glu Val Arg Glu Leu Ser Tyr Val Ile Glu Asp Ala Val
65                  70                  75                  80

Asp Lys Phe Leu Val Arg Val His Gly Val Glu Pro Asp Asp Asn Thr
                85                  90                  95

Asn Gly Phe Lys Gly Leu Met Lys Arg Thr Thr Lys Leu Leu Lys Lys
            100                 105                 110

Val Val Asp Lys His Gly Ile Ala His Ala Ile Lys Asp Ile Lys Lys
        115                 120                 125

Glu Leu Gln Glu Val Ala Ala Arg Arg Asp Arg Asn Lys Phe Asp Gly
    130                 135                 140

Ile Ala Ser Ile Pro Thr Glu Ala Ile Asp Pro Arg Leu Arg Ala Leu
145                 150                 155                 160

Tyr Ile Glu Ala Ala Glu Leu Val Gly Ile Tyr Gly Lys Arg Asp Gln
                165                 170                 175

Glu Leu Met Ser Leu Leu Ser Leu Glu Gly Asp Asp Ala Ser Thr Lys
            180                 185                 190

Lys Leu Lys Lys Val Ser Ile Val Gly Phe Gly Gly Leu Gly Lys Thr
        195                 200                 205
```

```
Thr Leu Ala Lys Ala Val Tyr Glu Lys Ile Lys Gly Asp Phe Asp Cys
    210                 215                 220

His Ala Phe Val Pro Val Gly Gln Asn Pro Asp Lys Lys Lys Val Phe
225                 230                 235                 240

Arg Asp Ile Leu Met Asp Leu Ser Asn Ser Asn Ser Asp Leu Ala Leu
                245                 250                 255

Leu Asp Glu Arg Gln Leu Ile Asn Lys Leu His Lys Phe Leu Glu Asn
            260                 265                 270

Lys Arg Tyr Leu Val Ile Ile Asp Asp Val Trp Asp Glu Gly Leu Trp
        275                 280                 285

Lys Asp Ile Asn Leu Ala Phe Ser Asn Arg Asn Asn Leu Gly Ser Arg
    290                 295                 300

Leu Ile Ile Thr Thr Arg Ile Phe Gly Val Ser Glu Ser Cys Cys Ser
305                 310                 315                 320

Ser Ala Asp Asp Pro Val Tyr Glu Ile Glu Pro Leu Ser Ile Asp Asp
                325                 330                 335

Ser Ser Lys Leu Phe Tyr Thr Arg Ile Phe Ser Asp Ser Gly Cys Pro
            340                 345                 350

Lys Glu Phe Glu Gln Val Ser Lys Asp Ile Leu Lys Lys Cys Gly Gly
        355                 360                 365

Val Pro Leu Ala Ile Ile Thr Ile Ala Ser Ala Leu Ala Ser Gly Gln
    370                 375                 380

Gln Val Lys Pro Lys His Glu Trp Asp Ile Leu Leu Gln Ser Leu Gly
385                 390                 395                 400

Ser Gly Val Thr Lys Asp Asn Ser Leu Val Glu Met Arg Arg Ile Leu
                405                 410                 415

Ser Phe Ser Tyr Tyr Asn Leu Pro Ser His Leu Lys Thr Cys Leu Leu
            420                 425                 430

Tyr Leu Cys Ile Tyr Pro Glu Asp Ser Met Ile His Arg Asp Arg Leu
        435                 440                 445

Ile Trp Lys Trp Val Ala Glu Gly Phe Val His His Gly Asp Gln Gly
    450                 455                 460

Thr Ser Leu Phe Leu Val Gly Leu Asn Tyr Phe Asn Gln Leu Ile Asn
465                 470                 475                 480

Arg Ser Met Leu Gln Pro Ile Tyr Ser Asp Met Gly Asn Val Tyr Ala
                485                 490                 495

Cys Arg Val His Asp Met Val Leu Asp Leu Ile Cys Asn Leu Ser His
            500                 505                 510

Glu Ala Lys Phe Val Asn Val Phe Asp Gly Thr Gly Asn Ile Met Ser
        515                 520                 525

Ser Gln Ser Asn Val Arg Arg Leu Ser Leu Gln Asn Lys Asn Glu Asp
    530                 535                 540

His Gln Ala Lys Pro Leu Thr Asn Ile Met Ser Ile Ser Gln Val Arg
545                 550                 555                 560

Ser Ile Thr Ile Phe Pro Pro Ala Val Ser Ile Met Pro Ala Leu Ser
                565                 570                 575

Arg Phe Glu Val Leu Arg Val Leu Asp Leu Ser Asp Cys Asn Leu Gly
            580                 585                 590

Glu Ser Ser Ser Leu Gln Pro Asn Leu Lys Gly Val Gly His Leu Ile
        595                 600                 605

His Leu Arg Tyr Leu Gly Leu Ser Gly Thr Arg Ile Ser Lys Leu Pro
    610                 615                 620
```

```
Ala Glu Ile Gly Thr Leu Gln Phe Leu Glu Val Leu Asp Leu Gly Tyr
625                 630                 635                 640

Asn His Glu Leu Asp Glu Leu Pro Ser Thr Leu Phe Lys Leu Arg Arg
                645                 650                 655

Leu Ile Tyr Leu Asn Val Ser Pro Tyr Glu Val Val Pro Thr Pro Gly
            660                 665                 670

Val Leu Gln Asn Met Thr Ser Ile Glu Val Leu Arg Gly Ile Phe Val
        675                 680                 685

Ser Glu His Tyr Cys Thr Arg Ala Trp Gln Thr Gly Lys Ala Glu Gly
    690                 695                 700

Ala Ser Asp Leu Leu Gln Gly Trp
705                 710
```

<210> SEQ ID NO 9
<211> LENGTH: 2886
<212> TYPE: DNA
<213> ORGANISM: Aegilops tauschii

<400> SEQUENCE: 9

```
atggatattg tcacgggtgc cattgccaag ctgatcccca agctgggaga actgcttgtg     60

ggggagtaca aactgcacaa gggcgtcaag aaaaatatcg aggacctcct gaaagagctc    120

aagaccatga acgctgcgct catcaagatt ggtgaggtgc cgccggacca gctcgacagc    180

caagacaagc tttgggccga tgaggtcaga gagctctcct acgtcattga ggatgcggtg    240

gacaagttcc tcgtacgggt ccatggcgtt gagcccgacg acaacaccaa cggattcaag    300

gggctcatga agaggaccac caagttgttg aagaaagtcg tggataagca tggaatagct    360

cacgcgatca aggacatcaa gaaggaactc caggaggtgg ctgctaggcg tgacaggaac    420

aagttcgatg gtattgcttc tattcctact gaagcaattg atcctcgtct ccgtgctcta    480

tacatagaag cggcagagct agttggcatc tatgggaaga gggatcagga gctcatgagt    540

ttgctctcct tggagggcga tgatgcctct accaagaaac tgaagaaggt ctccattgtt    600

ggatttggag ggttgggcaa gaccactctt gccaaagcag tatacgagaa gattaaaggt    660

gattttgatt gtcacgcatt tgttcctgtc gggcagaacc ctgacaagaa gaaggttttt    720

agggatatcc tcatggatct cagcaactct aactcagatc ttgcattatt ggatgaaagg    780

cagcttatca acaaacttca taaatttctc gagaacaaga ggtaccttgt cataattgat    840

gatgtatggg atgaaggttt gtggaaagac atcaaccttg ctttctccaa caggaacaat    900

ctaggcagtc ggctaatcat cacaacccgc atttttggtg tctccgagtc atgttgctca    960

tcggctgatg atccggttta tgaaattgaa cctctttcca tagatgactc cagcaagctc   1020

ttctatacaa gaatattctc ggatagtgga tgcccaaagg aatttgaaca agtgtctaaa   1080

gatatattga agaaatgtgg tggggtacca ctagccatca ttactattgc tagtgctttg   1140

gctagtggcc agcaagtgaa accaaagcat gagtgggata ttctactcca gtcccttggc   1200

tccggagtaa caaaagataa cagtttggtt gagatgcgga gaatactatc attcagctat   1260

tataatctac cgtctcatct gaaaacctgt ctactgtacc tatgtatata tccagaagat   1320

agcatgattc atagagatag actcatatgg aagtgggtgg ccgaaggatt tgtccaccat   1380

ggagatcaag ggaccagcct atttttggtc ggattaaact acttcaacca gctcattaat   1440

agaagtatgc tccagccaat atattcggat atgggcaacg tatatgcttg ccgtgtacat   1500

gatatggttc tggaccttat ctgcaacttg tcacatgaag caaagtttgt taatgtattc   1560

gatggcactg ggaatatcat gtcttcacaa agtaatgttc gccgcttgtc ccttcagaat   1620
```

aaaaatgaag atcatcaagc caaacctctc acaaatatca tgagtatctc acaagtgagg 1680
tcaattacta tctttccacc tgctgtcagt atcatgccag ccctgtcaag gtttgaagtt 1740
ctacgggtac ttgatttgtc ggactgtaac cttggggaaa gtagcagcct gcagcctaac 1800
ctcaagggtg ttggacactt aattcaccta aggtacctag gtctatcagg taccagaatt 1860
agtaaactcc cggctgagat aggaaccctg cagtttctgg aggtgttgga tcttggatac 1920
aatcatgagc tagatgaatt gccttccact ctttttaaat tgagaagatt aatctaccta 1980
aatgtttctc cctataaggt ggttccaact cctggtgtgt tgcagaatat gacatccata 2040
gaagtgttga gggggatctt tgtctctctg aacattattg cacaagagct tggcaaactg 2100
gcaaggctga gggagcttca gatttacttc aaggatggta gtttggattt gtatgaaggt 2160
ttcgtgaagt ctctgtgcaa cttacatcac atcgaaagcc taattgttag ttgcaattct 2220
ggagaaacat cttttgaact gatggatctc ttgggagaac aatgggtgcc tcctgtacat 2280
ctccgcgaat ttgtgtcaca catgcccagc caactctctg cactgcgagg gtggataaag 2340
agagacccct cgcatctctc gaacctctcc gagttaatcc tcccgacagt gaaggaagtg 2400
cagcaggagg acgtggaaat cattgggggg ttgctgtccc ttcgacgtct ctggataaag 2460
accacccacc aaacacaacg gctgctagtc atccgtgcag atgggttccg ctgtatggta 2520
gactttcact tgaattgtgg atccgcaacg cagataatgt ttgaatcagg agctttgccg 2580
agggcggaag aagtttgctt cagcctgggc gtgcgggtgg cgaaagagga tggtaaccgt 2640
ggtttcgact tgggcctgca ggggaacctg ctctcccttc ggcgggtggt ctgggttaag 2700
atgtattgtg gtggagcgag ggttggggag gccaaggaag cgaaggctgc ggtgaggcac 2760
gcactcgaag accatcccaa ccatcctccg attcaaatta acatgttccc gcgtatagca 2820
gaaggtgctc aagatgacga tttaatgtgt tacccggctg gaggaccgat ttctgacgca 2880
gagtga 2886

<210> SEQ ID NO 10
<211> LENGTH: 2824
<212> TYPE: DNA
<213> ORGANISM: Aegilops tauschii

<400> SEQUENCE: 10
atggatattg tcacgggtgc cattgccaag ctgatcccca agctgggaga actgcttgtg 60
ggggagtaca aactgcacaa gggcgtcaag aaaaatatcg aggacctcct gaaagagctc 120
aagaccatga acgctgcgct catcaagatt ggtgaggtgc cgccggacca gctcgacagc 180
caagacaagc tttgggccga tgaggtcaga gagctctcct acgtcattga ggatgcggtg 240
gacaagttcc tcgtacgggt ccatggcgtt gagcccgacg acaacaccaa cggattcaag 300
gggctcatga agaggaccac caagttgttg aagaaagtcg tggataagca tggaatagct 360
cacgcgatca aggacatcaa gaaggaactc caggaggtgg ctgctaggcg tgacaggaac 420
aagttcgatg gtattgcttc tattcctact gaagcaattg atcctcgtct ccgtgctcta 480
tacatagaag cggcagagct agttggcatc tatgggaaga gggatcagga gctcatgagt 540
ttgctctcct tggagggcga tgatgcctct accaagaaac tgaagaaggt ctccattgtt 600
ggatttggag ggttgggcaa gaccactctt gccaaagcag tatacgagaa gattaaaggt 660
gattttgatt gtcacgcatt tgttcctgtc gggcagaacc ctgacaagaa gaaggttttt 720
agggatatcc tcatggatct cagcaactct aactcagatc ttgcattatt ggatgaaagg 780
cagcttatca acaaacttca taaatttctc gagaacaaga ggtaccttgt cataattgat 840
gatgtatggg atgaaggttt gtggaaagac atcaaccttg ctttctccaa caggaacaat 900
ctaggcagtc ggctaatcat cacaacccgc atttttggtg tctccgagtc atgttgctca 960
tcggctgatg atccggttta tgaaattgaa cctctttcca tagatgactc cagcaagctc 1020
ttctatacaa gaatattctc ggatagtgga tgcccaaagg aatttgaaca agtgtctaaa 1080
gatatattga agaaatgtgg tggggtacca ctagccatca ttactattgc tagtgctttg 1140
gctagtggcc agcaagtgaa accaaagcat gagtgggata ttctactcca gtcccttggc 1200
tccggagtaa caaaagataa cagtttggtt gagatgcgga gaatactatc attcagctat 1260
tataatctac cgtctcatct gaaaacctgt ctactgtacc tatgtatata tccagaagat 1320
agcatgattc atagagatag actcatatgg aagtgggtgg ccgaaggatt tgtccaccat 1380
ggagatcaag ggaccagcct atttttggtc ggattaaact acttcaacca gctcattaat 1440
agaagtatgc tccagccaat atattcggat atgggcaacg tatatgcttg ccgtgtacat 1500
gatatggttc tggaccttat ctgcaacttg tcacatgaag caaagtttgt taatgtattg 1560
gatggcactg ggaatatcat gtcttcacaa agtaatgttc gccgcttgtc ccttcagaat 1620
aaaaatgaag atcatcaagc caaacctctc acaaatatca tgagtatctc acaagtgagg 1680
tcaattacta tctttccacc tgctgtcagt atcatgccag ccctgtcaag gtttgaagtt 1740
ctacgggtac ttgatttgtc ggactgtaac cttggggaaa gtagcagcct gcagcctaac 1800
ctcaagggtg ttggacactt aattcaccta aggtacctag gtctatcagg taccagaatt 1860
agtaaactcc cggctgagat aggaaccctg cagtttctgg aggtgttgga tcttggatac 1920
aatcatgagc tagatgaatt gccttccact ctttttaaat tgagaagatt aatctaccta 1980
aatgtttctc cctataaggt ggttcgaact cttggtgtgt tgcagaatat gacatccata 2040
gaagtgttga gggggatctt tgtctctctg aacattattg cacaagagct tggcaaactg 2100
gcaaggctga gggagcttca gattcgcttc aaggatggta gtttggattt gtatgaaggt 2160
ttcgtgaagt ctctgtgcaa cctacatcag atcgaaagtc taattattga ttgcaattcc 2220
gaagaagcat cttttgaact gatggatctc ttgggagaac gctgggtgcc tcctgtacat 2280
ctccgcgaat ttgtgtcata catgcccagc caactctctg cactgcgagg gtggataaag 2340
agagacccct cgcatctctc gaacctctcc gagttaatcc tcacgtcagt gaaggaagtg 2400
cagcaggagg acgtggaaat cattgggggg ttgctgtccc ttcgacgtct ccgcatatgg 2460
agcacccacc aaacacagcg gctgctagtc atccgtgcag atgggttccg ctgtatggtt 2520
gacttttact tgaactgtcg atcagcagcg cagataaagt ttgaaccggg agctttgcca 2580
agggcggaag gagttgtatt cagcctcggc gtgcgggtgg cgaaagagga tggtaaccgt 2640
ggtttcgact tgggcctcca ggggaacctg ctctcccttc ggcgggtggt cttggttaag 2700
atgtattgtg gtggagcgag ggttggggag gccaaggaag cggaggctgc ggtgaggcac 2760
gcactcgaag accatcccaa ccatcccccg attgaaatta acatgttgcc gcatatagca 2820
aaag 2824

<210> SEQ ID NO 11
<211> LENGTH: 2885
<212> TYPE: DNA
<213> ORGANISM: Aegilops tauschii

<400> SEQUENCE: 11
atggatattg tcacgggtgc cattgccaag ctgatcccca agctgggaga actgcttgtg 60

```
ggggagtaca aactgcacaa gggcgtcaag aaaaatatcg aggacctcct gaaagagctc    120
aagaccatga acgctgcgct catcaagatt ggtgaggtgc cgccggacca gctcgacagc    180
caagacaagc tttgggccga tgaggtcaga gagctctcct acgtcattga ggatgcggtg    240
gacaagttcc tcgtacgggt ccatggcgtt gagcccgacg acaacaccaa cggattcaag    300
gggctcatga agaggaccac caagttgttg aagaaagtcg tggataagca tggaatagct    360
cacgcgatca aggacatcaa gaaggaactc caggaggtgg ctgctaggcg tgacaggaac    420
aagttcgatg gtattgcttc tattcctact gaagcaattg atcctcgtct ccgtgctcta    480
tacatagaag cggcagagct agttggcatc tatgggaaga gggatcagga gctcatgagt    540
ttgctctcct tggagggcga tgatgcctct accaagaaac tgaagaaggt ctccattgtt    600
ggatttggag ggttgggcaa gaccactctt gccaaagcag tatacgagaa gattaaaggt    660
gattttgatt gtcacgcatt tgttcctgtc gggcagaacc ctgacaagaa gaaggttttt    720
agggatatcc tcatggatct cagcaactct aactcagatc ttgcattatt ggatgaaagg    780
cagcttatca acaaacttca taaatttctc gagaacaaga ggtaccttgt cataattgat    840
gatgtatggg atgaaggttt gtggaaagac atcaaccttg ctttctccaa caggaacaat    900
ctaggcagtc ggctaatcat cacaacccgc atttttggtg tctccgagtc atgttgctca    960
tcggctgatg atccggttta tgaaattgaa cctctttcca tagatgactc cagcaagctc   1020
ttctatacaa gaatattctc ggatagtgga tgcccaaagg aatttgaaca agtgtctaaa   1080
gatatattga agaaatgtgg tggggtacca ctagccatca ttactattgc tagtgctttg   1140
gctagtggcc agcaagtgaa accaaagcat gagtgggata ttctactcca gtcccttggc   1200
tccggagtaa caaaagataa cagtttggtt gagatgcgga gaatactatc attcagctat   1260
tataatctac cgtctcatct gaaaacctgt ctactgtacc tatgtatata tccagaagat   1320
agcatgattc atagagatag actcatatgg aagtgggtgg ccgaaggatt tgtccaccat   1380
ggagatcaag ggaccagcct atttttggtc ggattaaact acttcaacca gctcattaat   1440
agaagtatgc tccagccaat atattcggat atgggcaacg tatatgcttg ccgtgtacat   1500
gatatggttc tggaccttat ctgcaacttg tcacatgaag caaagtttgt taatgtattc   1560
gatggcactg ggaatatcat gtcttcacaa agtaatgttc gccgcttgtc ccttcagaat   1620
aaaaatgaag atcatcaagc caaacctctc acaaatatca tgagtatctc acaagtgagg   1680
tcaattacta tctttccacc tgctgtcagt atcatgccag ccctgtcaag gtttgaagtt   1740
ctacgggtac ttgatttgtc ggactgtaac cttggggaaa gtagcagcct gcagcctaac   1800
ctcaagggtg ttggacactt aattcaccta aggtacctag gtctatcagg taccagaatt   1860
agtaaactcc cggctgagat aggaaccctg cagtttctgg aggtgttgga tcttggatac   1920
aatcatgagc tagatgaatt gccttccact ctttttaaat tgagaagatt aatctaccta   1980
aatgtttctc cctatgaggt ggttccaact cctggtgtgt tgcagaatat gacatccata   2040
gaagtgttga gggggatctt tgtctctgaa cattattgca caagagcttg gcaaactggc   2100
aaggctgagg gagcttcaga tttacttcaa ggatggtagt ttggatttgt atgaaggttt   2160
cgtgaagtct ctgtgcaact tacatcacat cgaaagccta attgttagtt gcaattctgg   2220
agaaacatct tttgaactga tggatctctt gggagaacaa tgggtgcctc ctgtacatct   2280
ccgcgaattt gtgtcacaca tgcccagcca actctctgca ctgcgagggt ggataaagag   2340
agacccctcg catctctcga acctctccga gttaatcctc acgtcagtga aggaagtgca   2400
```

```
gcacgaggac gtggaaatca ttggggggtt gctgtccctt cgacgtctcc gcatatggag   2460

cacccaccaa acacaacggc tgctagtcat ccgtgcagat gggttccgct gtatggttga   2520

cttttacttg aactgtcgat cagcaacgca gataatgttt gaattgggag ctttgccgag   2580

ggcggaatca gttacgttca gccttggtgt acgggtggcg gaagaggatg gtaactgtga   2640

cttcgacttg ggccttcagg ggaacatgct ctcccttcgg cggcgtgtca gggtttggat   2700

gtattgtcgt ggagcgaggg ttggggaggc caaggaagcg aaggctgcgg tgaggcacgc   2760

actcgacgcc catcccaacc atcccccgac tgaaattgac atgttcccgc aaatagcaga   2820

aggtgctcaa gatgacgatt taatgtgatt acccggttgg aggaccgatt tctgacgcag   2880

agtga                                                               2885
```

<210> SEQ ID NO 12
<211> LENGTH: 4386
<212> TYPE: DNA
<213> ORGANISM: Aegilops tauschii

<400> SEQUENCE: 12

```
gggcttggtc cagatcccca cattcatcga tttggcttgc caactcagtt ccaccagagc     60

ttggattgtg ttacagatcc ctaaattcat cgatttgcag gtttcagctg attgatcaag    120

agagctctca tggatattgt cacgggtgcc attgccaagc tgatccccaa gctgggagaa    180

ctgcttgtgg gggagtacaa actgcacaag ggcgtcaaga aaaatatcga ggacctcctg    240

aaagagctca agaccatgaa cgctgcgctc atcaagattg gtgaggtgcc gccggaccag    300

ctcgacagcc aagacaagct ttgggccgat gaggtcagag agctctccta cgtcattgag    360

gatgcggtgg acaagttcct cgtacgggtc catggcgttg agcccgacga caacaccaac    420

ggattcaagg ggctcatgaa gaggaccacc aagttgttga agaaagtcgt ggataagcat    480

ggaatagctc acgcgatcaa ggacatcaag aaggaactcc aggaggtggc tgctaggcgt    540

gacaggaaca agttcgatgg tattgcttct attcctactg aagcaattga tcctcgtctc    600

cgtgctctat acatagaagc ggcagagcta gttggcatct atgggaagag ggatcaggag    660

ctcatgagtt tgctctcctt ggagggcgat gatgcctcta ccaagaaact gaagaaggtc    720

tccattgttg gatttggagg gttgggcaag accactcttg ccaaagcagt atacgagaag    780

attaaaggtg attttgattg tcacgcattt gttcctgtcg ggcagaaccc tgacaagaag    840

aaggttttta gggatatcct catggatctc agcaactcta actcagatct tgcattattg    900

gatgaaaggc agcttatcaa caaacttcat aaatttctcg agaacaagag gtatgcatca    960

cttacaatga aaatgccact tatcatatgt ttttcctatg tatcaatatc ttgtaacctt   1020

agtacctcgc gtcaaacggt ctggaatcat ttttttcatt aaggtcacct ttgctaacat   1080

acgtagtttt gcactaaact attaatattt gtaggtgcta aattttaaga ctatataagc   1140

aagtctctga acctcctctc ctttatgtaa atagattatt gtaactactt cttgttgcaa   1200

tcgttacagt ggctgaaatt tattgccata tttttaagaa atccacctca acatatcgta   1260

caatacatgc accaaagaca caaaatgata agcataatgt caattgtagc aaataataca   1320

ccaatacatg caccaaataa aactttacaa tattttactt caaatttctt tctttctctt   1380

aacccatcgc gttctaaaat aaagacttta aagtgcttat cttgcaccaa aggctagcca   1440

gtaattttcc tgaaatattg tatttaattt gattaatggc caaacaaaaa tttaatttgc   1500

tcttcactgt cacattctac ttttccttta tgcctctttg gaaacttact acctgcataa   1560

tgtgcacgga atgataatgc aatgcaataa gagtctccag gaggtttatt agcggccatt   1620
```

```
tagtaaattg gtgggccgat ctgtacccgg gtctttccag tagatgcacc taaccattgt   1680
aatatttgaa atgtcttcca aattggtact cgtctttcaa atagatctac ctaatcgtta   1740
tagctaatta attcttcttc tatgtatggc catcgatcta ccaattttct atttgtattt   1800
taccctttga atcttaaatt tgtattcatt ttgttcatta tctaattggc agttcataac   1860
gcatgcttct taaaagatca tattgcccag attcatacgt gtgctactta ttagtttgtt   1920
tgtgaacatg cacaatctag atgcatagtt ccacatatat attcacatgt cccatagctt   1980
tgccatatca acacacctta cactaatact ctcaactgac gtaggtacct tgtcataatt   2040
gatgatgtat gggatgaagg tttgtggaaa gacatcaacc ttgctttctc caacaggaac   2100
aatctaggca gtcggctaat catcacaacc cgcatttttg gtgtctccga gtcatgttgc   2160
tcatcggctg atgatccggt ttatgaaatt gaacctcttt ccatagatga ctccagcaag   2220
ctcttctata caagaatatt ctcggatagt ggatgcccaa aggaatttga acaagtgtct   2280
aaagatatat tgaagaaatg tggtggggta ccactagcca tcattactat tgctagtgct   2340
ttggctagtg gccagcaagt gaaaccaaag catgagtggg atattctact ccagtccctt   2400
ggctccggag taacaaaaga taacagtttg gttgagatgc ggagaatact atcattcagc   2460
tattataatc taccgtctca tctgaaaacc tgtctactgt acctatgtat atatccagaa   2520
gatagcatga ttcatagaga tagactcata tggaagtggg tggccgaagg atttgtccac   2580
catggagatc aagggaccag cctatttttg gtcggattaa actacttcaa ccagctcatt   2640
aatagaagta tgctccagcc aatatattcg gatatgggca acgtatatgc ttgccgtgta   2700
catgatatgg ttctggacct tatctgcaac ttgtcacatg aagcaaagtt tgttaatgta   2760
ttcgatggca ctgggaatat catgtcttca caaagtaatg ttcgccgctt gtcccttcag   2820
aataaaaatg aagatcatca agccaaacct ctcacaaata tcatgagtat ctcacaagtg   2880
aggtcaatta ctatctttcc acctgctgtc agtatcatgc cagccctgtc aaggtttgaa   2940
gttctacggg tacttgattt gtcgaactgt aaccttgggg aaagtagcag cctgcagcct   3000
aacctcaagg gtgttggaca cttaattcac ctaaggtacc taggtctatc aggtaccaga   3060
attagtaaac tcccggctga gataggaacc ctgcagtttc tggaggtgtt ggatcttgga   3120
tacaatcatg agctagatga attgccttcc actcttttta aattgagaag attaatctac   3180
ctaaatgttt ctccctataa ggtggttcca actcctggtg tgttgcagaa tatgacatcc   3240
atagaagtgt tgagggggat ctttgtctct ctgaacatta ttgcacaaga gcttggcaaa   3300
ctggcaaggc tgagggagct tcagatttac ttcaaggatg gtagtttgga tttgtatgaa   3360
ggtttcgtga agtctctgtg caacttacat cacatcgaaa gcctaattgt tagttgcaat   3420
tctggagaaa catcttttga actgatggat ctcttgggag aacaatgggt gcctcctgta   3480
catctccgcg aatttgtgtc agaaatgccc agccaactct ctgcactgcg agggtggata   3540
aagagagacc cctcgcatct ctcgaacctc tccgagttaa tcctcccgac agtgaaggaa   3600
gtgcagcagg aggacgtgga aatcattggg gggttgctgt cccttcgccg tctgctcata   3660
gagagcaccc accaaacaca acggctgcta gtcatccgtg cagatgggtt ccgctgtatg   3720
gtagactttt acttgaattg tggatccgca acgcagataa tgtttgaatc aggagctttg   3780
ccgagggcgg aagaagtttg cttcagcctg ggcgtgcggg tggcgaaaga ggatggtaac   3840
cgtggtttcg acttgggcct gcaggggaac ctgctctccc ttcggcgggt ggtctgggtt   3900
aagatgtatt gtggtggagc gagggttggg gaggccaagg aagcgaaggc tgcggtgagg   3960
```

```
cacgcactcg aagaccatcc caaccatcct ccgattcaaa ttaacatgtt cccgcgtata   4020

gcagaaggta ctgacgctac acgcaactaa ttcctcgtgc acctacgaat gtgttctctc   4080

attagcgcct gaccttatta ctttctgcat tgatttgatc tctaaatctc ccaaggtgct   4140

caagatgacg atttaatgtg ttacccggtt ggaggaccga tttctgacgc agagtgactg   4200

acgttgcttc aggtgtgctc tcaatctata catatttact catcatatta ttctccacct   4260

ttttttccat ctctagagct cagcttgtca ttgcattgtt caattgtgct tctctagcag   4320

ctacggaaat tctgaacagg caaaggtaat tttacagaag tttctttggc ataagtatct   4380

gagaaa                                                              4386


<210> SEQ ID NO 13
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 13

ttcaagatgt caaattttaa aagggc                                          26


<210> SEQ ID NO 14
<211> LENGTH: 23
<212> TYPE: DNA
<213> ORGANISM: Artificial Sequence
<220> FEATURE:
<223> OTHER INFORMATION: oligunucleotide primer

<400> SEQUENCE: 14

ctactcatta ggaactcgag cgg                                             23


<210> SEQ ID NO 15
<211> LENGTH: 17
<212> TYPE: DNA
<213> ORGANISM: Artificial Sequence
<220> FEATURE:
<223> OTHER INFORMATION: oligonucleotide primer AtM1 F1 R1 (forward)

<400> SEQUENCE: 15

ctgcgcgcgt ggttggc                                                    17


<210> SEQ ID NO 16
<211> LENGTH: 19
<212> TYPE: DNA
<213> ORGANISM: Artificial Sequence
<220> FEATURE:
<223> OTHER INFORMATION: oligonucleotide primer AtM1 F2 R2 (forward)

<400> SEQUENCE: 16

gatcggaatc ggatagggc                                                  19


<210> SEQ ID NO 17
<211> LENGTH: 21
<212> TYPE: DNA
<213> ORGANISM: Artificial Sequence
<220> FEATURE:
<223> OTHER INFORMATION: oligonucleotide primer AtM1 F3 R3 (forward)

<400> SEQUENCE: 17

agcagaatat actcgaaagg g                                               21


<210> SEQ ID NO 18
<211> LENGTH: 23
```

<212> TYPE: DNA
<213> ORGANISM: Artificial Sequence
<220> FEATURE:
<223> OTHER INFORMATION: oligonucleotide primer AtM1 F4 R4 (forward)

<400> SEQUENCE: 18
ttaatctacc taaatgtttc tcc 23

<210> SEQ ID NO 19
<211> LENGTH: 20
<212> TYPE: DNA
<213> ORGANISM: Artificial Sequence
<220> FEATURE:
<223> OTHER INFORMATION: oligonucleotide primer AtM2 F1 R1 (forward)

<400> SEQUENCE: 19
tcttcttctt ccacactggg 20

<210> SEQ ID NO 20
<211> LENGTH: 21
<212> TYPE: DNA
<213> ORGANISM: Artificial Sequence
<220> FEATURE:
<223> OTHER INFORMATION: oligonucleotide primer AtM2 F2 R2 (forward)

<400> SEQUENCE: 20
agctttgtac gcagaagcaa c 21

<210> SEQ ID NO 21
<211> LENGTH: 21
<212> TYPE: DNA
<213> ORGANISM: Artificial Sequence
<220> FEATURE:
<223> OTHER INFORMATION: oligonusleotide primer AtM2 F3 R3 (forward)

<400> SEQUENCE: 21
cctagagaac aaaaggtatg c 21

<210> SEQ ID NO 22
<211> LENGTH: 24
<212> TYPE: DNA
<213> ORGANISM: Artificial Sequence
<220> FEATURE:
<223> OTHER INFORMATION: oligonucleotide primer AtM2 F4 R4 (forward)

<400> SEQUENCE: 22
tttattcaga ttgtttatca tctg 24

<210> SEQ ID NO 23
<211> LENGTH: 21
<212> TYPE: DNA
<213> ORGANISM: Artificial Sequence
<220> FEATURE:
<223> OTHER INFORMATION: oligonucleotide primer AtM2 F5 R5 (forward)

<400> SEQUENCE: 23
tccagaagat agcatgattg c 21

<210> SEQ ID NO 24
<211> LENGTH: 22
<212> TYPE: DNA
<213> ORGANISM: Artificial Sequence
<220> FEATURE:
<223> OTHER INFORMATION: oligonucleotide primer AtM2 F6 R6 (forward)

<400> SEQUENCE: 24
tgttggatct tggagacaat ta 22

<210> SEQ ID NO 25
<211> LENGTH: 21
<212> TYPE: DNA
<213> ORGANISM: Artificial Sequence
<220> FEATURE:
<223> OTHER INFORMATION: oligonucleotide primer AtM2 F7 R7 (forward)

<400> SEQUENCE: 25
gaagtagtta ggttcagcct g 21

<210> SEQ ID NO 26
<211> LENGTH: 20
<212> TYPE: DNA
<213> ORGANISM: Artificial Sequence
<220> FEATURE:
<223> OTHER INFORMATION: oligonucleotide primer AtM3 F1 R1 (forward)

<400> SEQUENCE: 26
catatggatg tgaaggaggc 20

<210> SEQ ID NO 27
<211> LENGTH: 21
<212> TYPE: DNA
<213> ORGANISM: Artificial Sequence
<220> FEATURE:
<223> OTHER INFORMATION: oligonucleotide primer AtM3F2 R2 (forward)

<400> SEQUENCE: 27
ggctttgtac acagaagcta c 21

<210> SEQ ID NO 28
<211> LENGTH: 23
<212> TYPE: DNA
<213> ORGANISM: Artificial Sequence
<220> FEATURE:
<223> OTHER INFORMATION: oligonucleotide primer AtM3 F3 R3 (forward)

<400> SEQUENCE: 28
atccaaacat tttacatttc acc 23

<210> SEQ ID NO 29
<211> LENGTH: 23
<212> TYPE: DNA
<213> ORGANISM: Artificial Sequence
<220> FEATURE:
<223> OTHER INFORMATION: oligonucleotide primer AtM3 F4 R4 (forward)

<400> SEQUENCE: 29
atttattctt tttttggagg gca 23

<210> SEQ ID NO 30
<211> LENGTH: 22
<212> TYPE: DNA
<213> ORGANISM: Artificial Sequence
<220> FEATURE:
<223> OTHER INFORMATION: oligonucleotide primer AtM3 F5 R5 (forward)

<400> SEQUENCE: 30
atccagaaga tagcaagatt ga 22

<210> SEQ ID NO 31
<211> LENGTH: 21
<212> TYPE: DNA
<213> ORGANISM: Artificial Sequence
<220> FEATURE:
<223> OTHER INFORMATION: oligonucleotide primer AtM3 F6 R6 (forward)

<400> SEQUENCE: 31
ggaggtgttg gatattggaa g 21

<210> SEQ ID NO 32
<211> LENGTH: 22
<212> TYPE: DNA
<213> ORGANISM: Artificial Sequence
<220> FEATURE:
<223> OTHER INFORMATION: oligonucleotide primer AtM3 F7 R7 (forward)

<400> SEQUENCE: 32
ggaaaaagtt gatttcagcc tt 22

<210> SEQ ID NO 33
<211> LENGTH: 18
<212> TYPE: DNA
<213> ORGANISM: Artificial Sequence
<220> FEATURE:
<223> OTHER INFORMATION: oligonucleotide primer AtM4F1R1 (forward)

<400> SEQUENCE: 33
gggcttggtc cagatccc 18

<210> SEQ ID NO 34
<211> LENGTH: 24
<212> TYPE: DNA
<213> ORGANISM: Artificial Sequence
<220> FEATURE:
<223> OTHER INFORMATION: oligonucleotide primer AtM4F2R2 (forward)

<400> SEQUENCE: 34
ccataagaga atatttcctg acgc 24

<210> SEQ ID NO 35
<211> LENGTH: 20
<212> TYPE: DNA
<213> ORGANISM: Artificial Sequence
<220> FEATURE:
<223> OTHER INFORMATION: oligonucleotide primer AtM5 F1 R1 (forward)

<400> SEQUENCE: 35
cttgccaact cagttccacc 20

<210> SEQ ID NO 36
<211> LENGTH: 22
<212> TYPE: DNA
<213> ORGANISM: Artificial Sequence
<220> FEATURE:
<223> OTHER INFORMATION: oligonucleotide primer AtM5 F2 R2 (forward)

<400> SEQUENCE: 36
catatcgtac aatacatgca cc 22

<210> SEQ ID NO 37
<211> LENGTH: 21
<212> TYPE: DNA
<213> ORGANISM: Artificial Sequence
<220> FEATURE:
<223> OTHER INFORMATION: oligonucleotide primer AtM5 F3 R3 (forward)

<400> SEQUENCE: 37
atgctccagc caatatattc g 21

<210> SEQ ID NO 38
<211> LENGTH: 25
<212> TYPE: DNA
<213> ORGANISM: Artificial Sequence
<220> FEATURE:
<223> OTHER INFORMATION: oligonucleotide primer AtM6 F1 R1 (forward)

<400> SEQUENCE: 38
cttggatcaa tgttattact tctcc 25

<210> SEQ ID NO 39
<211> LENGTH: 22
<212> TYPE: DNA
<213> ORGANISM: Artificial Sequence
<220> FEATURE:
<223> OTHER INFORMATION: oligonucleotide primer AtM7F1R1 (forward)

<400> SEQUENCE: 39
gttgaactat ctttcgaact cg 22

<210> SEQ ID NO 40
<211> LENGTH: 21
<212> TYPE: DNA
<213> ORGANISM: Artificial Sequence
<220> FEATURE:
<223> OTHER INFORMATION: oligonucleotide primer AtM8F1R1 (forward)

<400> SEQUENCE: 40
gggtcctgta cattccctcg c 21

<210> SEQ ID NO 41
<211> LENGTH: 21
<212> TYPE: DNA
<213> ORGANISM: Artificial Sequence
<220> FEATURE:
<223> OTHER INFORMATION: oligonucleotide primer AtM1 F1 R1 (reverse)

<400> SEQUENCE: 41
gatcgataac aactgcttcc c 21

<210> SEQ ID NO 42
<211> LENGTH: 22
<212> TYPE: DNA
<213> ORGANISM: Artificial Sequence
<220> FEATURE:
<223> OTHER INFORMATION: oligonucleotide primer AtM1 F2 R2 (reverse)

<400> SEQUENCE: 42
aatggttagg tagatctatt gg 22

<210> SEQ ID NO 43
<211> LENGTH: 18
<212> TYPE: DNA
<213> ORGANISM: Artificial Sequence
<220> FEATURE:
<223> OTHER INFORMATION: oligonucleotide primer AtM1 F3 R3 (reverse)

<400> SEQUENCE: 43
ctccctcagc cttgccag 18

<210> SEQ ID NO 44
<211> LENGTH: 20
<212> TYPE: DNA
<213> ORGANISM: Artificial Sequence
<220> FEATURE:
<223> OTHER INFORMATION: oligonucleotide primer AtM1 F4 R4 (reverse)

<400> SEQUENCE: 44
cagtgaaatt agcgtgcagc 20

<210> SEQ ID NO 45
<211> LENGTH: 21
<212> TYPE: DNA
<213> ORGANISM: Artificial Sequence
<220> FEATURE:
<223> OTHER INFORMATION: oligonucleotide primer AtM2 F1 R1 (reverse)

<400> SEQUENCE: 45
ccaaatccaa caatggagac c 21

<210> SEQ ID NO 46
<211> LENGTH: 23
<212> TYPE: DNA
<213> ORGANISM: Artificial Sequence
<220> FEATURE:
<223> OTHER INFORMATION: oligonucleotide primer AtM2 F2 R2 (reverse)

<400> SEQUENCE: 46
atgaatgaaa caagaagtac ttc 23

<210> SEQ ID NO 47
<211> LENGTH: 22
<212> TYPE: DNA
<213> ORGANISM: Artificial Sequence
<220> FEATURE:
<223> OTHER INFORMATION: oligonucleotide primer AtM2 F3 R3 (reverse)

<400> SEQUENCE: 47
caaaactcag agctatatga ac 22

<210> SEQ ID NO 48
<211> LENGTH: 22
<212> TYPE: DNA
<213> ORGANISM: Artificial Sequence
<220> FEATURE:
<223> OTHER INFORMATION: oligonucleotide primer AtM2 F4 R4 (reverse)

<400> SEQUENCE: 48
aagcatgtac ctggcctaga tc 22

<210> SEQ ID NO 49
<211> LENGTH: 20
<212> TYPE: DNA
<213> ORGANISM: Artificial Sequence
<220> FEATURE:
<223> OTHER INFORMATION: oligonucleotide primer AtM2 F5 R5 (reverse)

<400> SEQUENCE: 49
aggagttgga accaccttag 20

<210> SEQ ID NO 50
<211> LENGTH: 23
<212> TYPE: DNA
<213> ORGANISM: Artificial Sequence
<220> FEATURE:
<223> OTHER INFORMATION: oligonucleotide primer AtM2 F6 R6 (reverse)

<400> SEQUENCE: 50
caatacatat aaacgcagac atc 23

<210> SEQ ID NO 51

<211> LENGTH: 17
<212> TYPE: DNA
<213> ORGANISM: Artificial Sequence
<220> FEATURE:
<223> OTHER INFORMATION: oligonucleotide primer AtM2 F7 R7 (reverse)

<400> SEQUENCE: 51
gccagccggt tgtggcg 17

<210> SEQ ID NO 52
<211> LENGTH: 20
<212> TYPE: DNA
<213> ORGANISM: Artificial Sequence
<220> FEATURE:
<223> OTHER INFORMATION: oligonucleotide primer AtM3 F1 R1 (reverse)

<400> SEQUENCE: 52
tcttgttaga ggcatcgtcg 20

<210> SEQ ID NO 53
<211> LENGTH: 22
<212> TYPE: DNA
<213> ORGANISM: Artificial Sequence
<220> FEATURE:
<223> OTHER INFORMATION: oligonucleotide primer AtM3F2 R2 (reverse)

<400> SEQUENCE: 53
taaaactgtg tggatagaac ag 22

<210> SEQ ID NO 54
<211> LENGTH: 22
<212> TYPE: DNA
<213> ORGANISM: Artificial Sequence
<220> FEATURE:
<223> OTHER INFORMATION: oligonucleotide primer AtM3 F3 R3 (reverse)

<400> SEQUENCE: 54
aaggtctaca cacatcacat at 22

<210> SEQ ID NO 55
<211> LENGTH: 22
<212> TYPE: DNA
<213> ORGANISM: Artificial Sequence
<220> FEATURE:
<223> OTHER INFORMATION: oligonucleotide primer AtM3 F4 R4 (reverse)

<400> SEQUENCE: 55
aagcatatac ctggccttta ta 22

<210> SEQ ID NO 56
<211> LENGTH: 20
<212> TYPE: DNA
<213> ORGANISM: Artificial Sequence
<220> FEATURE:
<223> OTHER INFORMATION: oligonucleotide primer AtM3 F5 R5 (reverse)

<400> SEQUENCE: 56
agattctgca acacaccagc 20

<210> SEQ ID NO 57
<211> LENGTH: 23
<212> TYPE: DNA
<213> ORGANISM: Artificial Sequence
<220> FEATURE:
<223> OTHER INFORMATION: oligonucleotide primer AtM3 F6 R6 (reverse)

<400> SEQUENCE: 57
caatacaacc aaaccttgac ata 23

<210> SEQ ID NO 58
<211> LENGTH: 22
<212> TYPE: DNA
<213> ORGANISM: Artificial Sequence
<220> FEATURE:
<223> OTHER INFORMATION: oligonucleotide primer AtM3 F7 R7 (reverse)

<400> SEQUENCE: 58
ctaaaagcca ttcacattaa cc 22

<210> SEQ ID NO 59
<211> LENGTH: 19
<212> TYPE: DNA
<213> ORGANISM: Artificial Sequence
<220> FEATURE:
<223> OTHER INFORMATION: oligonucleotide primer AtM4F1R1 (reverse)

<400> SEQUENCE: 59
cacccgctgg ccactagtt 19

<210> SEQ ID NO 60
<211> LENGTH: 22
<212> TYPE: DNA
<213> ORGANISM: Artificial Sequence
<220> FEATURE:
<223> OTHER INFORMATION: oligonucleotide primer AtM4F2R2 (reverse)

<400> SEQUENCE: 60
gaaaacacca gcatgccatg gg 22

<210> SEQ ID NO 61
<211> LENGTH: 21
<212> TYPE: DNA
<213> ORGANISM: Artificial Sequence
<220> FEATURE:
<223> OTHER INFORMATION: oligonucleotide primer AtM5 F1 R1 (reverse)

<400> SEQUENCE: 61
ttgcattatc attccgtgca c 21

<210> SEQ ID NO 62
<211> LENGTH: 20
<212> TYPE: DNA
<213> ORGANISM: Artificial Sequence
<220> FEATURE:
<223> OTHER INFORMATION: oligonucleotide primer AtM5 F2 R2 (reverse)

<400> SEQUENCE: 62
tattctgaag ggacaagcgg 20

<210> SEQ ID NO 63
<211> LENGTH: 22
<212> TYPE: DNA
<213> ORGANISM: Artificial Sequence
<220> FEATURE:
<223> OTHER INFORMATION: oligonucleotide primer AtM5 F3 R3 (reverse)

<400> SEQUENCE: 63
agcacatcac acaacctctc gg 22

<210> SEQ ID NO 64
<211> LENGTH: 23
<212> TYPE: DNA

<213> ORGANISM: Artificial Sequence
<220> FEATURE:
<223> OTHER INFORMATION: oligonucleotide primer AtM6 F1 R1 (reverse)

<400> SEQUENCE: 64
acaagctgag ctctagaaga tgg 23

<210> SEQ ID NO 65
<211> LENGTH: 22
<212> TYPE: DNA
<213> ORGANISM: Artificial Sequence
<220> FEATURE:
<223> OTHER INFORMATION: oligonucleotide primer AtM7F1R1 (reverse)

<400> SEQUENCE: 65
taaacaaaca acctatctgc gc 22

<210> SEQ ID NO 66
<211> LENGTH: 23
<212> TYPE: DNA
<213> ORGANISM: Artificial Sequence
<220> FEATURE:
<223> OTHER INFORMATION: oligonucleotide primer AtM8F1R1 (reverse)

<400> SEQUENCE: 66
ctggtttatc catccgatcc acc 23

<210> SEQ ID NO 67
<211> LENGTH: 42
<212> TYPE: DNA
<213> ORGANISM: Artificial Sequence
<220> FEATURE:
<223> OTHER INFORMATION: oligonucleotide primer

<400> SEQUENCE: 67
ggccccactc atgacatggc gttagccatg ggaagcttgg at 42

<210> SEQ ID NO 68
<211> LENGTH: 19
<212> TYPE: DNA
<213> ORGANISM: Artificial Sequence
<220> FEATURE:
<223> OTHER INFORMATION: oligonucleotide primer to SR33-F

<400> SEQUENCE: 68
gcaggaggac gtggaaatc 19

<210> SEQ ID NO 69
<211> LENGTH: 22
<212> TYPE: DNA
<213> ORGANISM: Artificial Sequence
<220> FEATURE:
<223> OTHER INFORMATION: oligonucleotide primer to SR33-R

<400> SEQUENCE: 69
aaagtctacc atacagcgga ac 22

<210> SEQ ID NO 70
<211> LENGTH: 19
<212> TYPE: DNA
<213> ORGANISM: Artificial Sequence
<220> FEATURE:
<223> OTHER INFORMATION: oligonucleotide primer to Exo70-F

<400> SEQUENCE: 70
atggagcaat gcccaaagt 19

<210> SEQ ID NO 71
<211> LENGTH: 20
<212> TYPE: DNA
<213> ORGANISM: Artificial Sequence
<220> FEATURE:
<223> OTHER INFORMATION: oligonucleotide primer to Exo70-R

<400> SEQUENCE: 71
ggcatcagca aacaccaact 20

<210> SEQ ID NO 72
<211> LENGTH: 19
<212> TYPE: DNA
<213> ORGANISM: Artificial Sequence
<220> FEATURE:
<223> OTHER INFORMATION: oligonucleotide primer to HSP90-F

<400> SEQUENCE: 72
cgaccagcac gctcacgat 19

<210> SEQ ID NO 73
<211> LENGTH: 19
<212> TYPE: DNA
<213> ORGANISM: Artificial Sequence
<220> FEATURE:
<223> OTHER INFORMATION: oligonucleotide primer to HSP90-R

<400> SEQUENCE: 73
gcgatggtcc cgaggttgt 19

<210> SEQ ID NO 74
<211> LENGTH: 16
<212> TYPE: DNA
<213> ORGANISM: Artificial Sequence
<220> FEATURE:
<223> OTHER INFORMATION: oligonucleotide primer to SGT1-F

<400> SEQUENCE: 74
caagctgggc agttac 16

<210> SEQ ID NO 75
<211> LENGTH: 18
<212> TYPE: DNA
<213> ORGANISM: Artificial Sequence
<220> FEATURE:
<223> OTHER INFORMATION: oligonucleotide primer to SGT1-R

<400> SEQUENCE: 75
tccttcgatg cataaagc 18

<210> SEQ ID NO 76
<211> LENGTH: 18
<212> TYPE: DNA
<213> ORGANISM: Artificial Sequence
<220> FEATURE:
<223> OTHER INFORMATION: oligonucleotide primer to RAR1-F

<400> SEQUENCE: 76
atgcggtgcc agcgaata 18

<210> SEQ ID NO 77
<211> LENGTH: 18
<212> TYPE: DNA
<213> ORGANISM: Artificial Sequence
<220> FEATURE:

<223> OTHER INFORMATION: oligonucleotide primer to RAR1-R

<400> SEQUENCE: 77
gggttgtcgt cgtcggtg 18

<210> SEQ ID NO 78
<211> LENGTH: 23
<212> TYPE: DNA
<213> ORGANISM: Artificial Sequence
<220> FEATURE:
<223> OTHER INFORMATION: oligonucleotide primer to Actin-F

<400> SEQUENCE: 78
aaatctggca tcacactttc tac 23

<210> SEQ ID NO 79
<211> LENGTH: 24
<212> TYPE: DNA
<213> ORGANISM: Artificial Sequence
<220> FEATURE:
<223> OTHER INFORMATION: oligonucleotide primer to Actin-R

<400> SEQUENCE: 79
gtctcaaaca taatctgggt catc 24

<210> SEQ ID NO 80
<211> LENGTH: 20
<212> TYPE: DNA
<213> ORGANISM: Artificial Sequence
<220> FEATURE:
<223> OTHER INFORMATION: oligonucleotide primer 18SF

<400> SEQUENCE: 80
gtgacgggtg acggagaatt 20

<210> SEQ ID NO 81
<211> LENGTH: 20
<212> TYPE: DNA
<213> ORGANISM: Artificial Sequence
<220> FEATURE:
<223> OTHER INFORMATION: oligonucleotide primer to 18SR

<400> SEQUENCE: 81
gacactaatg cgcccggtat 20

<210> SEQ ID NO 82
<211> LENGTH: 17
<212> TYPE: DNA
<213> ORGANISM: Artificial Sequence
<220> FEATURE:
<223> OTHER INFORMATION: oligonucleotide primer to PDS-F

<400> SEQUENCE: 82
tgtctttagc gtgcaag 17

<210> SEQ ID NO 83
<211> LENGTH: 18
<212> TYPE: DNA
<213> ORGANISM: Artificial Sequence
<220> FEATURE:
<223> OTHER INFORMATION: oligonucleotide primer to PDS-R

<400> SEQUENCE: 83
gatgatttcg gtgtcact 18

<210> SEQ ID NO 84
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 84
atgaattcat ggatattgtc acgggtgcca ttg 33

<210> SEQ ID NO 85
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 85
atgtcgactc actctgcgtc agaaatcggt cctc 34

<210> SEQ ID NO 86
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 86
atgtcgactc acgcagcgtt catggtcttg ag 32

<210> SEQ ID NO 87
<211> LENGTH: 35
<212> TYPE: DNA
<213> ORGANISM: Artificial Sequence
<220> FEATURE:
<223> OTHER INFORMATION: oligonucleotide primer

<400> SEQUENCE: 87
atgtcgactc agtccttgat cgcgtgagct attcc 35

<210> SEQ ID NO 88
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 88
atgtcgactc atagagcacg gagacgagga tcaattgc 38

<210> SEQ ID NO 89
<211> LENGTH: 44
<212> TYPE: DNA
<213> ORGANISM: Artificial Sequence
<220> FEATURE:
<223> OTHER INFORMATION: oligonucleotide primer

<400> SEQUENCE: 89
atgtcgactc agtgacaatc aaaatcacct ttaatcttct cgta 44

<210> SEQ ID NO 90
<211> LENGTH: 45
<212> TYPE: DNA
<213> ORGANISM: Artificial Sequence
<220> FEATURE:
<223> OTHER INFORMATION: oligonucleotide primer

<400> SEQUENCE: 90
atgaattcat gctcacaaat atcatgagta tctcacaagt gaggt 45

<210> SEQ ID NO 91
<211> LENGTH: 26
<212> TYPE: DNA
<213> ORGANISM: Artificial Sequence
<220> FEATURE:
<223> OTHER INFORMATION: oligonucleotide primer

<400> SEQUENCE: 91
atcatatgtc ggcggagacg gagagg 26

<210> SEQ ID NO 92
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 92
gcatcgattc acacagcatc agcattgtgc ca 32

<210> SEQ ID NO 93
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 93
atgtcggcgg agacggagac g 21

<210> SEQ ID NO 94
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 94
taatcgattc atacggcatc agcattgtgc ca 32

<210> SEQ ID NO 95
<211> LENGTH: 23
<212> TYPE: DNA
<213> ORGANISM: Artificial Sequence
<220> FEATURE:
<223> OTHER INFORMATION: oligonucleotide primer

<400> SEQUENCE: 95
atgaattcat ggccgccgcc gcc 23

<210> SEQ ID NO 96
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 96
atatcgattt aatactccca cttcttgagc tccattcca 39

<210> SEQ ID NO 97
<211> LENGTH: 29

<212> TYPE: DNA
<213> ORGANISM: Artificial Sequence
<220> FEATURE:
<223> OTHER INFORMATION: oligonucleotide primer

<400> SEQUENCE: 97
gctatgaatt catggcgacg gagaccgag 29

<210> SEQ ID NO 98
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 98
gcataatcga tttagtcgac ctcctccatc ttgc 34

<210> SEQ ID NO 99
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 99
atgaattcat ggatccatgg atgggcagcc 30

<210> SEQ ID NO 100
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 100
atatcgattt aattgatgtc cctggtcggc ga 32

<210> SEQ ID NO 101
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 101
atgaattcat ggatccatgg gtcagcagcc a 31

<210> SEQ ID NO 102
<211> LENGTH: 34
<212> TYPE: DNA
<213> ORGANISM: Artificial Sequence
<220> FEATURE:
<223> OTHER INFORMATION: oligonucleotide primer

<400> SEQUENCE: 102
atatcgattt aattgatgtc cctggtcggc gata 34

<210> SEQ ID NO 103
<211> LENGTH: 31
<212> TYPE: DNA
<213> ORGANISM: Artificial Sequence
<220> FEATURE:
<223> OTHER INFORMATION: oligonucleotide primer

<400> SEQUENCE: 103
atgaattcat gccgcagcag cagaacgacg g 31

<210> SEQ ID NO 104
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 104
atgaattcat ggaggagcag tggatgatcg gg 32

<210> SEQ ID NO 105
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 105
atatcgattc aagcaacagg gatccgacca ga 32

<210> SEQ ID NO 106
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 106
atgaattcat gccgccgccc aagcatcaag 30

<210> SEQ ID NO 107
<211> LENGTH: 32
<212> TYPE: DNA
<213> ORGANISM: Artificial Sequence
<220> FEATURE:
<223> OTHER INFORMATION: oligonucleotide primer

<400> SEQUENCE: 107
atgaattcat ggacgagcag tggatgatcg gg 32

<210> SEQ ID NO 108
<211> LENGTH: 33
<212> TYPE: DNA
<213> ORGANISM: Artificial Sequence
<220> FEATURE:
<223> OTHER INFORMATION: oligonucleotide primer

<400> SEQUENCE: 108
atatcgattc aagcaacagg gatccgacca gag 33

<210> SEQ ID NO 109
<211> LENGTH: 30
<212> TYPE: DNA
<213> ORGANISM: Artificial Sequence
<220> FEATURE:
<223> OTHER INFORMATION: oligonucleotide primer

<400> SEQUENCE: 109
atgaattcat gccgccgccc aagcaacaag 30

<210> SEQ ID NO 110
<211> LENGTH: 9
<212> TYPE: PRT
<213> ORGANISM: Artificial Sequence
<220> FEATURE:
<223> OTHER INFORMATION: p-loop motif of NB domain
<220> FEATURE:
<221> NAME/KEY: X
<222> LOCATION: (2)..(3)
<223> OTHER INFORMATION: any amino acid
<220> FEATURE:
<221> NAME/KEY: X
<222> LOCATION: (5)..(5)
<223> OTHER INFORMATION: any amino acid
<220> FEATURE:
<221> NAME/KEY: X
<222> LOCATION: (8)..(8)
<223> OTHER INFORMATION: T or S

<400> SEQUENCE: 110

Gly Xaa Xaa Gly Xaa Gly Lys Xaa Thr
1               5

<210> SEQ ID NO 111
<211> LENGTH: 9
<212> TYPE: PRT
<213> ORGANISM: Artificial Sequence
<220> FEATURE:
<223> OTHER INFORMATION: p-loop motif of NB domain

<400> SEQUENCE: 111

Gly Phe Gly Gly Leu Gly Lys Thr Thr
1               5

<210> SEQ ID NO 112
<211> LENGTH: 8
<212> TYPE: PRT
<213> ORGANISM: Artificial Sequence
<220> FEATURE:
<223> OTHER INFORMATION: kinase 2 motif of NB domain
<220> FEATURE:
<221> NAME/KEY: X
<222> LOCATION: (2)..(4)
<223> OTHER INFORMATION: any amino acid

<400> SEQUENCE: 112

Leu Xaa Xaa Xaa Asp Asp Val Trp
1               5

<210> SEQ ID NO 113
<211> LENGTH: 8
<212> TYPE: PRT
<213> ORGANISM: Artificial Sequence
<220> FEATURE:
<223> OTHER INFORMATION: kinase 2 motif of NB domain

<400> SEQUENCE: 113

Leu Val Ile Ile Asp Asp Val Trp
1               5

<210> SEQ ID NO 114
<211> LENGTH: 9
<212> TYPE: PRT
<213> ORGANISM: Artificial Sequence
<220> FEATURE:
<223> OTHER INFORMATION: kinase 3a motif of NB domain
<220> FEATURE:
<221> NAME/KEY: X
<222> LOCATION: (2)..(5)
<223> OTHER INFORMATION: any amino acid
<220> FEATURE:
<221> NAME/KEY: X
<222> LOCATION: (6)..(6)
<223> OTHER INFORMATION: any amino acid or absent
<220> FEATURE:

```
<221> NAME/KEY: X
<222> LOCATION: (8)..(8)
<223> OTHER INFORMATION: any amino acid

<400> SEQUENCE: 114

Gly Xaa Xaa Xaa Xaa Xaa Thr Xaa Arg
1               5


<210> SEQ ID NO 115
<211> LENGTH: 9
<212> TYPE: PRT
<213> ORGANISM: Artificial Sequence
<220> FEATURE:
<223> OTHER INFORMATION: kinase 3a motif of NB domain

<400> SEQUENCE: 115

Gly Ser Arg Leu Ile Ile Thr Thr Arg
1               5


<210> SEQ ID NO 116
<211> LENGTH: 9
<212> TYPE: PRT
<213> ORGANISM: Artificial Sequence
<220> FEATURE:
<223> OTHER INFORMATION: LRR repeat motif
<220> FEATURE:
<221> NAME/KEY: X
<222> LOCATION: (1)..(2)
<223> OTHER INFORMATION: any amino acid
<220> FEATURE:
<221> NAME/KEY: X
<222> LOCATION: (4)..(4)
<223> OTHER INFORMATION: any amino acid
<220> FEATURE:
<221> NAME/KEY: X
<222> LOCATION: (6)..(9)
<223> OTHER INFORMATION: any amino acid

<400> SEQUENCE: 116

Xaa Xaa Leu Xaa Leu Xaa Xaa Xaa Xaa
1               5
```

WHEAT STEM RUST RESISTANCE GENE

FIELD OF THE INVENTION

The present invention relates to a transgenic plant which has integrated into its genome an exogenous polynucleotide encoding a polypeptide which confers resistance to *Puccinia graminis*, such as the Ug99 group of races of *Puccinia graminis* f. sp. *tritici*.

BACKGROUND OF THE INVENTION

Stem rust (*Puccinia graminis* f. sp. *tritici*) of wheat is a major threat to global food security and necessitates the continued development of new stem rust resistant varieties. A stem rust race, Ug99 or TTKSK, first confirmed in Uganda in 1999 is virulent on many commercial varieties including those carrying the Sr31 resistance gene which hitherto had proven to be durable and widely cultivated (Jones et al., 1991; Bariana and McIntosh, 1993). Ug99 and its mutant derived races have spread to other African regions and the Middle East. Concerns over a potential epidemic should it reach the bread baskets of Asia has been a key driver of a global initiative to combat the food security threat posed by Ug99 and its lineage. Over 90% of wheat varieties in the proposed migration route of the pathogen are susceptible (Bariana and McIntosh, 1993). Global wheat breeding efforts to improve rust resistance are largely founded upon the repertoire of immune recognition specificities against the arsenal of wheat rust pathogen effectors that are embodied in the major resistance (R) genes found in the gene pool of wheat and its relatives. Combining different specific R genes capable of detecting a wide range of effectors is regarded as an effective strategy to contain rust epidemics in commercial agriculture.

Over 50 stem rust R genes that confer resistance at all growth stages have been catalogued in wheat inclusive of those introgressed from wild relatives. To date, none of these wheat stem rust R genes have been cloned. By contrast three wheat R genes (Lr1, Lr10 and Lr21) that provide protection against the wheat leaf rust fungus, *Puccinia triticina*, have been cloned (Somers et al., 2004; Hayden et al., 2008; Manly et al., 2001). The wheat stem rust R gene, Sr33, derived from the diploid D genome progenitor, *Aegilops tauschii*, (Kosambi, 1944) of common wheat (*Triticum aestivum*) exhibits a number of interesting features; it provides an intermediate resistance infection response against the Ug99 race and its lineage as well as all the commonly available rust isolates from diverse geographical regions (Kota et al., 2006). Efforts are underway to fully sequence the genomes and characterise effectors from wheat stem rust pathogens including Ug99 (Akhunov et al., 2010).

There is an urgent need for the identification of genes which confer at least some level of resistance to plants, especially wheat, against *Puccinia graminis*, such as the Ug99 group of races of *Puccinia graminis* f. sp. *tritici*.

SUMMARY OF THE INVENTION

The present inventors have identified polypeptides which confer at least some level of resistance to plants, especially wheat, against *Puccinia graminis*, such as the Ug99 group of races of *Puccinia graminis* f. sp. *tritici*.

Thus, in a first aspect the present invention provides a transgenic plant which has integrated into its genome an exogenous polynucleotide encoding a polypeptide which confers resistance to *Puccinia graminis*, wherein the polynucleotide is operably linked to a promoter capable of directing expression of the polynucleotide in a cell of the plant.

In an embodiment, the *Puccinia graminis* is *Puccinia graminis* f. sp. *tritici*. In a further embodiment, the *Puccinia graminis* f. sp. *tritici* is a race of the Ug99 group.

In another embodiment, the transgenic plant has enhanced resistance to *Puccinia graminis* when compared to an isogenic plant lacking the exogenous polynucleotide.

In an embodiment, the polypeptide is an Sr33 polypeptide.

In a further embodiment, i) the polypeptide comprises amino acids having a sequence as provided in SEQ ID NO:1 or SEQ ID NO:2, a biologically active fragment thereof, or an amino acid sequence which is at least 87% identical to one or both of SEQ ID NO:1 and SEQ ID NO:2, and/or ii) the polynucleotide comprises nucleotides having a sequence as provided in SEQ ID NO:3 or SEQ ID NO:4, a sequence which is at least 87% identical to one or both of SEQ ID NO:3 and SEQ ID NO:4, or a sequence which hybridizes to one or both of SEQ ID NO:3 and SEQ ID NO:4.

In an embodiment, the polypeptide comprises one or more, preferably all, of a coiled coil (CC) domain, an nucleotide binding (NB) domain and a leucine rich repeat (LRR) domain.

In a further embodiment, the polypeptide comprises one or more, preferably all, of a p-loop motif, a kinase 2 motif and a kinase3a motif in the NB domain.

In an embodiment, the p-loop motif comprises the sequence GxxGxGK(T/S)T (SEQ ID NO:110), more preferably the sequence GFGGLGKTT (SEQ ID NO: 111).

In an embodiment, the kinase 2 motif comprises the sequence LxxxDDVW (SEQ ID NO: 112), more preferably the sequence LVIIDDVW (SEQ ID NO: 113).

In an embodiment, the kinase 3a motif comprises the sequence GxxxxxTxR (SEQ ID NO:114), more preferably the sequence GSRLIITTR (SEQ ID NO: 115).

In a further embodiment, the LRR domain comprises about 10 to about 20 imperfect repeats of the sequence xxLxLxxxx (SEQ ID NO: 116).

Preferably, the plant is a cereal plant. Examples of transgenic cereal plants of the invention include, but are not limited to wheat, barley, maize, rice, oats and triticale. In a particularly preferred embodiment, the plant is wheat.

In a further embodiment, the plant comprises one or more further exogenous polynucleotides encoding another plant pathogen resistance polypeptide. Examples of such other plant pathogen resistance polypeptides include, but are not limited to, Lr34, Lr1, Lr3, Lr2a, Lr3ka, Lr11, Lr13, Lr16, Lr17, Lr18, Lr21, LrB and Sr35.

Preferably, the plant is homozygous for the exogenous polynucleotide.

In an embodiment, the plant is growing in a field.

Also provided is a population of at least 100 transgenic plants of the invention growing in a field.

In a further aspect, the present invention provides a process for identifying a polynucleotide encoding a polypeptide which confers resistance to *Puccinia graminis* comprising:

i) obtaining a polynucleotide operably linked to a promoter, the polynucleotide encoding a polypeptide comprising amino acids having a sequence as provided in SEQ ID NO:1 or SEQ ID NO:2, a biologically active fragment thereof, or an amino acid sequence which is at least 40% identical to one or both of SEQ ID NO:1 and SEQ ID NO:2, ii) introducing the polynucleotide into a plant, iii) determining whether the level of resistance to *Puccinia graminis* is modified relative to an isogenic plant lacking the polynucleotide, and iv) optionally, selecting a polynucleotide which when expressed confers resistance to *Puccinia graminis.*

In an embodiment the process has one or more of the following, a) the polynucleotide comprises nucleotides having a sequence as provided in SEQ ID NO:3 or SEQ ID NO:4, a sequence which is at least 40% identical to one or both of SEQ ID NO:3 and SEQ ID NO:4, or a sequence which hybridizes to one or both of SEQ ID NO:3 and SEQ ID NO:4, b) the plant is a cereal plant such as a wheat plant, c) the polypeptide is a plant polypeptide or mutant thereof, and d) step ii) further comprises stably integrating the polynucleotide operably linked to a promoter into the genome of the plant.

Also provided is a substantially purified and/or recombinant *Puccinia graminis* plant resistance polypeptide.

In an embodiment, the polypeptide is an Sr33 polypeptide.

In another embodiment, the polypeptide comprises amino acids having a sequence as provided in SEQ ID NO:1 or SEQ ID NO:2, a biologically active fragment thereof, or an amino acid sequence which is at least 87% identical, at least 90% identical, or at least 95% identical, to one or both of SEQ ID NO:1 and SEQ ID NO:2.

In a further aspect, the present invention provides a substantially purified and/or recombinant polypeptide comprising amino acids having a sequence as provided in SEQ ID NO:1 or SEQ ID NO:2, or an amino acid sequence which is at least 87% identical, at least 90% identical, or at least 95% identical, to one or both of SEQ ID NO:1 and SEQ ID NO:2.

In an embodiment, a polypeptide of the invention is a fusion protein further comprising at least one other polypeptide sequence. The at least one other polypeptide may be, for example, a polypeptide that enhances the stability of a polypeptide of the present invention, or a polypeptide that assists in the purification or detection of the fusion protein.

In yet a further aspect, the present invention provides an isolated and/or exogenous polynucleotide comprising nucleotides having a sequence as provided in SEQ ID NO:3 or SEQ ID NO:4, a sequence which is at least 87% identical to one or both of SEQ ID NO:3 and SEQ ID NO:4, a sequence encoding a polypeptide of the invention, or a sequence which hybridizes to one or both of SEQ ID NO:3 and SEQ ID NO:4.

In another aspect, the present invention provides a chimeric vector comprising the polynucleotide of the invention.

Preferably, the polynucleotide is operably linked to a promoter.

In a further aspect, the present invention provides a recombinant cell comprising an exogenous polynucleotide of the invention and/or a vector of the invention.

The cell can be any cell type such as, but not limited to, a plant cell, a bacterial cell, an animal cell or a yeast cell.

Preferably, the cell is a plant cell. More preferably, the plant cell is a cereal plant cell. Even more preferably, the cereal plant cell is a wheat cell.

In a further aspect, the present invention provides a method of producing the polypeptide of the invention, the method comprising expressing in a cell or cell free expression system the polynucleotide of the invention.

Preferably, the method further comprises isolating the polypeptide.

In yet another aspect, the present invention provides a transgenic non-human organism comprising an exogenous polynucleotide of the invention, a vector of the invention and/or a recombinant cell of the invention.

Preferably, the transgenic non-human organism is a plant. Preferably, the plant is a cereal plant. More preferably, the cereal plant is a wheat plant.

In another aspect, the present invention provides a method of producing the cell of the invention, the method comprising the step of introducing the polynucleotide of the invention, or a vector of the invention, into a cell.

Preferably, the cell is a plant cell.

In a further aspect, the present invention provides a method of producing a transgenic plant of the invention, the method comprising the steps of i) introducing a polynucleotide of the invention and/or a vector of the invention into a cell of a plant, ii) regenerating a transgenic plant from the cell, and iii) optionally harvesting seed from the plant, and/or iv) optionally producing one or more progeny plants from the transgenic plant, thereby producing the transgenic plant.

In a further aspect, the present invention provides a method of producing a plant which has integrated into its genome a polynucleotide encoding a polypeptide which confers resistance to *Puccinia graminis*, the method comprising the steps of i) crossing two parental plants, wherein at least one plant comprises a polynucleotide encoding a polypeptide which confers resistance to *Puccinia graminis,* ii) screening one or more progeny plants from the cross for the presence or absence of the polynucleotide, and iii) selecting a progeny plant which comprise the polynucleotide, thereby producing the plant.

In an embodiment, at least one of the parental plants is a transgenic plant of the invention, and the selected progeny plant comprises an exogenous polynucleotide encoding a polypeptide which confers resistance to *Puccinia graminis.*

In a further embodiment, at least one of the parental plants is a tetraploid or hexaploid wheat plant.

In yet another embodiment, step ii) comprises analysing a sample comprising DNA from the plant for the polynucleotide.

In another embodiment, step iii) comprises i) selecting progeny plants which are homozygous for the polynucleotide, and/or ii) analysing the plant or one or more progeny plants thereof for resistance to *Puccinia graminis.*

In an embodiment, the method further comprises iv) backcrossing the progeny of the cross of step i) with plants of the same genotype as a first parent plant which lacked a polynucleotide encoding a polypeptide which confers resistance to *Puccinia graminis* for a sufficient number of times to produce a plant with a majority of the genotype of the first parent but comprising the polynucleotide, and iv) selecting a progeny plant which has resistance to *Puccinia graminis.*

In yet another aspect, a method of the invention further comprises the step of analysing the plant for at least one other genetic marker.

Also provide is a plant produced using a method of the invention.

In another aspect, the present invention provides for the use of the polynucleotide of the invention, or a vector of the invention, to produce a recombinant cell and/or a transgenic plant.

In an embodiment, the transgenic plant has enhanced resistance to *Puccinia graminis* when compared to an isogenic plant lacking the exogenous polynucleotide and/or vector.

In a further aspect, the present invention provides a method for identifying a plant comprising a polynucleotide encoding a polypeptide which confers resistance to *Puccinia graminis*, the method comprising the steps of i) obtaining a nucleic acid sample from a plant, and ii) screening the sample for the presence or absence of the polynucleotide, wherein presence of the polynucleotide indicates that the plant is resistant to *Puccinia graminis*.

In an embodiment, the polynucleotide encodes a polypeptide of the invention.

In a further embodiment, the method identifies a transgenic plant of the invention.

In another embodiment, the method further comprises producing a plant from a seed before step i).

Also provided is a plant part of the plant of the invention.

In an embodiment, the plant part is a seed that comprises an exogenous polynucleotide which encodes a polypeptide which confers resistance to *Puccinia graminis*.

In a further aspect, the present invention provides a method of producing a plant part, the method comprising, a) growing a plant of the invention, and b) harvesting the plant part.

In another aspect, the present invention provides a method of producing flour, wholemeal, starch or other product obtained from seed, the method comprising;

a) obtaining seed of the invention, and b) extracting the flour, wholemeal, starch or other product.

In a further aspect, the present invention provides a product produced from a plant of the invention and/or a plant part of the invention.

In an embodiment, the part is a seed.

In an embodiment, the product is a food product or beverage product. Examples include, but are not limited to;

i) the food product being selected from the group consisting of: flour, starch, leavened or unleavened breads, pasta, noodles, animal fodder, breakfast cereals, snack foods, cakes, malt, beer, pastries and foods containing flour-based sauces, or ii) the beverage product being beer or malt.

In an alternative embodiment, the product is a non-food product. Examples include, but are not limited to, films, coatings, adhesives, building materials and packaging materials.

In a further aspect, the present invention provides a method of preparing a food product of the invention, the method comprising mixing seed, or flour, wholemeal or starch from the seed, with another food ingredient.

In another aspect, the present invention provides a method of preparing malt, comprising the step of germinating seed of the invention.

Also provided is the use of a plant of the invention, or part thereof, as animal feed, or to produce feed for animal consumption or food for human consumption.

In a further aspect, the present invention provides a composition comprising one or more of a polypeptide of the invention, a polynucleotide of the invention, a vector of the invention, or a recombinant cell of the invention, and one or more acceptable carriers.

In another aspect, the present invention provides a method of identifying a compound that binds to a polypeptide comprising amino acids having a sequence as provided in SEQ ID NO:1 or SEQ ID NO:2, a biologically active fragment thereof, or an amino acid sequence which is at least 40% identical to one or both of SEQ ID NO: 1 and SEQ ID NO:2, the method comprising:

i) contacting the polypeptide with a candidate compound, and ii) determining whether the compound binds the polypeptide.

Any embodiment herein shall be taken to apply mutatis mutandis to any other embodiment unless specifically stated otherwise.

The present invention is not to be limited in scope by the specific embodiments described herein, which are intended for the purpose of exemplification only. Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

The invention is hereinafter described by way of the following non-limiting Examples and with reference to the accompanying figures.

BRIEF DESCRIPTION OF THE ACCOMPANYING DRAWINGS

FIG. 1. Schematic diagram of the synteny between (c) wheat 1DS region carrying Sr33 with (a) *Ae. tauschii* (AL8/78) BAC contigs (b) *Ae. tauschii* (AUS18913) BACs, (d) barley, (e) *Brachypodium* and (f) rice. The ovals represent the genes used for the study. The numbers in (c) indicate the number of recombinants per 2850 gametes. The numbers in (d) to (f) show the physical distance in kilobases between the markers. Numbers in (a) and (b) indicate the designated *Ae. tauschii* BACs as follows: 1. HI134N19, 2. HD512N18, 3. RI353E24, 4. HI328O18, 5. HD071G23, 6. HD147M18, 7. HD036N08, 8. RI074M08, 9. HI085F18, 10. 69I06, 11. 172J10 and 12. 86D17.

Figure 2:
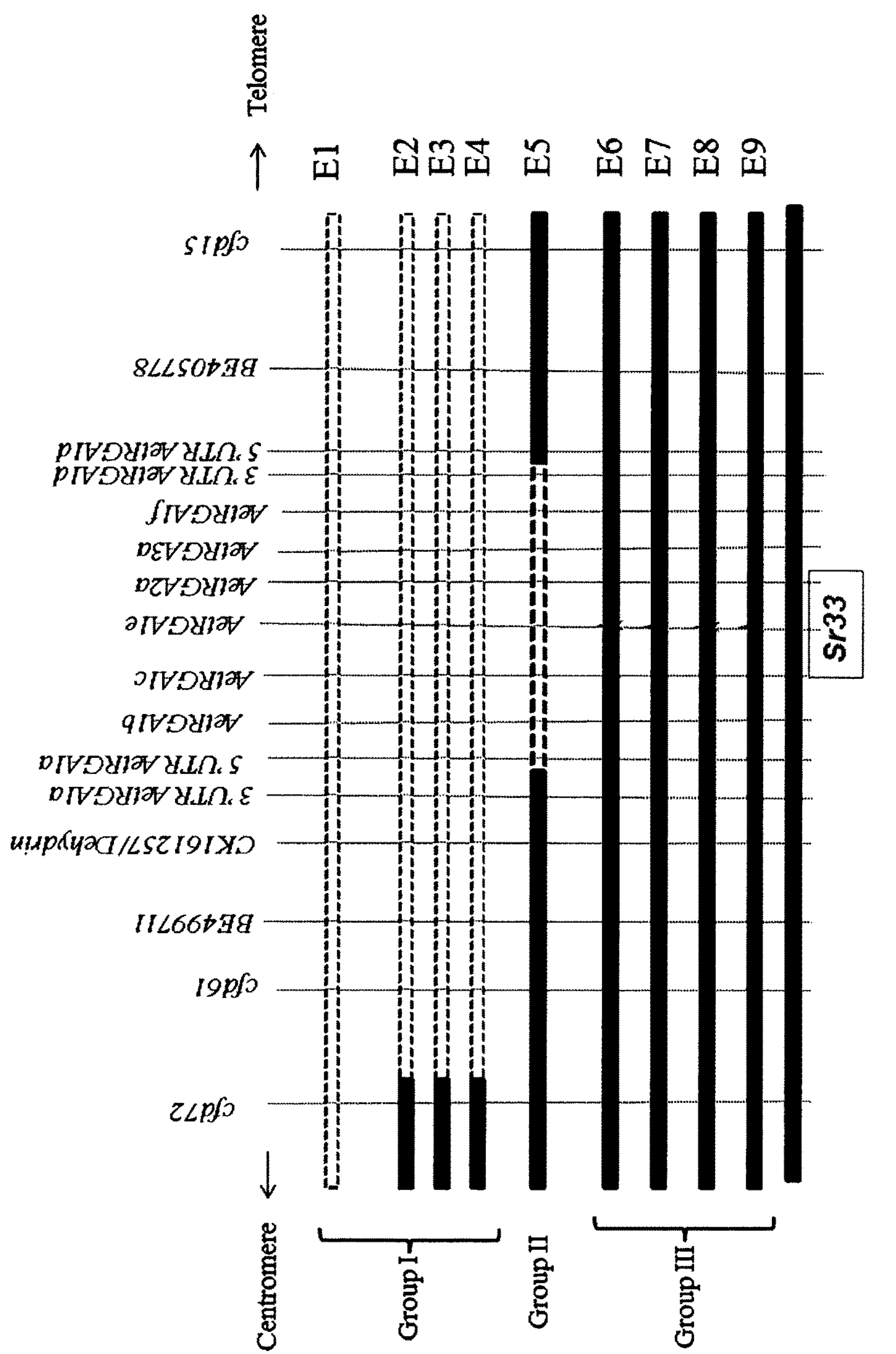

FIG. 2. Schematic diagram of the types of susceptible mutants generated through EMS treatment. Dotted bars indicate the length of chromosome segment lost due to mutation while the "Sr33" represent the SNP change in the AeRGA1e gene.

Figure 3:
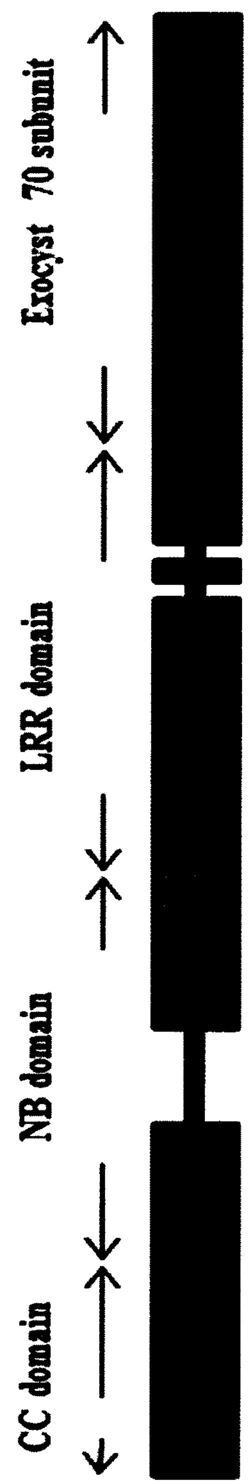

FIG. 3. Schematic diagram of the structure of the AetRGA2b polypeptide. The amino acid sequence predicted through RT-PCR analysis comprised of CC, NB and LRR domains related to RGA2 class of barley Mla locus and an unusual domain related to an Exocyst 70 subunit.

Figure 4:
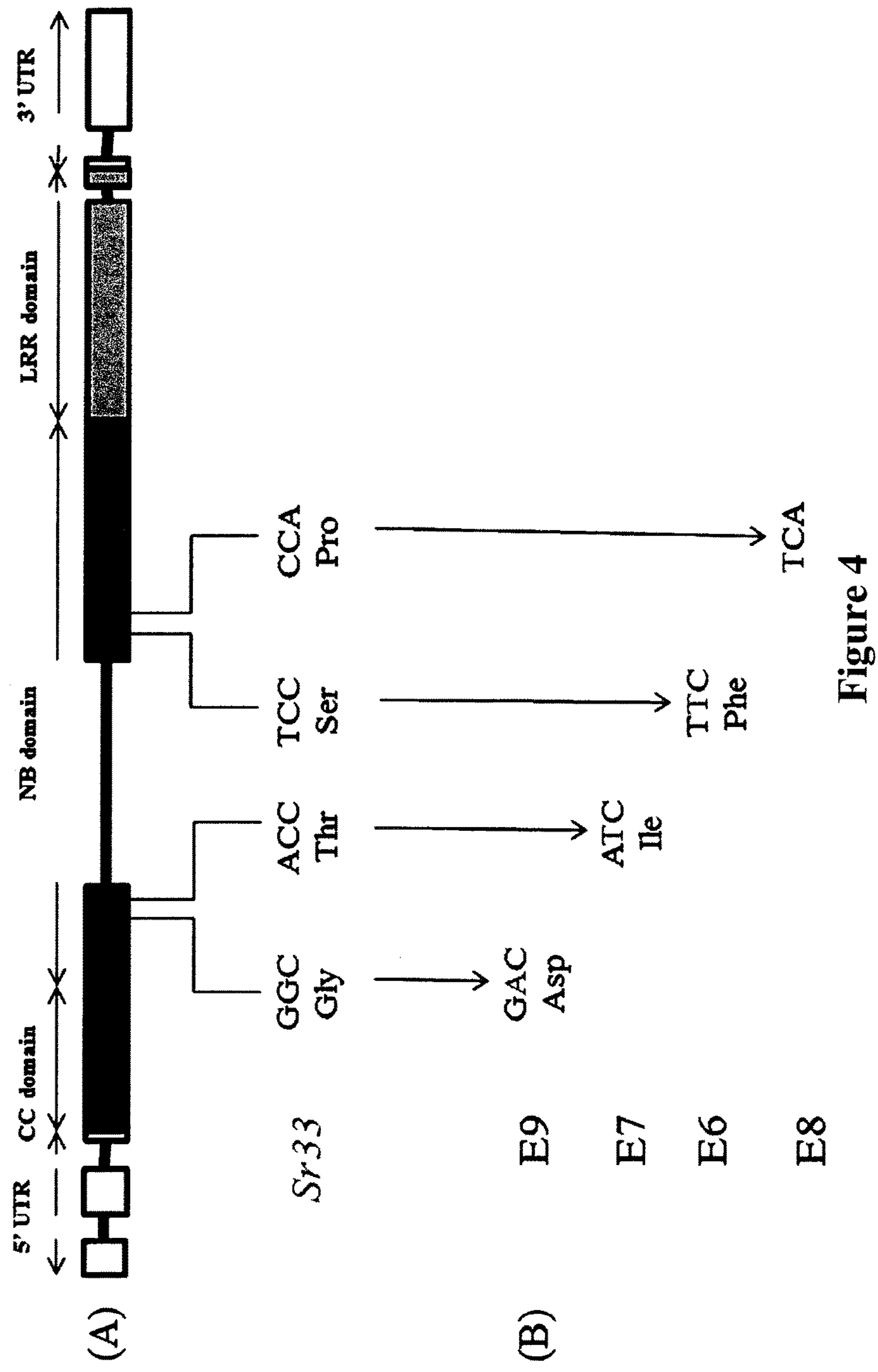

FIG. 4. (A) Schematic diagram of the structure of Sr33 (AetRGA1e). Rectangle bars represent exons and UTRs, while the black lines in-between indicate the introns. (B) Details of the nucleotide and the corresponding amino acid changes in the four point mutants. E9 and E7 have the substitutions in P-loop (Walker A) while E6 and E8 have substitutions in the RNBS-B and GLPL motifs of NB domain, respectively.

Figure 5:
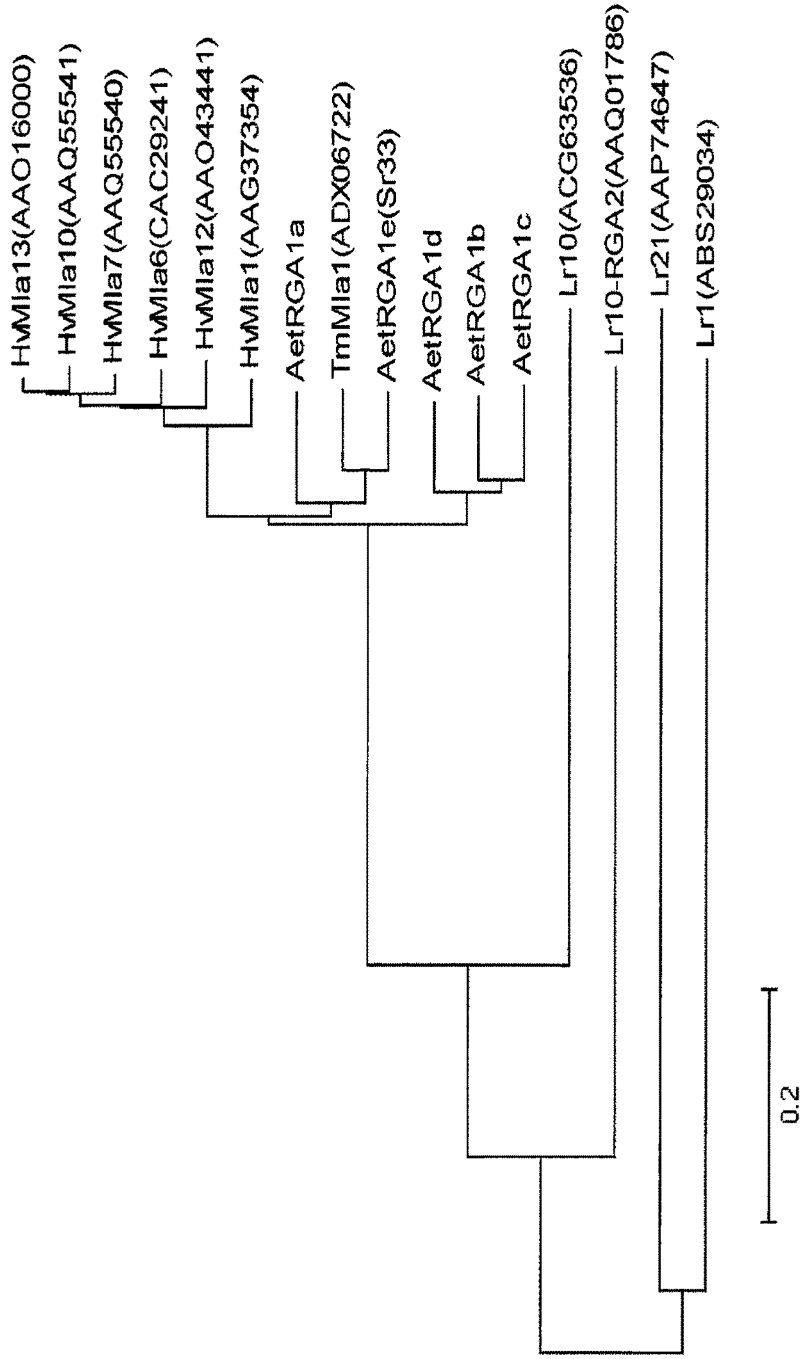

FIG. 5. Neighbor-joining tree analysis of RGA polypeptides from *Ae. tauschii* (AetRGA), functional Mla of barley (HvMla) and *T. monococcum* (TmMla) and leaf rust resistance of CC-NB-LRR type (Lr1, Lr10 and Lr21) from wheat.

FIG. 6. Alignment of the polypeptide amino acid sequences for the haplotypes identified for the alleles of the Sr33 gene in *Ae. tauschii*. Polymorphic changes are indicated by shading and the dotted lines represent deletion variations. Sequences for the haplotypes are as follows: HaplotypeI, SEQ ID NO:1, HaplotypeII, SEQ ID NO:2, HaplotypeIII, SEQ ID NO:6, HaplotypeIV, SEQ ID NO:7, and HaplotypeV, SEQ ID NO:8.

Figure 7:
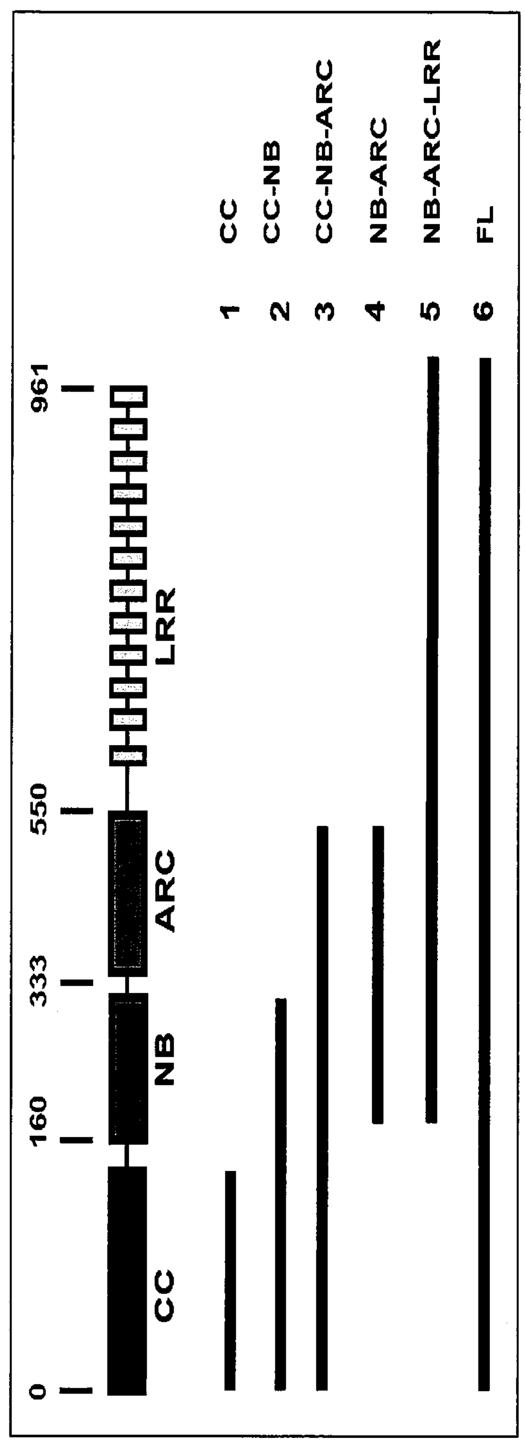

FIG. 7. Graphical schematic and numerical denomination of truncated Sr33 constructs described in Example 7.

KEY TO THE SEQUENCE LISTING

SEQ ID NO:1—Amino acid sequence of stem rust resistance polypeptide (from haplotype I).
SEQ ID NO:2—Amino acid sequence of allelic variant of the stem rust resistance polypeptide provided as SEQ ID NO: 1 (from haplotype II).
SEQ ID NO:3—Nucleotide sequence encoding the stem rust resistance polypeptide (from haplotype I) of SEQ ID NO:1.
SEQ ID NO:4—Nucleotide sequence encoding the stem rust resistance polypeptide (from haplotype II) of SEQ ID NO:2.
SEQ ID NO:5—Nucleotide sequence of the gene encoding the stem rust resistance polypeptide (from haplotype I) of SEQ ID NO: 1.
SEQ ID NO:6—Amino acid sequence of Sr33 polypeptide variant haplotype III.
SEQ ID NO:7—Amino acid sequence of Sr33 polypeptide variant haplotype IV.
SEQ ID NO:8—Amino acid sequence of Sr33 polypeptide variant haplotype V.
SEQ ID NO:9—Nucleotide sequence encoding Sr33 polypeptide variant haplotype III.
SEQ ID NO:10—Nucleotide sequence encoding Sr33 polypeptide variant haplotype IV.
SEQ ID NO: 11—Nucleotide sequence encoding Sr33 polypeptide variant haplotype V.
SEQ ID NO:12—Nucleotide sequence of the gene encoding the stem rust resistance polypeptide (from haplotype II) of SEQ ID NO:2.
SEQ ID NOs 13 to 109—Oligonucleotide primers.
SEQ ID NO: 110—Consenus p-loop motif.
SEQ ID NO: 111—P-loop motif of polypeptide provided as SEQ ID NO: 1.
SEQ ID NO: 112—Consenus kinase 2 motif.
SEQ ID NO: 113—Kinase 2 motif of polypeptide provided as SEQ ID NO:1.
SEQ ID NO: 114—Consenus kinase 3a motif.
SEQ ID NO: 115—Kinase 3a motif of polypeptide provided as SEQ ID NO:1.
SEQ ID NO:116—Consensus repeat of the LRR domain.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, molecular genetics, plant molecular biology, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The term "and/or", e.g., "X and/or Y" shall be understood to mean either "X and Y" or "X or Y" and shall be taken to provide explicit support for both meanings or for either meaning.

As used herein, the term about, unless stated to the contrary, refers to +/−10%, more preferably +/−5%, more preferably +/−1%, more preferably +/−0.5%, of the designated value.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Stem Rust

As used herein, "stem rust" refers to the disease of plants caused by *Puccinia graminis* or to the causative fungal pathogen, *Puccinia graminis*, as the context determines. As used herein, "wheat stem rust" refers to the disease of plants caused by *Puccinia graminis* f. sp. *tritici* or to the causative fungal pathogen, *Puccinia graminis* f. sp. *tritici*, as the context determines.

The Ug99 group of races of wheat stem rust (*Puccinia graminis* f. sp. *tritici*) (also known as 'TTKSK' under the North American nomenclature system) is a well known fungal pathogen of wheat and is commonly present in wheat fields in countries such as in Africa and the Middle East (Singh et al., 2011; Hodson et al., 2012). Ug99 can cause major crop losses and is virulent against resistance genes that have previously protected wheat against stem rust. There are currently eight known variants of group Ug99 which are closely related based on DNA marker analysis. Each variant of the pathogen which differs in its virulence/avirulence profile on a panel of wheat plants each comprising a different resistance R gene is known as a "race" of the pathogen. The Ug99 group of isolates are all closely related and are believed to have evolved from a common ancestor, but may differ in their virulence/avirulence profiles in which case they are considered different races. Seven of these eight variants are summarized in Table 2 of Singh et al. (2011). In an embodiment, the Ug99 group of stem rust races exhibit virulence on wheat plants comprising one or more of the resistance genes Sr31, Sr21, Sr24 and Sr36 (Singh et al., 2011). In one embodiment, the Ug99 group of stem rust races of *Puccinia graminis* f. sp. *tritici* has virulence at least to wheat plants comprising the resistance gene Sr31 (Pretorius et al., 2000).

Polypeptides/Peptides

The present invention relates to polypeptides which confer resistance to a plant, for example a wheat plant, to stem rust, preferably to wheat stem rust such as the Ug99 group of races. In a preferred embodiment, the polypeptide is encoded by an allele or variant of an Sr33 gene which confers resistance to wheat stem rust. Examples of such polypeptides include, but are not limited to, those comprising an amino acid sequence as provided in SEQ ID NO:1 and SEQ ID NO:2. The polypeptide of the invention confers enhanced resistance to stem rust, preferably wheat stem rust such as the Ug99 group of races of *Puccinia graminis* f. sp. *tritici* when compared to an isogenic plant lacking a gene encoding the polypeptide. This term also refers to the naturally produced protein (or wild-type protein from which a mutant protein is derived) encoded by a gene conferring upon a plant (for example, wheat), when grown in normal field conditions, enhanced resistance to stem rust such as the Ug99 group of races of *Puccinia graminis* f. sp. *tritici*. In a preferred embodiment, the polypeptide of the invention confers resistance specifically to stem rust, preferably specifically to wheat stem rust, more preferably it does not confer resistance to wheat leaf rust caused by the fungal pathogen *Puccinia triticina* and/or to powdery mildew. In this context, "specifically to stem rust" and "specifically to wheat stem rust" means that the conferred resistance is preferentially to stem rust or wheat stem rust in comparison to another fungal pathogen of the same plant species, preferably to many or most other fungal pathogens of the same species. In a more preferred embodiment, the polypeptide of the invention confers resistance to stem rust and at least two, or all three, of leaf rust, stripe rust and powdery mildew, preferably in wheat. In an embodiment, polypeptides of the invention are not encoded by the Sr35 gene of a wheat plant. In an embodiment, polypeptides of the invention are not encoded by the Sr35 gene of a wheat plant or its homologs, such as those that are at least 50% identical in amino acid sequence to the Sr35 polypeptide.

In an embodiment, a polypeptide of the invention does not bind one or more or all of RAR1, SGT1 or HSP90. In a further embodiment, a polypeptide of the invention does not bind WRKY1/2 such as a WRKY protein from barley or *Ae. tauchii*. In another embodiment, a polypeptide of the invention does form homodimers.

In a further embodiment, when expressed in a transgenic plant infected with stem rust, such as with a Ug99 race of *Puccinia graminis* f. sp. *tritici*, the cells of the plant display little, if any, signs of cell death (autofluorescence), for instance when compared to an isogenic plant expressing Sr45.

Polypeptides of the invention typically comprise a coiled coil (CC) domain towards the N-terminus, followed by an nucleotide binding (NB) domain and a leucine rich repeat (LRR) domain towards the C-terminus (see FIG. 4). Each of these three types of domains are common in polypeptides that confer resistance to plant pathogens. In addition, CC-NB-LRR containing polypeptides are a known large class of polypeptides which, as a class, confer resistance across a wide variety of different plant pathogens (see, for example, Bulgarelli et al., 2010; McHale et al., 2006; Takken et al., 2006; Wang et al., 2011; Gennaro et al., 2009; and Dilbirligi et al., 2003), although each CC-NB-LRR polypeptides is specific to a particular species or sub-species of pathogen. Accordingly, by aligning the polypeptides of the invention with other CC-NB-LRR polypeptides, combined with the large number of studies on these types of proteins as well as CC domains, NB domains and LRR domains, the skilled person has a considerable amount of guidance for designing functional variants of the specific polypeptides provided herein.

A coiled-coil domain or motif is a structural motif which is one of the most common tertiary structures of proteins where α-helices are coiled together like the strands of a rope. Computer programs have been devised to detect heptads and resulting in coiled-coil structures (see, for example Delorenzi and Speed, 2002). Coiled coils typically comprise a repeated pattern, hxxhcxc, of hydrophobic (h) and charged (c) amino-acid residues, referred to as a heptad repeats. The positions in the heptad repeat are usually labeled abcdefg, where a and d are the hydrophobic positions, often being occupied by isoleucine, alanine, leucine or valine. Folding a protein with these hepatds into an α-helical secondary structure causes the hydrophobic residues to be presented as a 'stripe' that coils gently around the helix in left-handed fashion, forming an amphipathic structure.

The NB domain is present in resistance genes as well as several kinases such as ATP/GTP-binding proteins. This domain typically contains three motifs: kinase-1a (p-loop), a kinase-2, and a putative kinase-3a (Traut 1994; Tameling et al., 2002). The consensus sequence of GxxGxGK(T/S)T (SEQ ID NO:110) (GFGGLGKTT (SEQ ID NO: 111) in the polypeptide which confers resistance to *Puccinia graminis* provided as SEQ ID NO:1), LxxxDDVW (SEQ ID NO:112) (LVIIDDVW (SEQ ID NO:113) in the polypeptide which confers resistance to *Puccinia graminis* provided as SEQ ID NO:1) and GxxxxxTxR (SEQ ID NO:114) (GSRLIITTR (SEQ ID NO:115) in the polypeptide which confers resistance to *Puccinia graminis* provided as SEQ ID NO:1) for the resistance gene motifs p-loop, kinase-2, and the putative kinase-3a, respectively, are different from those present in other NB-encoding proteins. Other motifs present in the NB domain of NB/LRR-type resistance genes are GLPL, RNBS-D and MHD (Meyers et al., 1999). The sequences interspersing these motifs and domains can be very different even among homologues of a resistance gene (Michelmore and Meyers, 1998; Pan et al., 2000).

A leucine-rich domain is a protein structural motif that forms an α/β horseshoe fold (Enkhbayar et al., 2004). The LRR domain contains 9-41 imperfect repeats, each about 25 amino acids long with a consensus amino acid sequence of xxLxLxxxx (SEQ ID NO:16) (Cooley et al., 2000). In an embodiment, a polypeptide of the invention comprises about 10 to about 20, more preferably about 12 to about 18, more preferably about 15 leucine rich repeats. These repeats commonly fold together to form a solenoid protein domain. Typically, each repeat unit has beta strand-turn-alpha helix structure, and the assembled domain, composed of many such repeats, has a horseshoe shape with an interior parallel beta sheet and an exterior array of helices.

In a further embodiment, the polypeptide which confers resistance to *Puccinia graminis* has a phenylalanine at a position corresponding to amino acid number 99 of SEQ ID NO:1 and/or an aspartic acid at a position corresponding to amino acid number 501 of SEQ ID NO:1.

As used herein, "resistance" is a relative term in that the presence of a polypeptide of the invention (i) reduces the disease symptoms of a plant comprising the gene (R gene) that confers resistance, relative to a plant lacking the R gene, and/or (ii) reduces pathogen reproduction or spread on a plant comprising the R gene. Resistance as used herein is relative to the "susceptible" response of a plant to the same pathogen. Typically, the presence of the R gene improves at least one production trait of a plant comprising the R gene when infected with the pathogen, such as grain yield, when compared to an isogenic plant infected with the pathogen but lacking the R gene. The isogenic plant may have some level of resistance to the pathogen, or may be classified as susceptible. Thus, the terms "resistance" and "enhanced resistance" are generally used herein interchangeably. Furthermore, a polypeptide of the invention does not necessarily confer complete pathogen resistance, for example when some symptoms still occur or there is some pathogen reproduction on infection but at a reduced amount. Enhanced resistance can be determined by a number of methods known in the art such as analysing the plants for the amount of pathogen and/or analysing plant growth or the amount of damage or disease symptoms to a plant in the presence of the pathogen, and comparing one or more of these parameters to an isogenic plant lacking an exogenous gene encoding a polypeptide of the invention.

By "substantially purified polypeptide" or "purified polypeptide" we mean a polypeptide that has generally been separated from the lipids, nucleic acids, other peptides, and other contaminating molecules with which it is associated in its native state. Preferably, the substantially purified polypeptide is at least 90% free from other components with which it is naturally associated.

Transgenic plants and host cells of the invention may comprise an exogenous polynucleotide encoding a polypeptide of the invention. In these instances, the plants and cells produce a recombinant polypeptide. The term "recombinant" in the context of a polypeptide refers to the polypeptide encoded by an exogenous polynucleotide when produced by a cell, which polynucleotide has been introduced into the cell or a progenitor cell by recombinant DNA or RNA techniques such as, for example, transformation. Typically, the cell comprises a non-endogenous gene that causes an altered amount of the polypeptide to be produced. In an embodiment, a "recombinant polypeptide" is a polypeptide made by the expression of an exogenous (recombinant) polynucleotide in a plant cell.

The terms "polypeptide" and "protein" are generally used interchangeably.

The % identity of a polypeptide is determined by GAP (Needleman and Wunsch, 1970) analysis (GCG program) with a gap creation penalty=5, and a gap extension penalty=0.3. The query sequence is at least 150 amino acids in length, and the GAP analysis aligns the two sequences over a region of at least 150 amino acids. More preferably, the query sequence is at least 500 amino acids in length, and the GAP analysis aligns the two sequences over a region of at least 500 amino acids. More preferably, the query sequence is at least 750 amino acids in length and the GAP analysis aligns the two sequences over a region of at least 750 amino acids. Even more preferably, the query sequence is at least 900 amino acids in length and the GAP analysis aligns the two sequences over a region of at least 900 amino acids. Even more preferably, the GAP analysis aligns two sequences over their entire length.

As used herein a "biologically active" fragment is a portion of a polypeptide of the invention which maintains a defined activity of the full-length polypeptide such as when expressed in a plant, such as wheat, confers (enhanced) resistance to stem rust, preferably wheat stem rust such as the Ug99 group of races of *Puccinia graminis* f. sp. *tritici* when compared to an isogenic plant not expressing the polypeptide. Biologically active fragments can be any size as long as they maintain the defined activity but are preferably at least 750 or at least 900 amino acid residues long. Preferably, the biologically active fragment maintains at least 10%, at least 50%, at least 75% or at least 90%, of the activity of the full length protein.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 60%, more preferably at least 65%, more preferably at least 70%, more preferably at least 75%, more preferably at least 76%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics. Preferred amino acid sequence mutants have only one, two, three, four or less than 10 amino acid changes relative to the reference wildtype polypeptide.

Mutant (altered) polypeptides can be prepared using any technique known in the art, for example, using directed evolution or rational design strategies (see below). Products derived from mutated/altered DNA can readily be screened using techniques described herein to determine if they confer resistance to *Puccinia graminis* (for example, a race of the Ug99 group of *Puccinia graminis* f sp. *tritici*) such as by producing a transgenic plant expressing the mutated/altered DNA and determining the ability of the plant to produce grain in the presence of the pathogen.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. In order to maintain activity, sites of interest include those not in an active site, such as a CC, BD or LRR domain, and those which are not highly conserved between different species. These sites, especially those falling within a sequence of at least three other non-conserved sites can generally be substituted in a relatively conservative or non-conservative manner. Examples of conservative substitutions are shown in Table 1 under the heading of "exemplary substitutions".

TABLE 1

Exemplary substitutions.

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |

TABLE 1-continued

| Exemplary substitutions. | |
|---|---|
| Original Residue | Exemplary Substitutions |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

In a preferred embodiment a mutant/variant polypeptide has one or two or three or four conservative amino acid changes when compared to a naturally occurring polypeptide. Details of conservative amino acid changes are provided in Table 1. In a preferred embodiment, the changes are not in one or more of the motifs which are highly conserved between the different polypeptides provided herewith. As the skilled person would be aware, such minor changes can reasonably be predicted not to alter the activity of the polypeptide when expressed in a recombinant cell.

In an embodiment, the protein of the invention is a CC-NB-LRR plant pathogen resistance gene which comprises domains configured as shown in FIG. 4.

The primary amino acid sequence of a polypeptide of the invention can be used to design variants/mutants thereof based on comparisons with closely related resistance polypeptides comprising NB and LRR domains, more preferably CC, NB and LRR domains. As the skilled addressee will appreciate, residues highly conserved amongst closely related CC-NB-LRR proteins are less likely to be able to be altered, especially with non-conservative substitutions, and activity maintained than less conserved residues (see above).

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. The polypeptides may be post-translationally modified in a cell, for example by phosphorylation, which may modulate its activity. These modifications may serve to increase the stability and/or bioactivity of the polypeptide of the invention.

Directed Evolution

In directed evolution, random mutagenesis is applied to a protein, and a selection regime is used to pick out variants that have the desired qualities, for example, increased activity. Further rounds of mutation and selection are then applied. A typical directed evolution strategy involves three steps:

1) Diversification: The gene encoding the protein of interest is mutated and/or recombined at random to create a large library of gene variants. Variant gene libraries can be constructed through error prone PCR (see, for example, Leung, 1989; Cadwell and Joyce, 1992), from pools of DNaseI digested fragments prepared from parental templates (Stemmer, 1994a; Stemmer, 1994b; Crameri et al., 1998; Coco et al., 2001) from degenerate oligonucleotides (Ness et al., 2002, Coco, 2002) or from mixtures of both, or even from undigested parental templates (Zhao et al., 1998; Eggert et al., 2005; Jezequek et al., 2008) and are usually assembled through PCR. Libraries can also be made from parental sequences recombined in vivo or in vitro by either homologous or non-homologous recombination (Ostermeier et al., 1999; Volkov et al., 1999; Sieber et al., 2001). Variant gene libraries can also be constructed by sub-cloning a gene of interest into a suitable vector, transforming the vector into a "mutator" strain such as the *E. coli* XL-1 red (Stratagene) and propagating the transformed bacteria for a suitable number of generations. Variant gene libraries can also be constructed by subjecting the gene of interest to DNA shuffling (i.e., in vitro homologous recombination of pools of selected mutant genes by random fragmentation and reassembly) as broadly described by Harayama (1998).

2) Selection: The library is tested for the presence of mutants (variants) possessing the desired property using a screen or selection. Screens enable the identification and isolation of high-performing mutants by hand, while selections automatically eliminate all nonfunctional mutants. A screen may involve screening for the presence of known conserved amino acid motifs. Alternatively, or in addition, a screen may involve expressing the mutated polynucleotide in a host organism or part thereof and assaying the level of activity.

3) Amplification: The variants identified in the selection or screen are replicated many fold, enabling researchers to sequence their DNA in order to understand what mutations have occurred.

Together, these three steps are termed a "round" of directed evolution. Most experiments will entail more than one round. In these experiments, the "winners" of the previous round are diversified in the next round to create a new library. At the end of the experiment, all evolved protein or polynucleotide mutants are characterized using biochemical methods.

Rational Design

A protein can be designed rationally, on the basis of known information about protein structure and folding. This can be accomplished by design from scratch (de novo design) or by redesign based on native scaffolds (see, for example, Hellinga, 1997; and Lu and Berry, Protein Structure Design and Engineering, Handbook of Proteins 2, 1153-1157 (2007)). Protein design typically involves identifying sequences that fold into a given or target structure and can be accomplished using computer models. Computational protein design algorithms search the sequence-conformation space for sequences that are low in energy when folded to the target structure. Computational protein design algorithms use models of protein energetics to evaluate how mutations would affect a protein's structure and function. These energy functions typically include a combination of molecular mechanics, statistical (i.e. knowledge-based), and other empirical terms. Suitable available software includes IPRO (Interative Protein Redesign and Optimization), EGAD (A Genetic Algorithm for Protein Design), Rosetta Design, Sharpen, and Abalone.

Polynucleotides and Genes

The present invention refers to various polynucleotides. As used herein, a "polynucleotide" or "nucleic acid" or "nucleic acid molecule" means a polymer of nucleotides, which may be DNA or RNA or a combination thereof, and includes genomic DNA, mRNA, cRNA, and cDNA. Less preferred polynucleotides include tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid". Preferred polynucleotides of the invention encode a polypeptide of the invention.

By "isolated polynucleotide" we mean a polynucleotide which has generally been separated from the polynucleotide sequences with which it is associated or linked in its native state, if the polynucleotide is found in nature. Preferably, the isolated polynucleotide is at least 90% free from other components with which it is naturally associated, if it is found in nature. Preferably the polynucleotide is not naturally occurring, for example by covalently joining two shorter polynucleotide sequences in a manner not found in nature (chimeric polynucleotide).

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "Sr33 gene" as used herein refers to a nucleotide sequence which is homologous to the isolated Sr33 gene (SEQ ID NO:5) or Sr33 cDNA (SEQ ID NO:3) described herein. As described herein, some alleles and variants of the Sr33 gene family encode a protein that confers resistance to stem rust (for example as caused by the Ug99 group of races of *Puccinia graminis* f. sp. *tritici*). Sr33 genes include the naturally occurring alleles or variants existing in cereals such as wheat. Nucleic acid molecules having the nucleotide sequence shown herein as SEQ ID NO:3 (cDNA) or SEQ ID NO:5 (genomic sequence), encoding a protein with amino acid sequence SEQ ID NO:1, are examples of an Sr33 gene which confers resistance to stem rust.

A genomic form or clone of a gene containing the transcribed region may be interrupted with non-coding sequences termed "introns" or "intervening regions" or "intervening sequences", which may be either homologous or heterologous with respect to the "exons" of the gene. An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or, preferably, for integration into the host genome.

As used herein, a "chimeric gene" refers to any gene that comprises covalently joined sequences that are not found joined in nature. Typically, a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule", "recombinant polynucleotide" or variations thereof refer to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations.

Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Furthermore, the term "exogenous" in the context of a polynucleotide (nucleic acid) refers to the polynucleotide when present in a cell that does not naturally comprise the polynucleotide. The cell may be a cell which comprises a non-endogenous polynucleotide resulting in an altered amount of production of the encoded polypeptide, for example an exogenous polynucleotide which increases the expression of an endogenous polypeptide, or a cell which in its native state does not produce the polypeptide. Increased production of a polypeptide of the invention is also referred to herein as "over-expression". An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components. The exogenous polynucleotide (nucleic acid) can be a contiguous stretch of nucleotides existing in nature, or comprise two or more contiguous stretches of nucleotides from different sources (naturally occurring and/or synthetic) joined to form a single polynucleotide. Typically such chimeric polynucleotides comprise at least an open reading frame encoding a polypeptide of the invention operably linked to a promoter suitable of driving transcription of the open reading frame in a cell of interest.

In an embodiment, if present in a wheat plant, or part (such a wheat grain) or cell thereof, the polynucleotide is not present on chromosome 1D and/or chromosome 7D of the genome.

The % identity of a polynucleotide is determined by GAP (Needleman and Wunsch, 1970) analysis (GCG program) with a gap creation penalty=5, and a gap extension penalty=0.3. The query sequence is at least 450 nucleotides in length, and the GAP analysis aligns the two sequences over a region of at least 450 nucleotides. Preferably, the query sequence is at least 1,500 nucleotides in length, and the GAP analysis aligns the two sequences over a region of at least 1,500 nucleotides. Even more preferably, the query sequence is at least 2,700 nucleotides in length and the GAP analysis aligns the two sequences over a region of at least 2,700 nucleotides. Even more preferably, the GAP analysis aligns two sequences over their entire length.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In a further embodiment, the present invention relates to polynucleotides which are substantially identical to those specifically described herein. As used herein, with reference to a polynucleotide the term "substantially identical" means the substitution of one or a few (for example 2, 3, or 4) nucleotides whilst maintaining at least one activity of the native protein encoded by the polynucleotide. In addition, this term includes the addition or deletion of nucleotides which results in the increase or decrease in size of the encoded native protein by one or a few (for example 2, 3, or 4) amino acids whilst maintaining at least one activity of the native protein encoded by the polynucleotide.

The present invention also relates to the use of oligonucleotides, for instance in methods of screening for a polynucleotide of, or encoding a polypeptide of, the invention. As used herein, "oligonucleotides" are polynucleotides up to 50 nucleotides in length. The minimum size of such oligonucleotides is the size required for the formation of a stable hybrid between an oligonucleotide and a complementary sequence on a nucleic acid molecule of the present invention. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length. Oligonucleotides of the present invention used as a probe are typically conjugated with a label such as a radioisotope, an enzyme, biotin, a fluorescent molecule or a chemiluminescent molecule.

The present invention includes oligonucleotides that can be used as, for example, probes to identify nucleic acid molecules, or primers to produce nucleic acid molecules. Probes and/or primers can be used to clone homologues of the polynucleotides of the invention from other species. Furthermore, hybridization techniques known in the art can also be used to screen genomic or cDNA libraries for such homologues.

Polynucleotides and oligonucleotides of the present invention include those which hybridize under stringent conditions to one or more of the sequences provided as SEQ ID NO's: 3 to 5 or 12. As used herein, stringent conditions are those that (1) employ low ionic strength and high temperature for washing, for example, 0.015 M NaCl/0.0015 M sodium citrate/0.1% $NaDodSO_4$ at 50° C.; (2) employ during hybridisation a denaturing agent such as formamide, for example, 50% (vol/vol) formamide with 0.1% bovine serum albumin, 0.1% Ficoll, 0.1% polyvinylpyrrolidone, 50 mM sodium phosphate buffer at pH 6.5 with 750 mM NaCl, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 g/ml), 0.1% SDS and 10% dextran sulfate at 42° C. in 0.2×SSC and 0.1% SDS.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid). A variant of a polynucleotide or an oligonucleotide of the invention includes molecules of varying sizes of, and/or are capable of hybridising to, the wheat genome close to that of the reference polynucleotide or oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

Nucleic Acid Constructs

The present invention includes nucleic acid constructs comprising the polynucleotides of the invention, and vectors and host cells containing these, methods of their production and use, and uses thereof. The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In preferred embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, such as a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of an organism such as a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of, for example, the plant, such as, for example, endosperm, embryo, leaves, fruit, tubers or root. In a preferred embodiment, a promoter is expressed selectively or preferentially in leaves and/or stems of a plant, preferably a cereal plant. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in, for example, a plant. Typically, the promoter is expressed at a level 10-fold higher in the specific tissue or organ than in other tissues or organs.

In an embodiment, the promoter is a stem-specific promoter or a promoter which directs gene expression in an aerial part of the plant (green tissue specific promoter) such as a ribulose-1,5-bisphosphate carboxylase oxygenase (RUBISCO) promoter.

Examples of stem-specific promoters include, but are not limited to those described in U.S. Pat. No. 5,625,136, and Bam et al. (2008).

The promoters contemplated by the present invention may be native to the host plant to be transformed or may be derived from an alternative source, where the region is functional in the host plant. Other sources include the *Agrobacterium* T-DNA genes, such as the promoters of genes for the biosynthesis of nopaline, octapine, mannopine, or other opine promoters, tissue specific promoters (see, e.g., U.S. Pat. No. 5,459,252 and WO 91/13992); promoters from viruses (including host specific viruses), or partially or wholly synthetic promoters. Numerous promoters that are functional in mono- and dicotyledonous plants are well known in the art (see, for example, Greve, 1983; Salomon et al., 1984; Garfinkel et al., 1983; Barker et al., 1983); including various promoters isolated from plants and viruses such as the cauliflower mosaic virus promoter (CaMV 35S, 19S). Non-limiting methods for assessing promoter activity are disclosed by Medberry et al. (1992, 1993), Sambrook et al. (1989, supra) and U.S. Pat. No. 5,164,316.

Alternatively or additionally, the promoter may be an inducible promoter or a developmentally regulated promoter which is capable of driving expression of the introduced polynucleotide at an appropriate developmental stage of the, for example, plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from an octopine synthase (ocs) gene or nopaline synthase (nos) gene of *Agrobacterium tumefaciens* (Bevan et al., 1983). Suitable 3' non-translated sequences may also be derived from plant genes such as the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi (1987).

Vectors

The present invention includes use of vectors for manipulation or transfer of genetic constructs. By "chimeric vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP 256223; a glutamine synthetase gene conferring, upon overexpression, resistance to glutamine synthetase inhibitors such as phosphinothricin as, for example, described in WO 87/05327, an acetyltransferase gene from *Streptomyces viridochromogenes* conferring resistance to the selective agent phosphinothricin as, for example, described in EP 275957, a gene encoding a 5-enolshikimate-3-phosphate synthase (EPSPS) conferring tolerance to N-phosphonomethylglycine as, for example, described by Hinchee et al. (1988), a bar gene conferring resistance against bialaphos as, for example, described in WO91/02071; a nitrilase gene such as bxn from *Klebsiella ozaenae* which confers resistance to bromoxynil (Stalker et al., 1988); a dihydrofolate reductase (DHFR) gene conferring resistance to methotrexate (Thillet et al., 1988); a mutant acetolactate synthase gene (ALS), which confers resistance to imidazolinone, sulfonylurea or other ALS-inhibiting chemicals (EP 154,204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., 1985), which may be employed in calcium-sensitive bioluminescence detection; a green fluorescent protein gene (Niedz et al., 1995) or derivatives thereof; a luciferase (luc) gene (Ow et al., 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Preferably, the nucleic acid construct is stably incorporated into the genome of, for example, the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The level of a protein of the invention may be modulated by increasing the level of expression of a nucleotide sequence that codes for the protein in a plant cell, or decreasing the level of expression of a gene encoding the protein in the plant, leading to modified pathogen resistance. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of pathogen resistance or other phenotype. Alternatively, a population of mutagenized seed or a population of plants from a breeding program may be screened for individual lines with altered pathogen resistance or other phenotype associated with pathogen resistance.

Recombinant Cells

Another embodiment of the present invention includes a recombinant cell comprising a host cell transformed with one or more recombinant molecules of the present invention, or progeny cells thereof. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a nucleic acid construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants".

A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "compared to an isogenic plant", or similar phrases, refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein.

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein defined herein in the desired plant or plant organ. Transgenic plant parts include all parts and cells of said plants comprising the transgene such as, for example, cultured tissues, callus and protoplasts.

Plants contemplated for use in the practice of the present invention include both monocotyledons and dicotyledons. Target plants include, but are not limited to, the following: cereals (for example, wheat, barley, rye, oats, rice, maize, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat, rice, maize, triticale, oats or barley, even more preferably wheat.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. A preferred species of hexaploid wheat is *T. aestivum* ssp *aestivum* (also termed "breadwheat"). Tetraploid wheat includes *T. durum* (also referred to herein as durum wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-*Triticum* species (such as rye [*Secale cereale*]), including but not limited to Triticale.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

As used herein, the "other genetic markers" may be any molecules which are linked to a desired trait of a plant. Such markers are well known to those skilled in the art and include molecular markers linked to genes determining traits such disease resistance, yield, plant morphology, grain quality, dormancy traits, grain colour, gibberellic acid content in the seed, plant height, flour colour and the like. Examples of such genes are the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance.

Four general methods for direct delivery of a gene into cells have been described: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. No. 4,945,050 and U.S. Pat. No. 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011); Brassica (U.S. Pat. No. 5,463,174); peanut (Cheng et al., 1996); and pea (Grant et al., 1995).

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. No. 5,589,617, U.S. Pat. No. 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Sr33 allele or variant that confers enhanced resistance to stem rust to the plant, allows rapid selection of plants carrying the desired trait, which may be nurtured to maturity in the greenhouse or field for subsequent further backcrossing to the recurrent parent.

Any molecular biological technique known in the art can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al., 2001). The invention also includes the use of molecular marker techniques to detect polymorphisms linked to alleles of the (for example) Sr33 gene which confers enhanced resistance to stem rust. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

In an embodiment, a linked loci for marker assisted selection is at least within 1 cM, or 0.5 cM, or 0.1 cM, or 0.01 cM from a gene encoding a polypeptide of the invention.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a Sr33 gene or allele which confers enhanced resistance to stem rust. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

TILLING

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf (2005), and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencher software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Plant/Grain Processing

Grain/seed of the invention, preferably cereal grain and more preferably wheat grain, or other plant parts of the invention, can be processed to produce a food ingredient, food or non-food product using any technique known in the art.

In one embodiment, the product is whole grain flour such as, for example, an ultrafine-milled whole grain flour, or a flour made from about 100% of the grain. The whole grain flour includes a refined flour constituent (refined flour or refined flour) and a coarse fraction (an ultrafine-milled coarse fraction).

Refined flour may be flour which is prepared, for example, by grinding and bolting cleaned grain such as wheat or barley grain. The particle size of refined flour is described as flour in which not less than 98% passes through a cloth having openings not larger than those of woven wire cloth designated "212 micrometers (U.S. Wire 70)". The coarse fraction includes at least one of: bran and germ. For instance, the germ is an embryonic plant found within the grain kernel. The germ includes lipids, fiber, vitamins, protein, minerals and phytonutrients, such as flavonoids. The bran includes several cell layers and has a significant amount of lipids, fiber, vitamins, protein, minerals and phytonutrients, such as flavonoids. Further, the coarse fraction may include an aleurone layer which also includes lipids, fiber, vitamins, protein, minerals and phytonutrients, such as flavonoids. The aleurone layer, while technically considered part of the endosperm, exhibits many of the same characteristics as the bran and therefore is typically removed with the bran and germ during the milling process. The aleurone layer contains proteins, vitamins and phytonutrients, such as ferulic acid.

Further, the coarse fraction may be blended with the refined flour constituent. The coarse fraction may be mixed with the refined flour constituent to form the whole grain flour, thus providing a whole grain flour with increased nutritional value, fiber content, and antioxidant capacity as compared to refined flour. For example, the coarse fraction or whole grain flour may be used in various amounts to replace refined or whole grain flour in baked goods, snack products, and food products. The whole grain flour of the present invention (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In further embodiments, enzymes found within the bran and germ of the whole grain flour and/or coarse fraction are inactivated in order to stabilize the whole grain flour and/or coarse fraction. Stabilization is a process that uses steam, heat, radiation, or other treatments to inactivate the enzymes found in the bran and germ layer. Flour that has been stabilized retains its cooking characteristics and has a longer shelf life.

In additional embodiments, the whole grain flour, the coarse fraction, or the refined flour may be a component (ingredient) of a food product and may be used to product a food product. For example, the food product may be a bagel, a biscuit, a bread, a bun, a croissant, a dumpling, an English muffin, a muffin, a pita bread, a quickbread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In alternative embodiments, the whole grain flour, refined flour, or coarse fraction may be a component of a nutritional supplement. For instance, the nutritional supplement may be a product that is added to the diet containing one or more additional ingredients, typically including: vitamins, minerals, herbs, amino acids, enzymes, antioxidants, herbs, spices, probiotics, extracts, prebiotics and fiber. The whole grain flour, refined flour or coarse fraction of the present invention includes vitamins, minerals, amino acids, enzymes, and fiber. For instance, the coarse fraction contains a concentrated amount of dietary fiber as well as other essential nutrients, such as B-vitamins, selenium, chromium, manganese, magnesium, and antioxidants, which are essential for a healthy diet. For example 22 grams of the coarse fraction of the present invention delivers 33% of an individual's daily recommend consumption of fiber. The nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. The supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage, this embodiment may be particularly attractive as a fiber supplement for children.

In an additional embodiment, a milling process may be used to make a multi-grain flour or a multi-grain coarse fraction. For example, bran and germ from one type of grain may be ground and blended with ground endosperm or whole grain cereal flour of another type of cereal. Alternatively bran and germ of one type of grain may be ground and blended with ground endosperm or whole grain flour of another type of grain. It is contemplated that the present invention encompasses mixing any combination of one or more of bran, germ, endosperm, and whole grain flour of one or more grains. This multi-grain approach may be used to make custom flour and capitalize on the qualities and nutritional contents of multiple types of cereal grains to make one flour.

It is contemplated that the whole grain flour, coarse fraction and/or grain products of the present invention may be produced by any milling process known in the art. An exemplary embodiment involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like. After grinding, the grain is discharged and conveyed to a sifter. Further, it is contemplated that the whole grain flour, coarse fraction and/or grain products of the present invention may be modified or enhanced by way of numerous other processes such as: fermentation, instantizing, extrusion, encapsulation, toasting, roasting, or the like.

Malting

A malt-based beverage provided by the present invention involves alcohol beverages (including distilled beverages) and non-alcohol beverages that are produced by using malt as a part or whole of their starting material. Examples include beer, happoshu (low-malt beer beverage), whisky, low-alcohol malt-based beverages (e.g., malt-based beverages containing less than 1% of alcohols), and non-alcohol beverages.

Malting is a process of controlled steeping and germination followed by drying of the grain such as barley and wheat grain. This sequence of events is important for the synthesis of numerous enzymes that cause grain modification, a process that principally depolymerizes the dead endosperm cell walls and mobilizes the grain nutrients. In the subsequent drying process, flavour and colour are produced due to chemical browning reactions. Although the primary use of malt is for beverage production, it can also be utilized in other industrial processes, for example as an enzyme source in the baking industry, or as a flavouring and colouring agent in the food industry, for example as malt or as a malt flour, or indirectly as a malt syrup, etc.

In one embodiment, the present invention relates to methods of producing a malt composition. The method preferably comprises the steps of:

(i) providing grain, such as barley or wheat grain, of the invention, (ii) steeping said grain, (iii) germinating the steeped grains under predetermined conditions and (iv) drying said germinated grains.

For example, the malt may be produced by any of the methods described in Hoseney (Principles of Cereal Science and Technology, Second Edition, 1994: American Association of Cereal Chemists, St. Paul, Minn.). However, any other suitable method for producing malt may also be used with the present invention, such as methods for production of specialty malts, including, but limited to, methods of roasting the malt.

Malt is mainly used for brewing beer, but also for the production of distilled spirits. Brewing comprises wort production, main and secondary fermentations and post-treatment. First the malt is milled, stirred into water and heated. During this "mashing", the enzymes activated in the malting degrade the starch of the kernel into fermentable sugars. The produced wort is clarified, yeast is added, the mixture is fermented and a post-treatment is performed.

EXAMPLES

Example 1. Genetic Mapping of Sr33

A wheat accession CS1D5405 was obtained that contains the Sr33 gene—CS1D5405 is a single chromosome substitution genetic stock which has chromosome 1D of the reference wheat genotype Chinese Spring (CS) replaced by the corresponding chromosome from an *Aegilops tauschii* accession (RL5288), the donor of Sr33. Wheat leaves were infected with stem rust *Puccinia graminis* f. sp. *tritici* pathotype 34-1,2,3,4,5,6,7,11 (Plant Breeding Institute culture no. 171, Cobbity, New South Wales, Australia) and examined histologically to compare the Sr33 resistance response to that conferred by a strong responsive gene, Sr45, also derived from *Ae. tauschii* and introgressed into hexaploid wheat. In the hexaploid wheat leaves collected 5 days post inoculation (dpi), larger infection sites were observed in Sr33 containing plants compared to infected plants containing the Sr45 gene.

To investigate the potential mode of action of these two different resistance genes, stained, rust infected leaf tissue was further cleared and cell death identified by autofluorescence. Rust infected leaf tissues were cleared and stained with wheat germ agglutinin (WGA) conjugated to FITC as described in Ayliffe et al. (2011). To visualise autofluorescent cells, the same leaf samples were cleared in a saturated chloral hydrate solution and observed under UV light. Hexaploid wheats containing Sr33 showed little autofluorescence due to plant cell death at rust infection sites as compared to Sr45 showing strong hypersensitive cell death. Further tests with a Ug99 stem rust isolate and derived races as well as North American (Rouse et al., 2011) and Australian stem rust isolates showed that the presence of Sr33 in CS1D5405 conferred an intermediate resistance phenotype compared with the Sr45 gene in the Chinese Spring genetic background.

A genetic mapping approach was carried out to locate the Sr33 gene, as follows. A mapping population was generated from a cross between a resistant plant CS1D5405 which contained Sr33 (Jones et al., 1991) and a plant of the susceptible variety Chinese Spring which lacks Sr33. The mapping population included 85 recombinant inbred lines (RIL) and 1150 F2 lines derived from the cross between CS1D5405 and Chinese Spring. Rust screening of these plant materials was done using *Puccinia graminis* f. sp. *tritici* pathotype 34-1,2,3,4,5,6,7,11 (Plant Breeding Institute culture no. 171, Cobbity, New South Wales, Australia) and the method of Bariana and McIntosh (1993). Along with CS1D5405, *Ae. tauschii* accession CPI110799 (the original donor of Sr33) was also used as positive control. Stem rust resistance segregated as a single, co-dominant gene at the Sr33 locus in the recombinant inbred family.

Simple sequence repeat (SSR) markers specific to Chromosome 1D (Somers et al., 2004) were screened on the 85 RILs using the method of Hayden et al. (2008) and 11 polymorphic markers identified were mapped on the RIL populations using MAP MANAGER Version QTXb20 (Manly et al., 2001) and Kosambi (1944) map function. Two closely linked flanking markers, namely BE405778 and BE499711, were identified from this screening and used to identify recombinants from the large F2 population in this positional mapping strategy using the method described in Kota et al. (2006). About 2850 gametes in the genetic mapping population of CS1D5405×CS were analysed using flanking EST derived markers BE405778 and BE499711 in the region containing Sr33. This identified 30 independent recombinant lines which each had a recombination between the two markers.

To identify additional markers in the Sr33 region, wheat expressed sequence tags (wEST) specific to chromosome group 1 (Akhunov et al., 2010) were screened following the method of Lagudah et al. (2006). Furthermore, AFLP analysis was done using 408 primer combinations derived from 17 PstI and 24 MseI selective amplification primers and methods as described in Mago et al. (2002).

To initiate physical mapping of the Sr33 region, the D genome specific BAC libraries made from *Ae. tauschii* accession AL8/78 (Luo et al., 2003) and AUS18913 (Moullet et al., 1999) were screened according to Lagudah et al. (2006). A closely linked AFLP-derived marker located within 0.04 cM of Sr33 that contained sequences of a dehydrin gene was used as a probe on the D genome BAC library made from *Ae. tauschii* accession AL8/78, and positive clones were identified. Identified BACs were mapped using the isolated low copy sequences as described in Lagudah et al. (2006). Positive BAC clones were sequenced at Beijing Genomic Institute, China and at Integrated Genomics facility, Kansas State University, USA. Contigs of the positive clones were identified from the *Ae. tauschii* Physical Mapping Project, UC Davis, USA. Repeat sequences present in the assembled short contigs within the BACs were masked using the wheat repeats database (http://wheat.pw.usda.gov/ITMI/Repeats/blastrepeats3.html) and the non-repeat sequences were analysed for genes using the gene prediction software of Massachusetts Institute of Technology (http://genes.mit.edu). A BAC contig, ctg4713, was identified which carried additional sequences encoding a Pum/Mpt5/FBF-like gene (designated Bpm) and a resistance gene analog (RGA) with a coiled coil nucleotide binding leucine rich repeat (CC-NB-LRR) domains designated AetRGA1a (see FIG. 4).

The dehydrin, Bpm and AetRGA1a sequences each had orthologous gene members in barley and *Triticum monococcum* (Wei et al., 2002; Jordan et al., 2011) associated with clusters of defense related genes and mapped at corresponding homoeologous positions on chromosomes 1H and 1A, respectively. In the high resolution genetic map, AetRGA1a was mapped proximally at the same position as the dehydrin and Bpm sequences (FIG. 1).

Re-screening of the BAC library with AetRGA1a as a probe further identified sequence contig 5455 which contained three additional closely related RGA members (designated as AetRGA1b, AetRGA1c and AetRGA1d) that were genetically mapped as co-segregating with Sr33 (FIG. 1). Subsequent screening of a second BAC library from *Ae. tauschii* accession AUS18913 (Moullet et al., 1999), which was geographically closer and located within the same genepool as the original source of the Sr33 donor, revealed four more co-segregating RGA sequences (FIG. 1). These were designated AetRGA1e, AetRGA1f and two other dissimilar RGA types, AetRGA2a and AetRGA3a (FIG. 1). AetRGA1f and AetRGA3a each had in-frame stop codons and were considered to be non-functional and therefore pseudogenes that were also present in Sr33 carrying plants.

The three RGA classes, RGA1, RGA2 and RGA3 at the Sr33 locus showed close resemblance to the three non-cross hybridizing NB-LRR genes, RGH1, RGH2 and RGH3 respectively at the barley Mla locus (Wei et al., 2002). AetRGA2a shows a unique gene fusion with a C-terminal region that contains an exocyst 70 subunit domain (FIG. 3) that is absent in barley. The barley Mla locus also contains members of a chymotrypsin inhibitor (CI) gene family, of which sequences related to the CI2e gene member found in *Ae. tauschii* was mapped distal to Sr33 at a distance of 0.3 cM (FIG. 1). The marker sequences from wheat were also compared to the rice and *Brachypodium* genomic sequences using Phytozome platform (www.phytozome.net), to identify orthologous sequences. This analysis using the Bpm and CI sequences identified orthologous regions in chromosomes 2 and 5 of the *Brachypodium* and rice genomes, respectively. However, these genomes were devoid of any of the three RGA classes found in *Ae. tauschii*, wheat and barley (FIG. 1).

The inventors concluded that there were at least 8 candidate LRR-NBS type genes in the mapped region, any of which could be Sr33, if indeed the Sr33 resistant phenotype were conferred by a single gene and if the Sr33 gene encoded an LRR-NBS type polypeptide.

Example 2. Mutagenesis and Isolation of Sr33 Mutants

To identify which of the candidate genes was Sr33, if indeed any of them were, a mutational approach was performed. Mutant lines were generated from ethyl methyl sulphonate (EMS) treatment of 2000 seeds of CS1D5405 (Mago et al., 2005). 850 M2 plants from the mutagenised lines were challenged with rust strain of pathotype 34-1,2, 3,4,5,6,7,11 to screen their Sr33 phenotype. Nine susceptible mutants were identified from the EMS treated population and used to identify the gene member responsible for stem rust resistance function as follows.

Based on chromosome 1D specific markers, four of the mutants (E1 to E4; Group I) were identified to carry large deletions in chromosome 1D while one mutant (E5; Group II) had a short deletion with the loss of the AetRGA1b, AetRGA1c, AetRGA1e, AetRGA2a and AetRGA3a genes (FIG. 2). These five mutants were not useful in identifying the Sr33 gene. In contrast, the remaining 4 mutant plants (E6 to E9; Group III) were identified as putative point mutants as no DNA marker loss was detected. Overlapping primer pairs (Table 2) designed along the entire length of the predicted genes were used to amplify the sequences from CPI110799 (Sr33 donor line) and the Group III susceptible mutants following the PCR method described by Lagudah et al. (2009).

Amplified sequences were compared for nucleotide variations using multiple sequence alignment (CLUSTAL-European Bioinformatics Institute-http://www.edi.ac.uk/Tools/sequence.html). Comparisons of the nucleotide sequences of the amplified portions of the AetRGA1a, AetRGA1b, AetRGA1c, AetRGA1d, AetRGA1f AetRGA2a and AetRGA3a genes with the corresponding sequences from the resistant parent CS1D5405 showed that they were 100% identical, while the nucleotide sequence of AetRGA1e showed independent nucleotide changes in the susceptible mutants. The inventors concluded that AetRGA1e was the Sr33 gene. Two of the mutant plants comprised nucleotide changes which resulted in amino acid changes in the P-loop of the encoded polypeptides, while the other two had mutations in sequences encoding the RNBS-B and GLPL motifs of the NBS domain, respectively (FIG. 4).

Complementation Analysis of Sr33

To further validate AetRGA1e as sufficient for Sr33 resistance, a genetic complementation test was performed using an 8 kb length of genomic DNA comprising of all the exons and introns and the 2.4 kb upstream and 1.5 kb downstream regions of AetRGA1e. The inventors expected this fragment to include the full length of the gene including its promoter. The 8 kb fragment was amplified using primers (5'-TTCAAGATGTCAAATTTTAAAAGGGC-3') (SEQ ID NO:13), (5'-CTACTCATTAGGAACTCGAGCGG-3') (SEQ ID NO:14) and the Phusion High-Fidelity DNA Polymerase (New England Biolabs Inc.) under the manufacturer's recommended conditions. The Sr33 gene fragment was inserted into the binary vector pVecNeo, a derivative of pWBvec8 (Wang et al., 1998) in which the 35S hygromycin gene has been replaced with a 35S NPTII selectable marker gene derived from pCMneoSTL2 (Maas et al., 1997). The genetic construct comprising the AetRGA1e gene sequence was introduced into the stem rust susceptible wheat cultivar Fielder by transformation using the *Agrobacterium tumefaciens* strain GV3101(pMP90). More than twenty $T_0$ transformants were tested for resistance response to the rust. The infection tests showed that twenty independent AetRGA1e transgenic plants exhibited stem rust infection response typical of Sr33 resistance while sib lines that lacked the transgene were highly susceptible, confirming that AetRGA1e conferred Sr33 resistance. The inventors concluded that the AetRGA1e gene was necessary and sufficient to confer the Sr33 phenotype.

TABLE 2

Primer sequences of used to isolate gene specific sequence.

| Gene | Primer Pair | Primer Sequence 5'-3' (Forward) | SEQ ID NO | Primer Sequence 5'-3' (Reverse) | SEQ ID NO |
|---|---|---|---|---|---|
| AetRGA1a | AtM1 F1 R1 | CTGCGCGCGTGGTTGGC | (SEQ ID NO: 15) | GATCGATAACAACTGCTTCCC | (SEQ ID NO: 41) |
| | AtM1 F2 R2 | GATCGGAATCGGATAGGGC | (SEQ ID NO: 16) | AATGGTTAGGTAGATCTATTGG | (SEQ ID NO: 42) |
| | AtM1 F3 R3 | AGCAGAATATACTCGAAAGGG | (SEQ ID NO: 17) | CTCCCTCAGCCTTGCCAG | (SEQ ID NO: 43) |
| | AtM1 F4 R4 | TTAATCTACCTAAATGTTTCTCC | (SEQ ID NO: 18) | CAGTGAAATTAGCGTGCAGC | (SEQ ID NO: 44) |
| AetRGA1b | AtM2 F1 R1 | TCTTCTTCTTCCACACTGGG | (SEQ ID NO: 19) | CCAAATCCAACAATGGAGACC | (SEQ ID NO: 45) |
| | AtM2 F2 R2 | AGCTTTGTACGCAGAAGCAAC | (SEQ ID NO: 20) | ATGAATGAAACAAGAAGTACTTC | (SEQ ID NO: 46) |
| | AtM2 F3 R3 | CCTAGAGAACAAAAGGTATGC | (SEQ ID NO: 21) | CAAAACTCAGAGCTATATGAAC | (SEQ ID NO: 47) |
| | AtM2 F4 R4 | TTTATTCAGATTGTTTATCATCTG | (SEQ ID NO: 22) | AAGCATGTACCTGGCCTAGATC | (SEQ ID NO: 48) |
| | AtM2 F5 R5 | TCCAGAAGATAGCATGATTGC | (SEQ ID NO: 23) | AGGAGTTGGAACCACCTTAG | (SEQ ID NO: 49) |
| | AtM2 F6 R6 | TGTTGGATCTTGGAGACAATTA | (SEQ ID NO: 24) | CAATACATATAAACGCAGACATC | (SEQ ID NO: 50) |
| | AtM2 F7 R7 | GAAGTAGTTAGGTTCAGCCTG | (SEQ ID NO: 25) | GCCAGCCGGTTGTGGCG | (SEQ ID NO: 51) |
| | AtM3 F1 R1 | CATATGGATGTGAAGGAGGC | (SEQ ID NO: 26) | TCTTGTTAGAGGCATCGTCG | (SEQ ID NO: 52) |
| AetRGA1c | AtM3 F2 R2 | GGCTTTGTACACAGAAGCTAC | (SEQ ID NO: 27) | TAAAACTGTGTGGATAGAACAG | (SEQ ID NO: 53) |
| | AtM3 F3 R3 | ATCCAAACATTTTACATTTCACC | (SEQ ID NO: 28) | AAGGTCTACACACATCACATAT | (SEQ ID NO: 54) |
| | AtM3 F4 R4 | ATTTATTCTTTTTTTGGAGGGCA | (SEQ ID NO: 29) | AAGCATATACCTGGCCTTTATA | (SEQ ID NO: 55) |
| | AtM3 F5 R5 | ATCCAGAAGATAGCAAGATTGA | (SEQ ID NO: 30) | AGATTCTGCAACACACCAGC | (SEQ ID NO: 56) |

TABLE 2-continued

Primer sequences of used to isolate gene specific sequence.

| Gene | Primer Pair | Primer Sequence 5'-3' (Forward) | SEQ ID NO | Primer Sequence 5'-3' (Reverse) | SEQ ID NO |
|---|---|---|---|---|---|
| | AtM3 F6 R6 | GGAGGTGTTGGATATTGGAAG | (SEQ ID NO: 31) | CAATACAACCAAACCTTGACATA | (SEQ ID NO: 57) |
| | AtM3 F7 R7 | GGAAAAAGTTGATTTCAGCCTT | (SEQ ID NO: 32) | CTAAAAGCCATTCACATTAACC | (SEQ ID NO: 58) |
| AetRGA1d | AtM4 F1 R1 | GGGCTTGGTCCAGATCCC | (SEQ ID NO: 33) | CACCCGCTGGCCACTAGTT | (SEQ ID NO: 59) |
| | AtM4 F2 R2 | CCATAAGAGAATATTTCCTGACGC | (SEQ ID NO: 34) | GAAAACACCAGCATGCCATGGG | (SEQ ID NO: 60) |
| AetRGA1e | AtMS F1 R1 | CTTGCCAACTCAGTTCCACC | (SEQ ID NO: 35) | TTGCATTATCATTCCGTGCAC | (SEQ ID NO: 61) |
| | AtM5 F2 R2 | CATATCGTACAATACATGCACC | (SEQ ID NO: 36) | TATTCTGAAGGGACAAGCGG | (SEQ ID NO: 62) |
| | AtM5 F3 R3 | ATGCTCCAGCCAATATATTCG | (SEQ ID NO: 37) | AGCACATCACACAACCTCTCGG | (SEQ ID NO: 53) |
| AetRGA1f | AtM6 F1 R1 | CTTGGATCAATGTTATTACTTCTCC | (SEQ ID NO: 38) | ACAAGCTGAGCTCTAGAAGATGG | (SEQ ID NO: 64) |
| AetRGA2a | AtM7 F1 R1 | GTTGAACTATCTTTCGAACTCG | (SEQ ID NO: 39) | TAAACAAACAACCTATCTGCGC | (SEQ ID NO: 65) |
| AetRGA3a | AtM8 F1 R1 | GGGTCCTGTACATTCCCTCGC | (SEQ ID NO: 40) | CTGGTTTATCCATCCGATCCACC | (SEQ ID NO: 66) |

Example 3. Structure of the Sr33 Gene and Polypeptide and its Expression

The genomic sequence of Sr33 has 6 exons and 5 introns as predicted through RT-PCR and 5' and 3' RACE (rapid amplification of cDNA ends) reactions. The structure of the gene is shown schematically in FIG. 4 and the gene sequence is provided as SEQ ID NO: 5. Exon 1 spans nucleotides 1226 to 1299, exon 2 spans nucleotides 1389 to 1511, exon 3 spans nucleotides 2238 to 3080, exon 4 spans nucleotides 4155 to 6157, exon 5 spans nucleotides 6266 to 6344 and exon 6 spans nucleotides 6824 to 7233, of SEQ ID NO: 5.

The pathogen resistant Sr33 polypeptide (SEQ ID NO:1 and SEQ ID NO:2) are an CC-NB-LRR containing polypeptide which has the following motifs; Coiled-coil, EDVID, hhGRExe, Walker A, Walker B, RNBS-B, RNBS-C, GLPL, RNBS-D, MHD and LRR. The coiled coil region generally extends from amino acid residues 1 to 160 of SEQ ID NO: 1. The NB domain generally extends from amino acid residues 161 to 550 of SEQ ID NO:1, whereas the LRR domain generally extends from amino acid residues 551 to 961 of SEQ ID NO:1.

Phylogenetic analysis by neighbour joining tree analysis showed that the encoded Sr33 polypeptide groups with the Mla proteins from the diploid A genome species, *Triticum monococcum* (TmMla) and barley (HvMla); the highest similarity of 86% was with TmMla while HvMla1 was the closet barley ortholog (FIG. 5). None of the isolated wheat leaf rust resistance genes encoding CC-NB-LRR proteins (Lr1, Lr10 and Lr21) were related to Sr33, exhibiting amino acid sequence identities ranged from 25% to 34%, or barley Mla members. AetRGA1e (Sr33) has 82, 81, 80, 78 and 30% identity with AetRGA1a, AetRGA1d, AetRGA1b, AetRGA1c and AetRGA2a respectively (Table 3).

TABLE 3

Percentage amino acid identity of wheat Sr33 to homologs of Sr33 from other plant species.

| SPECIES | ID or GenBank Accession No. | % Identity |
|---|---|---|
| *Ae. tauschii* acc. PI603225 | KF031297 | 99 |
| *Ae. tauschii* acc. AUS18913 | KF031284 | 99 |
| *Ae. tauschii* acc. CPI10908 | KF031298 | 97 |
| *Ae. tauschii* acc. AUS18911 | KF031299 | 96 |
| *T. monococcum* | ADX06722.1 | 86 |
| *Secale cereale* | BE587232.1 | 82 |
| *T. urartu* | EMS45849.1 | 80 |
| *Hordeum vulgare* | ACZ65501.1 | 80 |
| *Hordeum vulgare* | AAO16000.1 | 79 |
| *Hordeum vulgare* | ACZ65487.1 | 79 |

Example 4. Homologs of Sr33 in Other Plants

To determine the presence or absence of alleles of the Sr33 gene in diploid wheat plants and to identify variant alleles, plants were screened from each of 368 *Ae. tauschii* accessions collected from different geographical locations and maintained at the Australian Winter Cereals Collection in Tamworth, Australia, the Commonwealth Plant Introduction collection (CPI) at CSIRO Plant Industry, Australia and UC Davis, USA.

Full length sequences for alleles of Sr33 were obtained by PCR in plants from 36 accessions with no amplification product in the remaining 332 lines indicating that the latter accessions carried highly divergent sequences or lacked the gene. Haplotypes (FIG. 6, Table 4) based on the Sr33 sequence were grouped as follows based on the amino acid sequences, where the gene was present. Seven accessions possessed identical sequences (SEQ ID NO: 1) as the original Sr33 source and are classified as haplotype I. A second haplotype (haplotype II, SEQ ID NO:2) differed by a single amino acid from SEQ ID NO: 1 at position 588 (asparagine instead of aspartic acid), found in the accession PI603225. Sequences of 20 other accessions with 5 amino acid substitutions at the C terminus (LRR region) constitute haplotype III (SEQ ID NO:6). A fourth haplotype (SEQ ID NO:7) with several amino acid changes in both the NBS and LRR regions were found in three Russian accessions, while a fifth haplotype (SEQ ID NO:8) that encodes a truncated protein were found in five accessions of Iranian origin. Haplotypes I, II and III were found to originate from the southern coastal regions of the Caspian Sea. Plants from each of the haplotypes were screened for the Sr33 phenotype. Plants of haplotypes I and II showing resistance against multiple stem rust races (Table 4).

TABLE 4

Haplotypes of Sr33 and the details of *Ae. tauschii* accessions in each type given with stem rust response scores

| | | Rust response score* | | | | | | | |
|---|---|---|---|---|---|---|---|---|---|
| Haplotype | *Ae. tauschii* accession | 34-0 | 17-1, 2, 3, 4 | TRTTF | TTKSK | TTTTF | QTHJC | RKQQC | TPMKC |
| I | CPI110799 | ;1 | ;1 | —[a] | — | 22+ | 2 | ;2− | 2 |
| | CPI110659 | ; | 0; | ;, 2, 3, 3+ | ; | 2, 3, 3− | ;, 1 | ;, 1− | ;, 1 |
| | CPI110801 | ;1 | ;1 | | | | | | |
| | CPI110855 | 12− | 12− | 3, 3+ | 2− | 2−, 3 | 1 | ;, 1= | 1− |
| | CPI110818 | ;1− | ;1 | 1 | 1, 2− | 3 | 0 | 0 | 0; |
| | AUS18905 | ;1− | ;1 | — | — | — | — | — | — |
| | AUS18955 | | | | | | | | |
| | AUS18986 | | | | | | | | |
| II | PI603225 | | | | 2− | 22+ | 2 | 2− | 2 |

*Pathotypes 34-0 and 17-1234 are from Australia, TRTTF from Yemen, TTKSK (Ug99) from Kenya while TTTTF, QTHJC, RKQQC and TPMKC are from United States. Rust response data against TTKSK , TTTTF, QTHJC, RKQQC and TPMKC are from Rouse et al. (1) and Olson et al. (2).

[a]Data not available

Example 5. VIGS Analysis of Sr33 Function Indicates Resistance is Independent of RAR1, SGT1 and HSP90

Disease resistance mediated by a subset of NB-LRR type R proteins require the function of three chaperone proteins, namely RAR1, SGT1 and HSP90, that are thought to maintain and stabilize compatible proteins in an autoinactive state and promote proper immune function (Shirasu et al., 2009). Virus-induced gene silencing (VIGS) is a useful tool for targeted silencing of specific genes and is often employed to delineate protein function. Indeed, Scofield et al. (2005) demonstrated that attenuating the expression of the RAR1, SGT1, and HSP90 genes in hexaploid wheat was sufficient to compromise the immune capacity of the Lr21 gene. In order to ascertain if Sr33-mediated resistance was dependent on RAR1, SGT1, and HSP90, experiments were done to transiently silence the genes encoding these chaperones in the hexaploid wheat line CS1D5405 expressing Sr33, and the Sr33 phenotype assayed by resistance tests.

The silencing used viral vectors derived from a barley stripe mosaic virus (BSMV) vector obtained from Dr. Andrew O. Jackson at UC Berkeley (Petty et al., 1989). The BSMV γ vector was reconstructed to include a PCR-ready cloning site. To do this, the γ vector was digested with two restriction enzymes NotI and PacI, and ligated with a sequence of GGCCCCACTCATGACATGGCGTTAGCCATGGGAAGCTTGGAT (SEQ ID NO:67), which includes two XcmI restriction sites. The modified γ vector (named as γPCR vector) was linearized with restriction enzyme XcmI to produce a TA cloning site for direct cloning of PCR products. For simplicity, the BSMV-derived construct with no insert was named as γ00, and each BSMV silencing construct was named as γtarget. For example, a BSMV silencing construct carried a 185-bp fragment of the wheat PDS gene was named as γPDS.

The BSMV construct utilized to silence the Sr33 gene carried a 190-bp Sr33 gene specific fragment. Two constructs were prepared for silencing the Exo70 gene; each construct carried a 190-bp gene specific fragment from either the N or C terminus of the gene, named as γExo70N and γExo70C. In contrast, Rar1, Sgt1 and Hsp90 each had three homeologs on the A, B and D genomes of wheat. To silence all three homeologs in the genome, constructs were designed to carry an approximately 190-bp fragment whose nucleotide sequence was conserved in all three homeologs of each gene.

Infectious RNA transcripts were synthesized by in vitro transcription using T7 RNA polymerase (New England Biolabs, Ipswich, Mass.) from linearized α, β, and γ plasmids (Scofield et al., 2005). The BSMV inoculum was prepared with an equimolar ratio of α, β, and γ transcripts plus inoculation buffer containing a wounding agent. The inoculum was rub-inoculated onto the second leaf of each nine day old wheat seedling.

Stem rust assessments were conducted under a greenhouse condition with stem rust race QFCSC. The urediniospores were suspended in Soltrol 170 Isoparaffin (Chempoint, Bellevue, Wash.). The spore-inoculum density was calculated at 227,500 spores/ml using a Brightline hemocytometer as per the manufacturer's recommendations (Hausser Scientific, Horsham, Pa.). The inoculum was applied at a rate of 0.05 mg spores/10 ml Soltrol/plant using a Badger 350-3 airbrush gun (Badger Air-Brush Co., Franklin Park, Ill.). Spore germination rate was assessed on an inoculated microscope slide using a light microscope. A dew chamber with lighting was pre-conditioned to an air temperature of 19-22° C. and incubated for 24 h, followed by incubation under high humidity and light intensity conditions for at least 3 h before being transferred to a greenhouse. Assessments were made when Chinese Spring showed full susceptibility at 14 days post inoculation following the scale described in Bariana and McIntosh (1993).

Expression of the genes targeted for silencing was quantified by comparative quantitative real-time PCR (qRT-PCR). Transcript abundance was quantified via the iScript One-Step RT-PCR Kit with SYBR Green real time-PCR and quantified using the CFX96 real-time PCR detection system operated with the CFX Manager software (Bio-Rad, Hercules, Calif.). Transcript abundance was normalized to 18s and Actin transcript abundance and relative transcript abundance was calculated using the $\Delta\Delta C_t$ method as described in the CFX96 manual (Bio-Rad, Hercules, Calif.), where fold change=$2^{-\Delta\Delta Ct}$ and percent transcript abundance=fold change×100. Each reaction was conducted in a triplicate and data were used only if the $C_t \leq 30$ and the $C_t$ standard deviation between replicates was ≤0.3. The cycling conditions were as follows: 10 min at 50° C., 5 min at 95° C., followed by 40 cycles of 10 s at 95° C., 30 s at 55° C. and 1 min at 95° C., 1 min at 55° C., melt curve 55° C. to 95° C., increment 0.5° C. In all the cases, relative expression of the targeted gene was presented as the expression level of this gene in silenced plants relative to that of the same gene in plants infected with γ00, and the values of gene expression were the averages of three plants. For each PCR, the specificity of the amplifications was validated and the threshold cycle above background was calculated using Bio-Rad iCycler software. PCR efficiency was close to 100%. Relative quantification of the gene transcript abundances was calculated as described in Scofield et al. (2005). Error bars in all figures showing qRT-PCR data indicated the standard deviations calculated from the original CT (cycle threshold) values.

The primer sequences used to detect each gene were as follows:

```
SR33-F:
                                  (SEQ ID NO: 68)
5' GCAGGAGGACGTGGAAATC 3'

SR33-R:
                                  (SEQ ID NO: 69)
5' AAAGTCTACCATACAGCGGAAC 3'

Exo70-F:
                                  (SEQ ID NO: 70)
5' ATGGAGCAATGCCCAAAGT 3'

Exo70-R:
                                  (SEQ ID NO: 71)
5' GGCATCAGCAAACACCAACT 3'

HSP90-F:
                                  (SEQ ID NO: 72)
5' CGACCAGCACGCTCACGAT 3'

HSP90-R:
                                  (SEQ ID NO: 73)
5' GCGATGGTCCCGAGGTTGT3'

SGT1-F:
                                  (SEQ ID NO: 74)
5' CAAGCTGGGCAGTTAC 3'

SGT1-R:
                                  (SEQ ID NO: 75)
5' TCCTTCGATGCATAAAGC 3'

RAR1-F:
                                  (SEQ ID NO: 76)
5' ATGCGGTGCCAGCGAATA 3'

RAR1-R:
                                  (SEQ ID NO: 77)
5' GGGTTGTCGTCGTCGGTG 3'

Actin-F:
                                  (SEQ ID NO: 78)
5' AAATCTGGCATCACACTTTCTAC 3'

Actin-R:
                                  (SEQ ID NO: 79)
5' GTCTCAAACATAATCTGGGTCATC 3'
```

-continued

```
18SF:
                                  (SEQ ID NO: 80)
5' GTGACGGGTGACGGAGAATT 3'

18SR:
                                  (SEQ ID NO: 81)
5' GACACTAATGCGCCCGGTAT 3'

PDS-F:
                                  (SEQ ID NO: 82)
5' TGTCTTTAGCGTGCAAG 3'

PDS-R:
                                  (SEQ ID NO: 83)
5' GATGATTTCGGTGTCACT 3'
```

Silencing was confirmed through qRT-PCR analysis with data indicating a reduction in the relative expression of each gene (AetRGA1e, RAR1, SGT1 and HSP90) by an amount between 50-84% (Table 5). The silenced and control plants displayed an identical immune resistance capability, indicting Sr33-mediated resistance was independent of RAR1, SGT1 and HSP90 in these experiments in wheat. Moreover, as the BSMV:AetRGA1e treated plants displayed an increased susceptibility to stem rust infection, these data further validated the notion that this gene provided wheat with Sr33-dependent stem rust resistance. Silencing of the adjacent AetRGA2b member carrying the exocyst 70 subunit did not compromise resistance, indicating that that gene was not required for Sr33 mediated resistance.

TABLE 5 qRT-PCR analysis of Sr33, RGA2a + Exocyst70, RAR1, SGT1 and HSP90 expression during silencing by BSMV: VIGS

| Genes | Relative expression* | | | Average Relative Expression | SD |
|---|---|---|---|---|---|
| | Exp. 1 | Exp. 2 | Exp. 3 | | |
| Sr33 | 0.47 | 0.59 | 0.45 | 0.50 | 0.08 |
| RGA2a-N | 0.47 | 0.34 | 0.04 | 0.28 | 0.22 |
| RGA2a-C | 0.06 | 0.26 | 0.62 | 0.31 | 0.29 |
| RAR1 | 0.12 | 0.22 | 0.31 | 0.22 | 0.09 |
| HSP90 | 0.34 | 0.32 | 0.43 | 0.36 | 0.06 |
| SGT1 | 0.09 | 0.12 | 0.27 | 0.16 | 0.10 |

*Relative expression was calculated by dividing the expression value determined for the target gene in silenced plants by the expression value of the same gene measured in plants infected with Bsmv: 00.
*Each number is an average of triplicates.

Example 6. Yeast Two-Hybrid Analysis

The experiments described in Example 5 indicated that the Sr33 polypeptide functioned independently of the RAR1-SGT1-HSP90 chaperone complex. However, one caveat was that gene silencing is rarely complete. That is, the amount of RAR1, SGT1 and HSP90 protein during the VIGS experiment might not have been reduced sufficiently below a threshold to alter disease resistance. To assess whether Sr33 was able to interact with any of HSP90, SGT1 and RAR1 polypeptides in a second type of experiment, a directed yeast two-hybrid analysis was performed. Similar experiments were performed using WRKY1/2 polypeptide.

The yeast two-hybrid experiments were performed in *Saccharomyces cerevisiae* reporter strain Hf7c as follows. Public databases were scrutinized using *H. vulgare* HSP90, RAR1, SGT1, WRKY1/2 amino acid sequences as queries to isolate related expressed sequence tags (ESTs) derived from wheat. Using the available literature and sequence data, ESTs CK208966.1 and CJ619316.1 for SGT1, CJ684577.1 for RAR1, GQ240780.1 for HSP90, DR741433.1, BQ578389.1 for WRKY1 and DR740124.1, DR741886.1 for WRKY2 (Tai, 2008; Wang et al., 2011) were selected and primer pairings (Table 6) were developed for the isolation of the full-length cDNA of HSP90, RAR1, SGT1 and WRKY1/2 from *Ae. tauschii* line CPI110799.

The cDNAs of HSP90, SGT1, RAR1, WRKY1 and WRKY2 were amplified from plants from wheat line CPI110799 and barley (*H. vulgare*) variety Golden Promise. Target cDNA were obtained by PCR amplification using primers designed with specific restriction enzyme sites (Table 6) and cloned into pGADT7 (Clontech) at the corresponding sites. Yeast transformation was performed by the method of Gietz and Woods (2002) with co-transformants selected on SD media lacking leucine and tryptophan. The interaction analysis was performed on media lacking leucine, tryptophan and histidine with yeast grown at 30° C. for 3-4 days. As a positive control, the flax L6 TIR domain, which has been shown to homo-dimerize in yeast or the MLA10 CC1-46-HvWRKY1260-353 combination were used (Bernoux et al., 2011; Jordan et al., 2011). Total yeast protein was extracted in accordance with Kushnirov (2000). Proteins were separated by SDS-PAGE and transferred to a nitrocellulose membrane (Pall). Membranes were blocked in 5% skimmed milk and probed with anti-HA or anti-Myc mouse monoclonal antibodies (Roche), followed by goat anti-mouse antibodies conjugated with horseradish peroxidase (Pierce). Labelling was detected using the SuperSignal West Pico or Femto chemiluminescence kit (Pierce). Membranes were stained with Ponceau S to confirm equal loading.

Co-expression of full length Sr33 as bait with full length equivalents of *H. vulgare* or *Ae. tauchii* HSP90, SGT1 and RAR1 polypeptides failed to detect an interaction with Sr33. Structural evidence indicated that SGT1 may provide a docking interface by which compatible NB-LRR proteins associate with the chaperone complex (Zhang et al., 2010). Such an interaction had been validated experimentally with the observation that the LRR domain of two different NB-LRR type R proteins was able to interact directly with SGT1 (Bieri et al., 2004; Leister et al., 2005). In order to discount the possibility that steric hindrance might be a limiting factor in this study, the LRR domain of Sr33 was expressed as a truncated protein. Co-expression of LRR551-961 as bait with AetSGT1 as prey again yielded a negative interaction. Together with the VIGS analysis, these data provided strong genetic and biochemical evidence that Sr33 functioned independently of the chaperones HSP90, RAR1 and SGT1.

Yeast-2-Hybrid Analysis with WRKY1/2

The neighbor-joining analysis indicated that the Sr33 polypeptide amino acid sequence clustered with a cohort of barley Mla polypeptides. Given the degree of similarity between multiple barley Mla genes and TmMla1 with Sr33, a yeast-2-hybrid analysis was performed in order to assess whether Sr33 was able to interact with *H. vulgare* or *Ae. tauchii* equivalents of WRKY1/2.

The N-terminal coiled-coil domain (CC1-46) of HvMLA10 and TmMLA1 has been shown to be necessary and sufficient to mediate interaction with the C-terminal

TABLE 6

List of primers used to isolate cDNA of Sr33 from CPI110799 (*Ae. tauschii*) and cDNA of HSP90, RAR1, SGT1 and WRKY1/2 of CPI110799 and Golden Promise (*H. Vulgare L.*).

| Species | Designation | Oligonucleotide Sequence (5'-3') |
|---|---|---|
| *Ae. tauschii* | Sr33 FL Fwd EcoRI | ATGAATTCATGGATATT GTCACGGGTGCCATTG (SEQ ID NO: 84) |
| *Ae. tauschii* | Sr33 FL Rev SalI | ATGTCGACTCACTCTGC GTCAGAAATCGGTCCTC (SEQ ID NO: 85) |
| *Ae. tauschii* | Sr33 CC46 Rev SalI | ATGTCGACTCACGCAGC GTTCATGGTCTTGAG (SEQ ID NO: 86) |
| *Ae. tauschii* | Sr33 CC125 Rev SalI | ATGTCGACTCAGTCCTT GATCGCGTGAGCTATTC C (SEQ ID NO: 87) |
| *Ae. tauschii* | Sr33 CC160 Rev SalI | ATGTCGACTCATAGAGC ACGGAGACGAGGATCAA TTGC (SEQ ID NO: 88) |
| *Ae. tauschii* | Sr33 CC225 Rev SalI | ATGTCGACTCAGTGACA ATCAAAATCACCTTTAA TCTTCTCGTA (SEQ ID NO: 89) |
| *Ae. tauschii* | Sr33 LRR550 Fwd EcoRI | ATGAATTCATGCTCACA AATATCATGAGTATCTC ACAAGTGAGGT (SEQ ID NO: 90) |
| *H. vulgare L.* | RAR1 FL Fwd NdeI | ATCATATGTCGGCGGAG ACGGAGAGG (SEQ ID NO: 91) |
| *H. vulgare L.* | RAR1 FL Rev ClaI | GCATCGATTCACACAGC ATCAGCATTGTGCCA (SEQ ID NO: 92) |
| *Ae. tauschii* | RAR1 FL Fwd NdeI | ATGTCGGCGGAGACGGA GACG (SEQ ID NO: 93) |
| *Ae. tauschii* | RAR1 FL Rev ClaI | TAATCGATTCATACGGC ATCAGCATTGTGCCA (SEQ ID NO: 94) |
| *Ae. tauschii*/ *H. vulgare L.* | SGT1 FL Fwd EcoRI | ATGAATTCATGGCCGCC GCCGCC (SEQ ID NO: 95) |
| *Ae. tauschii*/ *H. vulgare L.* | SGT1 FL Rev ClaI | ATATCGATTTAATACTC CCACTTCTTGAGCTCCA TTCCA (SEQ ID NO: 96) |
| *Ae. tauschii*/ *H. vulgare L.* | HSP90 Fwd EcoRI | GCTATGAATTCATGGCG ACGGAGACCGAG (SEQ ID NO: 97) |
| *Ae. tauschii*/ *H. vulgare L.* | HSP90 Rev ClaI | GCATAATCGATTTAGTC GACCTCCTCCATCTTGC (SEQ ID NO: 98) |
| *H. vulgare L.* | WRKY1 FL Fwd EcoRI | ATGAATTCATGGATCCA TGGATGGGCAGCC (SEQ ID NO: 99) |
| *H. vulgare L.* | WRKY1 FL Rev ClaI | ATATCGATTTAATTGAT GTCCCTGGTCGGCGA (SEQ ID NO: 100) |

TABLE 6-continued

List of primers used to isolate cDNA of Sr33 from CPI110799 (*Ae. tauschii*) and cDNA of HSP90, RAR1, SGT1 and WRKY1/2 of CPI110799 and Golden Promise (*H. Vulgare L.*).

| Species | Designation | Oligonucleotide Sequence (5'-3') |
|---|---|---|
| *Ae. tauschii* | WRKY1 FL Fwd EcoRI | ATGAATTCATGGATCCA TGGGTCAGCAGCCA (SEQ ID NO: 101) |
| *Ae. tauschii* | WRKY1 FL Rev ClaI | ATATCGATTTAATTGAT GTCCCTGGTCGGCGATA (SEQ ID NO: 102) |
| *Ae. tauschii/ H. vulgare L.* | WRKY1260 Fwd EcoRI | ATGAATTCATGCCGCAG CAGCAGAACGACGG (SEQ ID NO: 103) |
| *H. vulgare L.* | WRKY2 FL Fwd EcoRI | ATGAATTCATGGAGGAG CAGTGGATGATCGGG (SEQ ID NO: 104) |
| *H. vulgare L.* | WRKY2 FL Rev ClaI | ATATCGATTCAAGCAAC AGGGATCCGACCAGA (SEQ ID NO: 105) |
| *H. vulgare L.* | WRKY2242 Fwd EcoRI | ATGAATTCATGCCGCCG CCCAAGCATCAAG (SEQ ID NO: 106) |
| *Ae. tauschii* | WRKY2 FL Fwd EcoRI | ATGAATTCATGGACGAG CAGTGGATGATCGGG (SEQ ID NO: 107) |
| *Ae. tauschii* | WRKY2 FL Rev ClaI | ATATCGATTCAAGCAAC AGGGATCCGACCAGAG (SEQ ID NO: 108) |
| *Ae. tauschii* | WRKY2246 Fwd EcoRI | ATGAATTCATGCCGCCG CCCAAGCAACAAG (SEQ ID NO: 109) |

domain (HvWRKY1260-353 and HvWRKY2242-319) of these WRKY proteins (Jordan et al., 2011; Shen et al., 2007; Maekawa et al., 2011). Accordingly, co-expression of Sr33 CC1-46 as bait with HvWRKY1260-353, HvWRKY2242-319 and AetWRKY1258-348 and AetWRKY2246-322 as prey failed to detect an interaction. This indicated that the Sr33 polypeptide functioned without needing to interact with WRKY1/2 polypeptide.

The CC Domain of Sr33 does not Self-Associate in Yeast

The MLA10 CC5-120 domain was able self-associate in solution to form a dimer. Moreover, the MLA10 CC-NB1-225 domain also self-interacted in yeast two-hybrid assays (Maekawa et al., 2011). To assess if the CC domain of Sr33 was able to self-interact, a directed yeast two-hybrid analysis was performed. Co-expression of three truncated Sr33 CC domain variants (equivalent to a truncated portion of the CC domain (CC1-125), the entire CC domain (CC1-160) and the CC-NB domain (CC1-225)) as both bait and prey failed to detect Sr33 CC domain self-association.

Example 7. Structure-Function Analysis of SR33

As described in Example 3, the Sr33 polypeptide contains the domains CC-NB-LRR. For CC-NB-LRR proteins, it is thought that the CC domain is required for signalling the initiation of an hypersensitive response (HR), the central NB-ARC region is involved in protein regulation and the LRR domain is involved in ligand recognition. To test if this model was correct for the Sr33 polypeptide and in order to dissect the relative contribution of the subdomains present in Sr33 on overall protein function, Sr33 was subjected to either domain truncation or site-directed mutagenesis (SDM) of particular amino acids. The amino acids selected for targeted SDM all corresponded to conserved amino acids in the same positions that have been shown to be important for protein function of MLA10, an ortholog of Sr33 from barley.

The experiment was performed using vector pTN with protein expression controlled by a CaMV 35S promoter. This vector was transformed into *Agrobacterium strain GV*3101 and introduced into three week old *N. benthamiana* plants through pressure infiltration of the abaxial surface of leaves. Data was obtained 72-96 hrs post inoculation.

The CC Domain of Sr33 Signals HR in *N. benthamiana*

Sr33 was truncated into five arrangements as indicated in FIG. 7 (#1-5) and a genetic construct generated for expression of each truncated polypeptide in the pTN vector. Each construct was tested for an ability to induce HR in *N. benthamiana* leaves, including the construct for expression of the full length polypeptide of 961 amino acid residues (#6 in FIG. 7). In this experiment an empty vector served as a negative control while the MLA10 CC domain (amino acid 1-160) acted as a positive control for HR induction. Visual inspection of the inoculated leaves indicated that only the truncated versions of Sr33 containing the CC domain (i.e. the 1. CC, 2. CC-NB, 3.CC-NB-ARC, but not the full length Sr33), were able to induce a weak HR associated with Sr33 function. Accordingly, amino acids 1-160 of both the Sr33 and MLA10 polypeptides (CC domains) were expressed under the control of the CaMV35S promoter in Gateway vector pBIN. Using this particular vector a stronger, more obvious HR was observed, confirming that the CC domain of Sr33 was both necessary and sufficient to induce HR in planta.

Example 8. Site Directed Mutagenesis of Sr33 at F99 or D501 Autoactivates SR33 while K207 Inactivates SR33

Site-directed mutants of Sr33 were expressed in *N. benthamiana* leaves in the same way. Visual inspection indicated that full length Sr33 was not able to induce an HR when expressed in *N. benthamiana*. The Sr33 polypeptide contained two conserved amino acids, that when mutated in MLA10, have been shown to autoactivate the FL protein. The corresponding first amino acid in Sr33 was a phenylalanine (F) at position 99 (F99) in the CC domain and the second was an aspartic acid (D) at position 501 (D501) in the MHD motif of the ARC domain. Moreover, Sr33 contained another conserved amino acid that when mutated in MLA10, had been shown to inactivate the FL protein. This amino acid was a lysine (K) at position 207 (K207) in the P-loop of the NB domain. When tested in *N. benthamiana*, individually the F99E and D501V mutations were found to autoactivate Sr33, both providing a strong visible HR, while the K207R had no effect. However, when the K207R mutation was made in combination with the F99E or D501V mutation, this modification was found to attenuate/inactivate the auto-activating activity.

Example 9. Discussion

The high resolution genetic and physical mapping described in Example 1 revealed the presence of a cluster of genes each encoding an NB-LRR protein, including at least six gene members spanning the Sr33 locus. Induced mutants and complementation analyses confirmed that a single gene, AetRGA1e, within the cluster was required and sufficient to confer Sr33-mediated resistance. A dis-similar NB-LRR gene, AetRGA2, was identified to be closely linked to Sr33. There is increasing evidence for pairs of dissimilar NB-LRR genes to function together in mediating disease resistance against pathogen isolates as reported for wheat leaf rust (Lr10), rice blast (Pikm), bacterial wilt and bacterial speck (RRS1/RPS4) as well as downy mildew (RPP2) in *Arabidopsis* (Eitas and Dangl, 2010). In the case of Sr33, gene silencing experiments through knockdown of the adjacent AetRGA2a gene had no effect on Sr33 mediated resistance, indicating that AetRGA2a was not necessary for the resistance gene function. It was noteworthy that AetRGA2a possessed a novel C terminus with an exocyst70 subunit domain. While gene fusions involving NB-LRR proteins and other functionally diverse protein domains such as kinases and WRKY transcription factors are known (Brueggeman et al., 2008; Narusaka et al., 2009), this is the first time a NB-LRR-Exocst70 subunit fused protein has been reported.

Comparative genetic analysis of the Sr33 region across the A and D genomes of wheat and the corresponding chromosomal region in barley revealed a conservation of Bpm-like (RNA binding protein) and Mla-related mildew resistance gene family (Wei et al., 2002; Jordan et al., 2011). In barley, all of the known functional Mla alleles belong to one class of the resistance gene analogs (Seeholzer et al., 2010) from the mixed cluster of genes at the Mla locus. Sr33 shares sequence identity of up to 86% with the Mla alleles in barley and the diploid A genome progenitor *T. monococcum*. To date, only race specific resistance against powdery mildew (*Blumeria graminis*) has been reported for the barley (HvMla) and *T. monococcum* (TmMla) locus. The Examples above described that a gene related in sequence to Mla, namely the Sr33 gene at the orthologous locus in the D genome of wheat, conferred resistance against a different pathogen from mildew, namely wheat stem rust—*Puccinia graminis*. Previous genetic studies mapped the stem rust R genes Sr31 and SrR (now designated Sr50) to the homoeologous loci of rye Mla related gene members found in cereal rye chromosomal segments introgressed into wheat (Mago et al., 2002). It is possible that Sr33, Sr31 and Sr50 constitute a homoeologous set of a lineage of Mla-like genes for wheat stem rust resistance.

The broad-spectrum intermediate immune capacity mediated by Sr33 was shown to function independently of the protein chaperones HSP90, SGT1 and RAR1. VIGS analysis did not distinguish an altered stem rust resistance state in wheat. No interaction was detected between Sr33 and these proteins when co-expressed in a yeast two-hybrid system. It is well established that proper function of a subset of plant NB-LRR type R proteins is dependent on theses chaperones. Such an association is thought to promote folding, maturation and stability of compatible R proteins (Jordan et al., 2011). The data indicated that Sr33 does not require maintenance and/or regulation from these components of the cellular machinery for stem rust resistance.

The CC domain of HvMLA10 forms homodimers, an attribute necessary for cell death signaling capabilities of this protein (Maekawa et al., 2011). Moreover, MLA10 interacts directly through a CC domain interface with two WRKY (WRKY1/2) transcription factors (Shen et al., 2007). In addition, the CC domain of MLA1 from diploid wheat *T. monococcum* is able to interact directly with HvWRKY1 (Jordan et al., 2011). This indicated that upon protein activation, the CC domain of NB-LRR type R proteins likely functions as the signalling architecture, initiating and coordinating downstream immune responses. Using three Sr33 CC domain variants representative of a truncated portion of the CC domain (CC1-125), the entire CC domain (CC1-160) and the CC-NB domain (CC1-225) the inventors were unable to detect Sr33 CC self-association in yeast. This indicated that either Sr33 CC dimers do not form in yeast or CC homodimerisation is not an exclusive feature of all CC-type R proteins. In addition, the Sr33 CC domain did not interact with either barley or *Ae. tauchii* WRKY1/2.

The single amino acid variant Asp588Asn found in haplotype II from the accession PI603225 appeared to not alter stem rust resistance function. In allelism tests involving the multiple pathogen isolate phenotype of PI603225 and the original Sr33 donor, no susceptible plants were obtained in the progeny providing further support that haplotypes I and II were variants that both functioned as resistance alleles.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from AU 2013902049 filed 6 Jun. 2013, the entire contents of which are incorporated herein by reference.

All publications discussed and/or referenced herein are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.

Akhunov et al. (2003) Genome Research 13:753-763.

Akhunov et al. (2010) BMC Genomics 11:702.

Ayliffe et al. (2011) Mol Plant Microbe. Interact. 24:1143-1155.

Bam et al. (2008) Proc S Afr Sug Technol Ass 81:508-512.

Bariana and McIntosh (1993) Genome 36:476-482.

Barker et al. (1983) Plant Mol. Biol. 2: 235-350.

Bernoux et al. (2011) Cell Host Microbe. 9:200-211.

Bevan et al. (1983) Nucl. Acid Res. 11: 369-385.

Bieri et al. (2004) Plant Cell 16: 3480-3495.

Brueggeman et al. (2008) Proc Natl Acad Sci USA 105: 14970-14975.

Cadwell and Joyce (1992) PCR Methods Appl. 2:28-33.

Capecchi (1980) Cell 22:479-488.

Cheng et al. (1996) Plant Cell Rep. 15:653-657.

Clapp (1993) Clin. Perinatol. 20:155-168.

Cloutier et al. (2007) Plant Mol Biol 65:93-106.

Coco et al. (2001) Nature Biotechnology 19:354-359.

Coco et al. (2002) Nature Biotechnology 20:1246-1250.

Comai et al. (2004) Plant J 37: 778-786.

Cooley et al. (2000) Plant Cell 12:663-676.

Crameri et al. (1998) Nature 391:288-291.

Curiel et al. (1992) Hum. Gen. Ther. 3:147-154.

Duplessis et al. (2011) Proc Natl Acad Sci USA 108:9166-9171.

Eggert et al. (2005) Chembiochem 6:1062-1067.

Eglitis et al. (1988) Biotechniques 6:608-614.
Eitas and Dangl (2010) Curr Opin Plant Biol 13:1-6.
Enkhbayar et al. (2004) Proteins 54:394-403.
Feuillet et al. (2003) Proc Natl Acad Sci 100:15253-15258.
Fujimura et al. (1985) Plant Tissue Cultural Letters 2:74.
Garfinkel et al. (1983) Cell 27: 143-153.
Gietz and Woods (2002) Meth. Enzymol. 350:87-96.
Graham et al. (1973) Virology 54:536-539.
Grant et al. (1995) Plant Cell Rep. 15:254-258.
Greve (1983) J. Mol. Appl. Genet. 1: 499-511.
Harayama (1998) Trends Biotechnol. 16:76-82.
Hayden et al. (2008) Mol. Breed 21:271-281.
Hellinga (1997) Proc. Natl. Acad. Sci. 94:10015-10017.
Henikoff et al. (2004) Plant Physiol 135: 630-636.
Hinchee et al. (1988) Biotech. 6:915
Huang et al. (2003) Genetics 164:655-664.
Jézéquel et al. (2008) Biotechniques 45:523-532.
Jin and Singh (2006) Plant Dis 90:476-480.
Jones et al. (1991) Genome 34:505-508.
Jordan et al. (2011) Plant J 65:610-621.
Joshi (1987) Nucl. Acid Res. 15: 6643-6653.
Kerber and Dyck (1979) Resistance to stem and leaf rust of wheat in *Aegilops squarrosa* and transfer of a gene for stem rust resistance to hexaploid wheat. P. 358-364. In S. Ramanujam (ed.) Proc. 5th Int. Wheat Genet Symp, New Delhi, India, 23-28 Feb. 1978.
Kosambi (1944) Ann. Eugen. 12:172-175.
Kota et al. (2006) Theor. Appl. Genet. 112:492-499.
Krattinger et al. (2009) Science 323:37-395.
Kushnirov (2000) Yeast 16:857-860.
Lagudah et al. (2006) Theor. Appl. Genet. 114:21-30.
Lagudah et al. (2009) Theor. Appl. Genet. 119:889-898.
Langridge et al. (2001) Aust. J. Agric. Res. 52: 1043-1077.
Leister et al. (2005) Plant Cell 17: 1268-1278.
Lemieux (2000) Current Genomics 1: 301-311.
Leung et al. (1989) Technique 1:11-15.
Lu and Berry (2007) Protein Structure Design and Engineering, Handbook of Proteins 2: 1153-1157.
Lu et al. (1993) J. Exp. Med. 178: 2089-2096.
Luo et al. (2003) Genomics 82:378-389.
Maas et al. (1997) Mol. Breed 3:15-28.
Maekawa et al. (2011) Cell Host Microbe 9:187-199.
Mago et al. (2002) Theor Appl Genet 104:1317-1324.
Mago et al. (2002) Theor. Appl. Genet. 104:1317-1324.
Mago et al. (2005) Theor Appl Genet. 112:41-50.
Manly et al. (2001) Mammalian Genome 12:930-9321.
Medberry et al. (1992) Plant Cell 4: 185-192.
Medberry et al. (1993) Plant J. 3: 619-626.
Meyers et al. (1999) Plant Journal 20:317-332.
Michelmore and Meyers (1998) Genome Res. 8:1113-1130.
Moullet et al. (1999) Theor Appl Genet 99:305-313.
Moullet et al. (1999) Theor. Appl. Genet. 99:303-313.
Narusaka et al. (2009) Plant J 60:218-226
Needleman and Wunsch (1970) J. Mol Biol. 45:443-453.
Ness et al. (2002) Nature Biotechnology 20:1251-1255.
Niedz et al. (1995) Plant Cell Reports 14: 403-406.
Olson et al. (2013) Theor Appl Genet (DOI 10.1007/s00122-013-2045-5).
Ostermeier et al. (1999) Nature Biotechnology 17:1205-1209.
Ow et al. (1986) Science 234: 856-859.
Pan et al. (2000) J. Mol. Evol. 50:203-2013.
Petty et al. (1989) Virology 171:342-349.
Prasher et al. (1985) Biochem. Biophys. Res. Comm. 126: 1259-68.
Rouse et al. (2011) Crop Sci 51:2074-2078.
Salomon et al. (1984) EMBO J. 3: 141-146.
Scofield et al. (2005) Plant Physiol 138:2165-2173.
Scofield et al. (2005) Plant. Physiol. 138:2165-2173.
Seeholzer et al. (2010) Mol Plant Microbe Interact 23:497-509.
Shen et al. (2007) Science 325:1098-103.
Shirasu (2009) Annu Rev Plant Biol 60:139-164.
Sieber et al. (2001) Nature Biotechnology 19:456-460.
Singh et al. (2011) Annu Rev Phytopathol 49:465-481.
Slade and Knauf (2005) Transgenic Res. 14: 109-115.
Somers et al. (2004) Theor. Appl. Genet. 109:1105-1114.
Stalker et al. (1988) Science 242:419-423.
Stemmer (1994a) Proc. Natl. Acad. Sci. USA 91:10747-10751.
Stemmer (1994b) Nature 370(6488):389-391.
Tai (2008) Mol. Biol. Rep. 35:337-343.
Tameling et al. (2002) Plant Cell 14:2929-2939.
Thillet et al. (1988) J. Biol. Chem. 263:12500.
Toriyama et al. (1986) Theor. Appl. Genet. 205:34.
Traut (1994) Eur. J. Biochem. 222:9-19.
Volkov et al. (1999) Nucleic Acids Research 27:e18.
Wagner et al. (1992) Proc. Natl. Acad. Sci. USA 89:6099-6103.
Wang et al. (1998) Acta. Hortic. 461:401-405.
Wang et al. (2011) New Phytologist. 191: 418-431.
Wei et al. (2002) Plant Cell 14:1903-1917.
Zhang et al. (2010) Mol. Cell 39:269-281.
Zhao et al. (1998) Nature Biotechnology 16:258-261.

The invention claimed is:

1. A transgenic plant which has integrated into its genome a transgene comprising an exogenous polynucleotide encoding an Sr33 polypeptide, the polypeptide comprising an amino acid sequence which is at least 95% identical to the sequence set forth as SEQ ID NO: 1, wherein the polynucleotide is operably linked to a promoter capable of directing expression of the polynucleotide in a cell of the plant.

2. The plant of claim 1 which has enhanced resistance to *Puccinia graminis* when compared to an isogenic plant lacking the transgene.

3. The plant of claim 2, wherein the *Puccinia graminis* is *Puccinia graminis* f. sp. *tritici*.

4. The plant of claim 3, wherein the *Puccinia graminis* f. sp. *tritici* is a race of the Ug99 group.

5. The plant of claim 1, wherein the polynucleotide comprises nucleotides having a sequence as provided in SEQ ID NO:3 or SEQ ID NO:4, or a sequence which is at least 90% identical to SEQ ID NO:3 or SEQ ID NO:4.

6. The plant of claim 1 which is a cereal plant.

7. The plant of claim 6 which is a wheat plant.

8. The plant of claim 1 which is homozygous for the exogenous polynucleotide.

9. A seed of the plant of claim 1, wherein the seed comprises the polynucleotide encoding the Sr33 polypeptide.

10. A product produced from the plant of claim 1 or seed thereof, wherein the product is a food product or beverage product.

11. Flour or wholemeal comprising a transgene comprising an exogenous polynucleotide encoding an Sr33 polypeptide, the polypeptide comprising an amino acid sequence which is at least 95% identical to the sequence set forth as SEQ ID NO: 1.

12. A method of producing a plant part, the method comprising, a) growing a plant of claim 1, and b) harvesting the plant part.

13. A method of producing flour, wholemeal, starch or other product obtained from seed, the method comprising;

a) obtaining seed of claim 9, and b) extracting the flour, wholemeal, starch or other product.

14. A method of preparing the food product of claim 10, the method comprising mixing seed, or flour, wholemeal or starch from the seed, with another food ingredient.

15. A chimeric vector comprising a polynucleotide which encodes an Sr33 polypeptide, the polypeptide comprising an amino acid sequence which is at least 95% identical to the sequence set forth as SEQ ID NO: 1, wherein the polynucleotide is operably linked to a promoter.

16. The chimeric vector of claim 15, wherein the polynucleotide has the sequence set forth as SEQ ID NO: 3 or SEQ ID NO: 4, or a sequence which is at least 90% identical to SEQ ID NO: 3 or SEQ ID NO: 4, or a sequence encoding a polypeptide having the amino acid sequence set forth as SEQ ID NO: 1 or SEQ ID NO: 2.

17. A method of producing an Sr33 polypeptide, the polypeptide comprising an amino acid sequence which is at least 95% identical to the sequence set forth as SEQ ID NO:1, the method comprising; a) cultivating the transgenic plant of claim 1, and b) isolating the polypeptide from the plant.

18. A method of producing a transgenic plant, the method comprising the steps of i) introducing the vector of claim 15 into a cell of a plant, and ii) regenerating a transgenic plant from the cell, thereby producing the transgenic plant.

19. A method of producing a plant which has integrated into its genome a transgene comprising a polynucleotide encoding an Sr33 polypeptide, the polypeptide comprising an amino acid sequence which is at least 95% identical to the sequence set forth as SEQ ID NO:1, the method comprising the steps of i) crossing two parental plants, wherein at least one parental plant is the plant of claim 1, ii) screening one or more progeny plants from the cross for the presence or absence of the polynucleotide, and iii) selecting a progeny plant which comprises the polynucleotide, thereby producing the plant.

20. A process for identifying a genetically modified plant exhibiting enhanced resistance to *Puccinia graminis* relative to a corresponding plant lacking the genetic modification, the process comprising: (i) exposing a genetically modified plant to *Puccinia graminis*, wherein the plant is genetically modified to express a transgene which encodes an Sr33 polypeptide comprising an amino acid sequence which is at least 95% identical to the amino acid sequence set forth as SEQ ID NO: 1; and (ii) determining if the genetically modified plant has enhanced resistance to the *Puccinia graminis*; wherein if the genetically modified plant exhibits a level of *Puccinia graminis* resistance that is enhanced when compared to the plant lacking the genetic modification, the genetically modified plant is identified as having enhanced *Puccinia graminis* resistance.

21. The plant of claim 1, wherein the polypeptide comprises amino acids having the sequence set forth as SEQ ID NO:1.

22. The plant of claim 1, wherein the polypeptide comprises amino acids having the sequence set forth as SEQ ID NO:2.

23. The food product of claim 10, wherein the food product comprises the polypeptide comprising an amino acid sequence set forth as SEQ ID NO:1.

24. The method of claim 18, comprising producing one or more progeny plants from the regenerated transgenic plant, or harvesting seed from the regenerated transgenic plant or the one or more progeny plants.

* * * * *